US010159679B2

(12) United States Patent
Barnham et al.

(10) Patent No.: US 10,159,679 B2
(45) Date of Patent: Dec. 25, 2018

(54) METAL DELIVERY AGENTS AND THERAPEUTIC USES OF THE SAME

(71) Applicant: The University of Melbourne, Victoria (AU)

(72) Inventors: Kevin J. Barnham, Coburg (AU); Paul S. Donnelly, Carlton (AU); Anthony R. White, Coburg (AU)

(*) Notice: Subject to any disclaimer, the term of this patent is extended or adjusted under 35 U.S.C. 154(b) by 163 days.

(21) Appl. No.: 14/571,938

(22) Filed: Dec. 16, 2014

(65) Prior Publication Data

US 2015/0105461 A1 Apr. 16, 2015

Related U.S. Application Data

(63) Continuation of application No. 12/515,473, filed as application No. PCT/AU2007/001792 on Nov. 20, 2007.

(Continued)

(51) Int. Cl.
| | | |
|---|---|---|
| *A61K 31/55* | (2006.01) | |
| *A61K 31/555* | (2006.01) | |
| *A61K 31/145* | (2006.01) | |
| *A61K 31/28* | (2006.01) | |
| *A61K 31/30* | (2006.01) | |
| *A61K 31/315* | (2006.01) | |

(Continued)

(52) U.S. Cl.
CPC .......... *A61K 31/555* (2013.01); *A61K 31/145* (2013.01); *A61K 31/28* (2013.01); *A61K 31/30* (2013.01); *A61K 31/315* (2013.01); *C07F 1/08* (2013.01); *C07F 3/06* (2013.01)

(58) Field of Classification Search
CPC .... A61K 31/555; A61K 31/145; A61K 31/30; A61K 31/28; A61K 31/315; C07F 3/06; C07F 1/08
See application file for complete search history.

(56) References Cited

U.S. PATENT DOCUMENTS

| | | | |
|---|---|---|---|
| 2008/0206251 A1* | 8/2008 | Cashman | A61K 31/7088 424/139.1 |
| 2012/0270850 A1 | 10/2012 | Barnham et al. | |

FOREIGN PATENT DOCUMENTS

| | | |
|---|---|---|
| JP | 10-101566 A | 4/1998 |
| WO | WO2007/003944 A2 | 1/2007 |
| WO | WO2015/070177 A2 | 5/2015 |

OTHER PUBLICATIONS

Cudkowicz et al (Annals of Neurology. vol. 60 No. 1 Jul. 2006).*

(Continued)

*Primary Examiner* — Angela C Brown-Pettigrew
(74) *Attorney, Agent, or Firm* — Cermak Nakajima & McGowan LLP; Malcolm K. McGowan

(57) ABSTRACT

The present invention relates to metal complexes, processes for their preparation and their use as pharmaceutical or veterinary agents, in particular for the treatment of conditions in which metal delivery can prevent, alleviate or ameliorate the condition. There are a number of clinical conditions which are caused by or associated with abnormal levels of metals (typically low metal levels). Conditions in of this type include cancer and conditions characterized by or associated with oxidative damage, more specifically neurodegenerative conditions such as Alzheimer's disease, Parkinson's disease or Huntington's disease. The invention also relates to ligands useful in the preparation of metal complexes of this type.

20 Claims, 15 Drawing Sheets

Related U.S. Application Data

(60) Provisional application No. 60/859,921, filed on Nov. 20, 2006.

(51) Int. Cl.
  *C07F 1/08* (2006.01)
  *C07F 3/06* (2006.01)

(56) References Cited

OTHER PUBLICATIONS

Kalra et al (AJNR Am Neuroradiol 24:476-480, Mar. 2003).*
Wada et al (Archives of biochemistry of biochemistry and biophysics vol. 310, No. 1, April, pp. 1-5, 1994).*
Wada et al (Archives of biochemistry of biochemistry and biophysics vol. 310, No. 1, April, pp. 1-5, 1994) (Year: 1994).*
"International Application Serial No. PCT/AU2007/001792, International Search Report completed Dec. 6, 2007", 4 pgs.
Kubota, M., et al., "Mechanisms of [2, 3-Butanedione Bis(N4-Dimethylthiosemicarbazone)]zinc (Zn-ATSM2)-Induced Protection of Cultured Hippocampal Neurons Against N-Methyl-D-Aspartate Receptor-Mediated Glutamate Cytotoxicity," Japanese Journal of Pharmacology, 84(3), (2000), 334-338.
Lewis, J.S., et al., "Copper-64-diacetyl-bis(N4-methylthiosemicarbazone): An agent for radiotherapy," Proc. Natl. Acad. Sci. USA, 98(3), (2001), 1206-1211.
"European Application Serial No. EP07815594, Supplemental European Search Report completed Mar. 15, 2010," 12 pgs.
Bayer, T.A., et al., "Dietary Cu stabilizes brain superoxide dismutase 1 activity and reduces amyloid Abeta production in APP23 transgenic mice," Proc. Natl. Acad. Sci. USA, 100(23), (2003), 14187-14192.
Blower, P., et al., "Structural trends in copper(II) bix(thiosemicarbazone) radiopharmaceuticals," Dalton Trans., (2003), 4416-4425.
Bush, A. I., "Metals and Neuroscience," Current Opinion in Chemical Biology, 4, (2000), 184-191.
Coats, E. A., et al., "Comparative analysis of cellular respiratory inhibition by substituted phenylglyoxal-bis(4-methyl-3-thiosemicarbazone) zinc chelates," II Farmaco, Edizione Scientifica, 38(3), (1983), 143-152.
Dearling, J. L. J., et al., "Copper bis(thiosemicarbazone) complexes as hypoxia imaging agents: structure activity relationships," J. Biol. Inorg. Chem., 7, (2002), 249-259.
Dilanyan, E. R., et al., "Synthesis and Biological Activity of 3-ethoxy-2-oxobutyraldehydebisthiosemicarbzones and their complexes with Cu(II)," Pharmacy Chemistry Journal, 18(7), (English translation of paper published in Khimiko-Farmatsevticheskii Zhurnal, 18(7)) (Jul. 1984) at pp. 835-839, (1985), 491-494.
Genova, P., et al., "Toxic effects of bis(thiosemicarbazone) compounds and its palladium(II) complexes on herpes simplex virus growth," Toxicology and Applied Pharmacology, 197(2), (2004), 107-112.
Hall, J. H., et al., "The Cytotoxicity of Symmetrical and Unsymmetrical Bis(thiosemicarbazones) and Their Metal Complexes in Murine and Human Tumor Cells," Archiv der Pharmazie, 333(7), (2000), 217-225.
Kessler, H., et al., "Cerebrospinal fluid diagnostic markers correlate with lower plasma copper and ceruloplasmin in patients with Alzheimer's disease," Journal of Neural Transmission, 113, (2006), 1763-1769.
Matesanz, A. I., et al., "Synthesis and characterization of novel palladium (II) complexes of bis(thiosemicarbazone). Structure, cytotoxic activity and DNA binding of PD(II)-benzyl bis(thiosemicarbazone)," J. Inorg. Biochem., 76(1), (1999), 29-37.
McQuade, P., et al., "Investigation into 64Cu-labeled Bis-(selenosemicarbazone) and Bis(thiosemicarbazone) complexes as hypoxia imaging agents," Nuclear Medicine and Biology, 32, (2005), 147-156.
Ovsepyan, T. R., et al., "Novel bisthiosemicarbazones of glyoxal, benzil, and their chelates with copper (2+): synthesis and biological activity," Pharmaceutical Chemistry Journal, 23(6) (English Translation of paper published in Khimiko-Farmatsevticheskii Zhurnal, 23(6), (Jun. 1989), at pp. 678-682), (1990), 475-478.
Petering, H. G., et al., "Essential role of cupric ion in the biological activity of 3-ethoxy-2-oxobutyraldehyde bis (thiosemicarbazone), a new antitumor agent," The Biochemistry of Copper: Proceedings of the Symposium on Copper in Biological Systems, (Harriman, New York, NY, Sep. 8-10, 1965), (166), 197-209.
Saji, H., et al., "Brain permeable zinc complex with neuroprotective action," S. T. P. Pharma Sciences 199701, 7(1), (Jan. 1997), 92-97.
Wada, K., et al., "Copper (II)[2,3-Butanedionebis(N4-methylthiosemi carbaxzone)] a Stable Superoxide Dismutase-like Copper Complex with High Membrane Penetrability," Archives of Biochemistry and Biophysics, 310(1), (Apr. 1994), 1-5.
Wada, K., et al., "Cu-ATSM, an intracellular-accessible superoxide dismutase (SOD)-like copper complex: Evaluation in an ischemia-reperfusion injury model," Database Biosis [Online] Biosciences Information Service, (Abstract Only), (1994), 1 pg.
White, A. R., et al., "Degradation of the Alzheimer's diease β-Peptide by Metal-Dependent Up-regulation of Metalloprotease Activity," J. Biol. Chem., 281(26), (Jun. 2006), 17670-17680.
Zhong, X., et al., "Synthesis and crystal structure of some transition metal complexes with a novel bis-Schiff base ligand and their antitumor activities," European Journal of Medicinal Chemistry, 41(9), (2006), 1090-1092.
"Australian Application Serial No. 2007324345, Examiner's First Report dated Apr. 18, 2012," 4 pgs.
"European Application Serial No. 07815594.2, Office Action dated Feb. 8, 2012," 5 pgs.
"International Application Serial No. PCT/AU2007/001792, International Preliminary Report on Patentability dated May 26, 2009," 6 pgs.
"International Application Serial No. PCT/AU2007/001792, Written Opinion dated Dec. 12, 2007," 5 pgs.
Kessler, H., et al., "Intake of copper has no effect on cognition in patients with mild Alzheimer's disease: a pilot phase 2 clinical trial," Journal of Neural Transmission, 115, (2008), 1181-1187.
Szeto, H. H., et al., "Mitochondria-Targeted Peptide Antioxidants: Novel Neuroprotective Agents," The AAPS Journal, 8(3), (2006), E521-E531.
"European Application Serial No. 07815594.2, Response filed Aug. 7, 2012 to Office Action dated Feb. 8, 2012," 21 pgs.
"European Application Serial No. 07815594.2, Summons to Attend Oral Proceedings mailed Jul. 17, 2013," 6 pgs.
Butterfield, D. A., "The Glutamatergic System and Alzheimer's Disease," CNS Drugs, 17(9), (2003), 641-652.
Soon, C. P. W., et al., "Diacetylbis(N(4)-methylthiosemicarbazonato) Copper(II) (Cull (atsm)) Protects . . . ," Dec. 23, 2011, J. Bio. Chem., vol. 286, No. 51, pp. 44035-44044.
Wada, K., et al., Archives of biochemistry and biophysics, vol. 310, No. 1, April, pp. 1-5, 1994.
Siegel et al., CA Cancer J. Clin. 2012;62:220-241.
Sowers et al., Hypertension 2001;37:1053-1059.
Office Action from U.S. Appl. No. 15/593,679 dated Sep. 19, 2017.

* cited by examiner

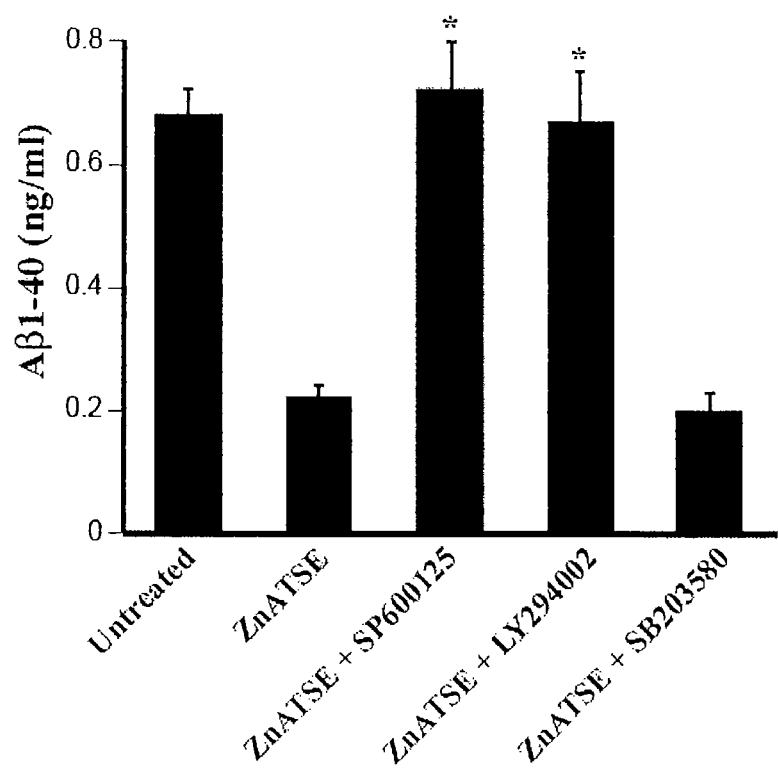

METAL DELIVERY AGENTS AND THERAPEUTIC USES OF THE SAME

This application is a continuation of U.S. application Ser. No. 12/515,473, filed Feb. 5, 2010, which is a national stage application under 35 U.S.C. § 371 of PCT/AU2007/001792, filed Nov. 20, 2007 and published as WO 200/061306 A1 on May 29, 2008, which claims priority under 35 U.S.C. § 119 to U.S. Application No. 60/859,921, filed Nov. 20, 2006, which applications and publication are incorporated by reference and made a part hereof in their entirety.

FIELD OF THE INVENTION

The present invention relates to the use of metal complexes as pharmaceutical or veterinary agents, in particular for the treatment of conditions in which metal delivery can prevent, alleviate or ameliorate the condition. There are a number of clinical conditions which are caused by or associated with abnormal levels of metals (typically low metal levels). Conditions in of this type include cancer and conditions characterised by or associated with oxidative damage, more specifically neurodegenerative conditions such as Alzheimer's disease, Parkinson's disease or Huntington's disease.

BACKGROUND OF THE INVENTION

The life span is thought to be biologically fixed for each species, and the length of the human life span is uncertain, but may be up to 120 years. Since life expectancy has risen significantly in this century, the elderly are an increasing segment of our population, and their health care needs will continue to grow for decades.

Bio-available metal ions play crucial roles in a number of important biological processes. It is estimated that one-third of all proteins are metalloproteins (proteins containing a tightly bound metal ion) and therefore a number of biologically important processes are impaired if bio-available metal levels are either elevated or suppressed. In addition even if there are adequate levels of bio-available metal in a biological system it is important that its distribution in the biological system be such that the biological processes that rely on the presence of the metal function appropriately.

Whilst there is a wide range of ways in which bio-available metals impact on biological systems, two of the better known would be the role of metals in enzyme systems and the role of metals in signaling mechanisms within biological systems. Examples of the role of metals in biological processes include the potential importance of Zn in the ß-amyloid plaques of Alzheimer's disease; the effect of the (Cu, Zn) superoxide dismutase enzyme in mediating reactive oxygen species damage associated with amyotrophic lateral sclerosis; the participation of the heme enzymes NO synthase and guanylyl cyclase in the production and sensing, respectively, of nitric oxide (NO), and the discovery of a "zinc-finger" motif in the breast and ovarian cancer susceptibility gene, BRCA1 merely by way of example. It is also known that Cu plays a role in XIAP activity which modulates caspase activity which in turn controls apoptosis. Apopotosis is a process of controlled cell death and dysregulation of this process has been implicated in many disease states.

A large percentage of newly discovered enzymes and proteins also contain metal ions at their active sites and variations in metal levels can significantly interfere with the functioning of these enzymes and proteins. Metalloenzymes of this type are involved in a number of important bio catalytic processes including reduction of excess oxygen species. Accordingly whenever there is either too high or too low a level of metals present in a biological system either too high a level or too low a level the normal biological processes are interrupted, typically leading to undesirable consequences. This typically occurs as many of the crucial enzymatic processes that provide protection in the biological system are suppressed or inactivated leading to undesirable consequences.

As a result of the importance of metals in the biological environment, research conducted into the roles of metals in biological systems have identified a number of conditions which are caused by or associated with abnormal levels of metal in the biological environment. In respect of these conditions they are all typically ones in which metal delivery can prevent, alleviate or ameliorate the condition. An example of a condition of this type is oxidative stress which is related to abnormal metal levels as many of the protective enzymes responsible for alleviating oxidative stress are deactivated if biological metal levels are too low.

Research in the last few decades has identified that there are a number of conditions that are caused by or associated with oxidative stress placed on the body. For example a number of cardiovascular conditions have been identified that are the result of oxidative stress (OS). Other conditions associated with OS include cancer, cataracts, neurodegenerative disorders such as Alzheimer's disease and heart diseases. In addition, there's evidence that OS plays a prominent role in three types of neuromuscular disorders: amyotrophic lateral sclerosis (ALS), mitochondrial/metabolic disease and Friedreich's ataxia.

The effect of OS is not limited to any one part of the human body, with examples of the negative effects of OS being observed for almost all organs. For example, the human brain is an organ that concentrates metal ions and recent evidence suggests that a breakdown in metal homeostasis plays a critical role in a variety of age-related neurodegenerative diseases. Common features of these diseases include the deposition of misfolded protein (each disease can have its own specific amyloid protein) and substantial cellular damage as a result of OS. Significant data suggests that OS is the primary cause of physical damage in a wide range of disease states, including amyloidogenic neurological disorders such as Alzheimer's disease (AD), amylotrophic lateral sclerosis (ALS), prion diseases—including Creutzfeldt-Jakob Disease (CJD), transmissible spongioform encephalopathies (TSE), cataracts, mitochondrial disorders, Menke's disease, Parkinson's disease (PD) and Huntington's disease (HD). [Bush, 2000 (Curr Opin Chem. Biol. 2000 April; 4(2):184-91)].

In this regard it is notable that Copper metal ion deficiency has been reported as a condition associated with AD. Copper is an essential element that is required for many enzymes to function properly, particularly those enzymes that maintain a balance in antioxidant/pro-oxidant homeostasis such as superoxide dismutase and cytochrome C oxidase. One consequence of copper deficiency is that the protective enzymes responsible for detoxifying reactive oxygen species (ROS) are inadequately loaded with copper and therefore do not effectively carry out normal enzyme function. The inadequate loading of such protective enzymes, for example in the brain, leads to a general increase in OS (as is observed in AD) which will be reflected in increased protein oxidation, such as increased protein carbonyls.

A number of therapeutic agents have been developed in an attempt to provide therapeutic solutions to the conditions caused by or associated with OS as discussed above with varied results. In general, in order to lower OS levels, various antioxidants are being used. The most common are vitamin E and vitamin C. However, vitamin E was found to be ineffective at decreasing the oxidative stress at the substantia nigra (The Parkinson Study Group, 1993, Offen et al., 1996) since this compound, although capable of crossing the blood brain barrier, is trapped in the cell membrane and therefore does not reach the cytoplasm where its antioxidant properties are needed. Vitamin C also does not cross the blood brain barrier and therefore, cannot be used effectively for neurodegenerative diseases of central origin.

There is thus still a need for, and it would be highly advantageous to have novel antioxidant compounds and methods for use of antioxidants in treatment of disease associated with oxidative damage and particularly central nervous system neurodegenerative disorders such as PD, AD and CJD. Treatment is further desirable for and in treating conditions of peripheral tissues, such as acute respiratory distress syndrome, ALS, atherosclerotic cardiovascular disease and multiple organ dysfunction. During such treatment the complexes can act as oxygen scavengers to lower the OS within and in the vicinity of affected cells and this treatment eventually stops cell death which is associated with OS in the brain and/or peripheral tissues.

The present invention is therefore based on the finding that certain metal complexes are effective in delivering bio-available metal and could thus be used in the treatment of conditions which can be prevented, treated or ameliorated by metal delivery. In certain conditions it is desirable that the metal be released in the cell such that after metal delivery the metal is present in the form of the free cation and it is the free cation that leads to the observed biological activity. In respect of other conditions it is desirable that the metal stay in the form of the bound complex even after metal delivery and with these conditions it is the bound form of the metal (the metal complex) that is biologically active in the cell.

In particular these complexes were found to be effective in delivering metal to the cells in a form which lead to a significant anti-oxidant effect being observed in the cell. Thus, certain metal complexes demonstrated an ability to mediate OS.

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in Australia or in any other country.

SUMMARY OF THE INVENTION

In one aspect the invention provides a method of treatment or prophylaxis of a condition in a subject in which metal delivery can prevent, alleviate or ameliorate the condition, the method including administration of a therapeutically effective amount of a metal complex of Formula (I).

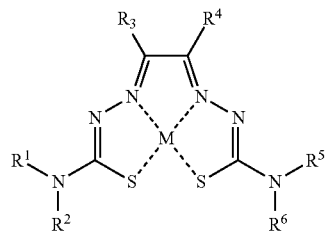

Formula (I)

wherein M is a divalent metal;

$R^1$ and $R^2$ are each independently selected from the group consisting of: H, alkyl, alkenyl, alkynyl, heteroalkyl, cycloalkyl, heterocycloalkyl, aryl, heteroaryl, hydroxy, hydroxyalkyl, alkoxy, $-N=R^7$, $-NH(R_7)$, $-N(R^7)_2$, $-COOH$, $-COR^7$, $-COOR^7$, $-CONHR^7$, $-CSNHR^7$, $-S(O)R^7$, $-S(O)_2R^7$, $-C(O)N(R^7)_2$, $-SO_2N(R^7)_2$, $-(CH_2)_mR^8$ and acyl, each of which may be optionally substituted; or $R^1$ and $R^2$ when taken together to the nitrogen atom to which they are attached form an optionally substituted heterocycloalkyl or heteroaryl group;

$R^3$ and $R^4$ are each independently selected from the group consisting of: H, alkyl, alkenyl, alkynyl, heteroalkyl, cycloalkyl, heterocycloalkyl, aryl, heteroaryl, each of which may be optionally substituted;

or $R^3$ and $R^4$ when taken together with the carbon atoms to which they are attached form an optionally substituted cycloalkyl group;

$R^5$ and $R^6$ are each independently selected from the group consisting of: H, alkyl, alkenyl, alkynyl, heteroalkyl, cycloalkyl, heterocycloalkyl, aryl, heteroaryl, hydroxy, hydroxyalkyl, alkoxy, $-N=R^7$, $-NH(R_7)$, $-N(R_7)_2$, $-COOH$, $-COR^7$, $-COOR^7$, $-CONHR^7$, $-CSNHR^7$, $-S(O)R^7$, $-S(O)_2R^7$, $-C(O)N(R^7)_2$, $-SO_2N(R^7)_2$, $-(CH_2)_mR^8$ and acyl, each of which may be optionally substituted; or $R^5$ and $R^6$ when taken together to the nitrogen atom to which they are attached form an optionally substituted heterocycloalkyl or heteroaryl group;

each $R^7$ is independently selected from the group consisting of H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl, and acyl, each of which may be optionally substituted;

each $R^8$ is independently selected from the group consisting of cycloalkyl, heterocycloalkyl, aryl, and heteroaryl, each of which may be optionally substituted;

m is an integer selected from the group consisting of 1, 2, 3, 4, 5 and 6.

In one embodiment the condition is selected from the group consisting of tau related disorders, disorders caused by or associated with oxidative stress in a subject, and Abeta related disorders. In one specific embodiment the condition is caused by or associated with oxidative stress in the subject. In another specific embodiment the condition is a tau related disorder, particularly a tau related neurodegenerative disorder. In another aspect the condition is an Abeta related disorder.

In a further aspect the invention provides the use of a metal complex of formula (I) in the preparation of a medicament for the treatment or prophylaxis of a condition in which metal delivery can prevent, alleviate or ameliorate the condition. In one embodiment the condition is selected from the group consisting of tau related disorders, disorders caused by or associated with oxidative stress in a subject, and Abeta related disorders. In one specific embodiment the condition is caused by or associated with oxidative stress in the subject. In another specific embodiment the condition is a tau related disorder, particularly a tau related neurodegenerative disorder. In another aspect the condition is an Abeta related disorder.

In one form of each of these two aspects the condition is selected from the group consisting of cardiovascular disease, central nervous system disorders, cancers and neurological disorders.

Examples of conditions of this type include conditions selected from the group consisting of acute intermittent porphyria; adriamycin-induced cardiomyopathy; AIDS dementia and HIV-1 induced neurotoxicity; Alzheimer's disease; amylotrophic lateral sclerosis; atherosclerosis; cataract; cerebral ischaemia; cerebral palsy; cerebral tumour; chemotherapy-induced organ damage; cisplatin-induced nephrotoxicity; coronary artery bypass surgery; Creutzfeldt-Jacob disease and its new variant associated with "mad cow" disease; diabetic neuropathy; Down's syndrome; near drowning; epilepsy and post-traumatic epilepsy; Friedrich's ataxia; frontotemporal dementia; glaucoma; glomerulopathy; haemochromatosis; haemodialysis; haemolysis; haemolytic uraemic syndrome (Weil's disease); Menke's disease; haemorrhagic stroke; Hallerboden-Spatz disease; heart attack and reperfusion injury; Huntington's disease; Lewy body disease; intermittent claudication; ischaemic stroke; inflammatory bowel disease; macular degeneration; malaria; methanol-induced toxicity; meningitis (aseptic and tuberculous); motor neuron disease; multiple sclerosis; multiple system atrophy; myocardial ischaemia; neoplasia; Parkinson's disease; pen-natal asphyxia; Pick's disease; progressive supra-nuclear palsy; radiotherapy-induced organ damage; restenosis after angioplasty; retinopathy; senile dementia; schizophrenia; sepsis; septic shock; spongiform encephalopathies; subharrachnoid haemorrage/cerebral vasospasm; subdural haematoma; surgical trauma, including neurosurgery; thalassemia; transient ischaemic attack (TIA); transplantation; vascular dementia; viral meningitis; and viral encephalitis.

In one specific embodiment the condition is a neurological disorder. In one form of this embodiment the neurological disorder is selected from the group consisting of Parkinson's disease, Alzheimer's disease, Multiple sclerosis, Neuropathies, Huntington's disease, Prion disease, motor neurone disease, Amyotrophic lateral sclerosis (ALS) and Menke's disease. In a specific embodiment the disorder is Alzheimer's disease. In a specific embodiment the disorder is Parkinson's disease. In a specific embodiment the disorder is Amyotrophic lateral sclerosis (ALS).

In a further aspect the invention provides a method of prophylaxis or treatment of oxidative stress including administering a therapeutically effective amount of a metal complex of formula (I) to the subject.

In a further aspect the invention provides the use of a metal complex of formula (I) in the preparation of a medicament for the treatment or prophylaxis of OS.

In an even further aspect the invention provides a method of protecting a cell from OS the method including exposing the cell to an effective amount of a metal complex of formula (I). In one embodiment the cell is a cell in a subject and exposing the cell to the metal complex includes administering the metal complex to the subject.

In an even further aspect the invention provides a method of prophylaxis or treatment of a tau related disorder the method including administering a therapeutically effective amount of a metal complex of formula (I) to the subject. In one embodiment the tau related disorder is a neurodegenerative disorder.

In a further aspect the invention provides the use of a metal complex of formula (I) in the preparation of a medicament for the treatment or prophylaxis of a tau related disorder.

In yet an even further aspect the invention provides a method of reducing or preventing the effects of Abeta on a cell the method including exposing the cell to an effective amount of a metal complex of the formula (I). In one embodiment the cell is a cell in a subject and exposing the cell to the metal complex includes administering the metal complex to the subject.

In yet an even further aspect the invention provides a method of prophylaxis or treatment of an Abeta related disorder the method including administering a therapeutically effective amount of a metal complex of formula (I) to the subject.

In yet a further aspect the present invention provides a method of phosphorylation of a kinase in a cell, the method including exposing the cell to a metal complex of Formula (I) as described above. In one embodiment the kinase is a receptor tyrosine kinase. In a specific embodiment the receptor tyrosine kinase is epidermal growth factor receptor (EGFR). In another specific embodiment the kinase is selected from the group consisting of ERK, PI3K, Akt, GSK3 and JNK.

A common feature of the methods and uses as outlined above is the use of a metal complex of formula (I). In one embodiment of the aspects described above the metal complex is sufficiently stable that upon administration to the subject the metal is not released in the extracellular environment but rather is released in the cells of the subject. This is preferable as it ensures that the metal is delivered to the cells of the subject rather than being released prior to delivery to the cells. In embodiments where the metal is released from the complex in the cell it is therefore present in the cell as the free cation and it is the free cation that is responsible for the biological activity in the subject. In another embodiment the metal complex does not release the metal in the extracellular matrix nor does it release the metal in the cell rather it is the metal complex that leads to the observed biological activity. Modifications to the metal complex either through changes in the nature of the metal or changes in the nature of the ligand may be made to obtain the desired delivery of the metal to the cells of the subject.

In one embodiment of the complex used in the aspects of the invention described above the metal is selected from the group consisting of Iron, Nickel, Palladium, Cadmium, Manganese, Cobalt, Copper and Zinc. In another embodiment the metal is Copper or Zinc. In one specific embodiment the metal is Copper. In another specific embodiment the metal is Zinc.

In one embodiment of the complex used in the aspects of the invention described above the complex is symmetrical. In another embodiment of the complex used in the aspects of the invention described above the complex is asymmetrical.

In one embodiment of the complex used in the aspects of the invention described above $R^1$ is selected from the group consisting of H, alkyl and aryl, each of which may be substituted. In another embodiment $R^1$ is selected from the group consisting of H, methyl, ethyl and phenyl. In one specific embodiment $R^1$ is H.

In one embodiment of the complex used in the aspects of the invention described above $R^2$ is selected from the group consisting of H, alkyl, aryl, and —(CH$_2$)$_m$R$^8$, each of which may be optionally substituted. In one embodiment m is 1 or 2. In one embodiment R$^8$ is aryl or heterocycloalkyl, each of which may be optionally substituted. In a specific embodiment R$^8$ is phenyl, or morpholin-4-yl. In further specific embodiment R$^2$ is selected from the group consisting of H, methyl, ethyl, phenyl-methyl, 2-morpholin-4-yl-ethyl, phenyl, 4-chloro-phenyl and 4-methoxy-phenyl.

In one embodiment of the complex used in the aspects of the invention described above R$^3$ is selected from the group consisting of H, methyl, ethyl and phenyl. In one specific embodiment R$^3$ is H. In another specific embodiment R$^3$ is methyl.

In one embodiment of the complex used in the aspects of the invention described above R$^4$ is selected from the group consisting of H, methyl, ethyl and phenyl. In one specific embodiment R$^4$ is H. In another specific embodiment R$^4$ is methyl.

In one embodiment of the complex used in the aspects of the invention described above R$^3$ and R$^4$, when taken together with the carbon atoms to which they are attached form an optionally substituted cycloalkyl group. In one specific embodiment the cycloalkyl group is a cyclohexyl group. In another specific embodiment of the complex used in the invention R$^3$ and R$^4$ are both H.

In one embodiment of the complex used in the aspects of the invention described above R$^5$ is selected from the group consisting of H, alkyl and aryl, each of which may be substituted. In another embodiment R$^5$ is selected from the group consisting of H, methyl, ethyl and phenyl. In one specific embodiment R$^5$ is H.

In one embodiment of the complex used in the aspects of the invention described above R$^6$ is selected from the group consisting of H, alkyl, aryl, and —(CH$_2$)$_m$R$^8$, each of which may be optionally substituted. In one embodiment m is 1 or 2. In one embodiment R$^8$ is aryl or heterocycloalkyl, each of which may be optionally substituted. In a specific embodiment R$^8$ is phenyl, or morpholin-4-yl. In further specific embodiment R$^6$ is selected from the group consisting of H, methyl, ethyl, phenyl-methyl, 2-morpholin-4-yl-ethyl, phenyl, 4-chloro-phenyl and 4-methoxy-phenyl.

In one preferred embodiment of the complex used in the aspects of the invention described above the metal complex increases phosphoinositol-3-kinase (PI3K)-Akt activity in the subject. In another preferred embodiment the metal complex decreases glycogen synthase kinase 3 (GSK3) activity in the subject. In another preferred embodiment the metal complex increases JNK activity in the subject. In another embodiment of the invention the metal complex leads to activation of one or more anti-oxidant enzymes. In one embodiment the anti-oxidant enzyme is superoxide dismutase (SOD).

Specific examples of complexes that are useful in the methods of the invention include the following:

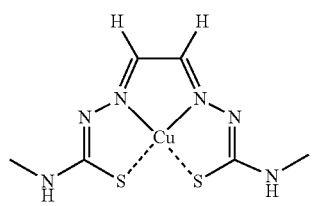

-continued

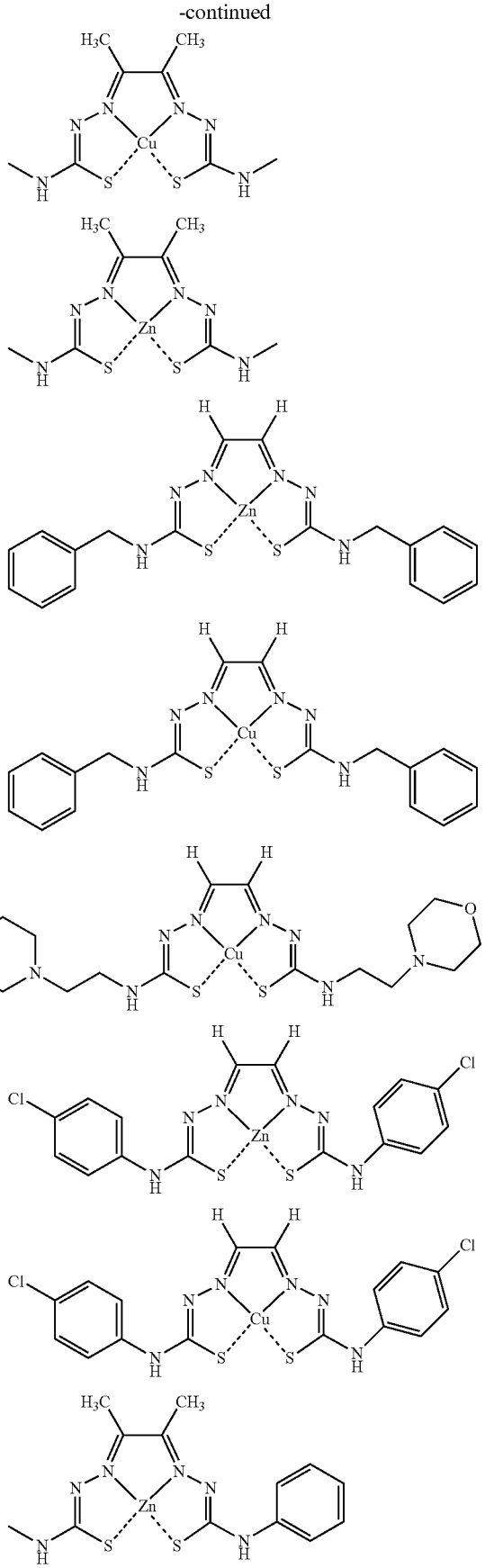

-continued
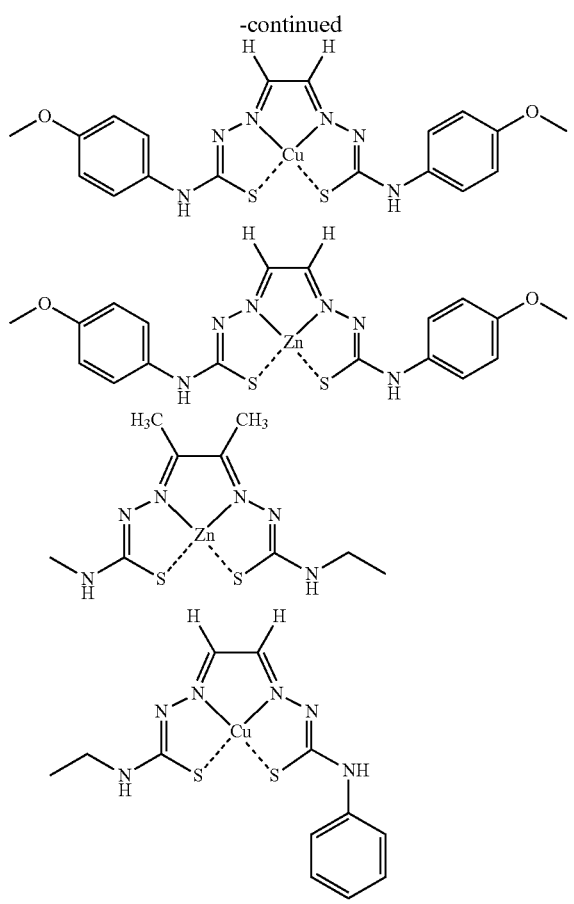
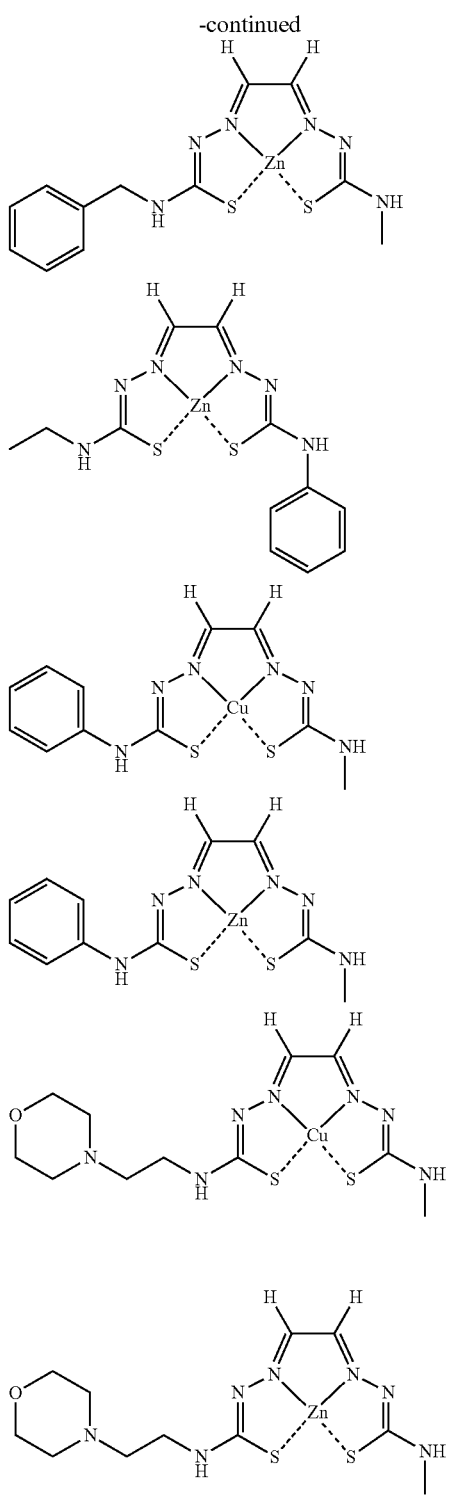

-continued

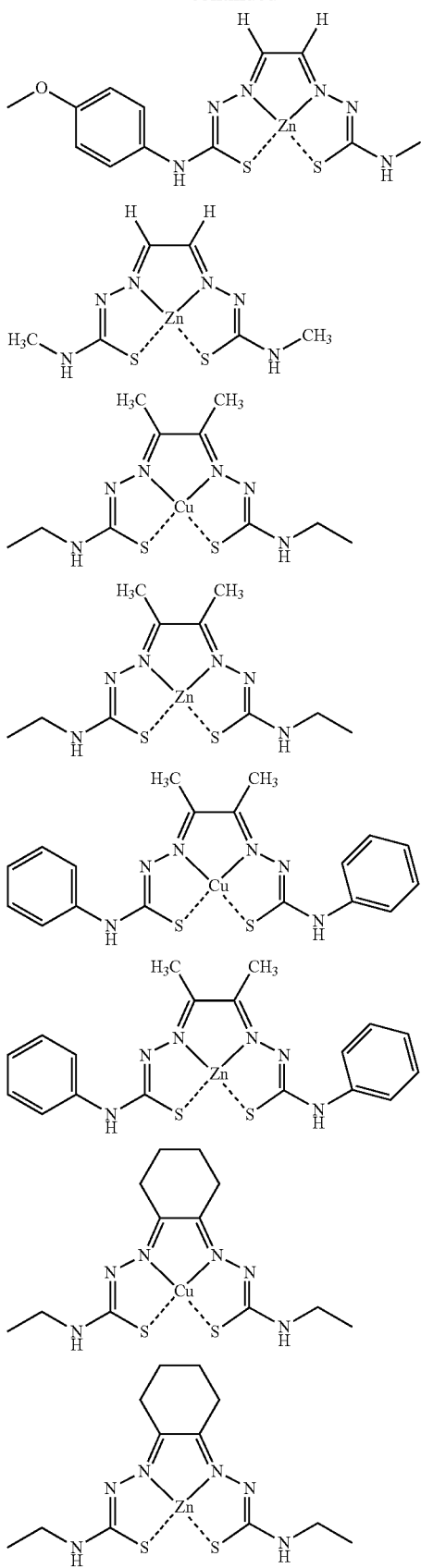

BRIEF DESCRIPTION OF THE FIGURES

FIG. 8D: illustrates that inhibition of amyloid βeta in cultures by Zn-BTSC is dependent on activation of JNK and phosphoinositol-3-kinase. Inhibition of JNK by SP600125 prevents the loss of amyloid βeta. Inhibition of phosphoinositol-3-kinase by LY294002 prevents loss of amyloid βeta. SB203580 (p38 inhibitor) has no effect).

DETAILED DESCRIPTION OF THE INVENTION

Figure 1:
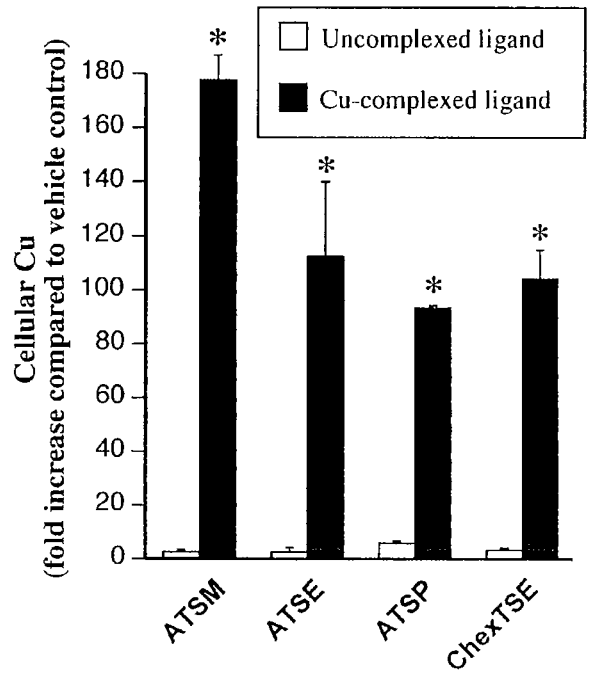
FIG. 1: illustrates cellular copper levels when cells were treated with a variety of free ligand and copper ligand complexes.

In this specification a number of terms are used which are well known to a skilled addressee. Nevertheless for the purposes of clarity a number of terms will be defined.

As used herein, the term "unsubstituted" means that there is no substituent or that the only substituents are hydrogen.

The term "optionally substituted" as used throughout the specification denotes that the group may or may not be further substituted or fused (so as to form a condensed polycyclic system), with one or more substituent groups. Preferably the substituent groups are one or more groups independently selected from the group consisting of halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkoxy, alkoxyalkyl, alkoxycycloalkyl, alkoxyheterocycloalkyl, alkoxyaryl, alkoxyheteroaryl, alkoxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, arylalkyl, heteroarylalkyl, cycloalkylalkyl, heterocycloalkylalkyl, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —COOH, —COR$^9$, —C(O)OR$^9$, —CONHR$^9$, —CSNHR$^9$, —NHCOR$^9$, —NHCOOR$^9$, NHCONHR$^9$, C(=NOH)R$^9$, —SH, —SR$^9$, —OR$^9$, acyl, a group of formula —NR$^9$R$^{10}$ or a group of formula —CONR$^9$R$^{10}$ or a group of formula —NHCONR$^9$R$^{10}$ wherein R$^{10}$ is a protein, hormone, antibody or carbohydrate moiety.

"Alkyl" as a group or part of a group refers to a straight or branched aliphatic hydrocarbon group, preferably a C$_1$-C$_{14}$ alkyl, more preferably C$_1$-C$_{10}$ alkyl, most preferably C$_1$-C$_6$ unless otherwise noted. Examples of suitable straight and branched C$_1$-C$_6$ alkyl substituents include methyl, ethyl, n-propyl, 2-propyl, n-butyl, sec-butyl, t-butyl, hexyl, and the like. When alkyl is used as a bridging group it is typically (but not exclusively) referred to as alkylene. A similar convention applies to other bridging groups.

"Acyl" means an alkyl-CO— group in which the alkyl group is as described herein. Examples of acyl include acetyl and benzoyl. The alkyl group is preferably a C$_1$-C$_6$ alkyl group.

"Alkenyl" as a group or part of a group denotes an aliphatic hydrocarbon group containing at least one carbon-carbon double bond and which may be straight or branched preferably having 2-14 carbon atoms, more preferably 2-12 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl.

"Alkoxy" refers to an —O-alkyl group in which alkyl is defined herein. Preferably the alkoxy is a C$_1$-C$_6$alkoxy. Examples include, but are not limited to, methoxy and ethoxy.

"Alkynyl" as a group or part of a group means an aliphatic hydrocarbon group containing a carbon-carbon triple bond and which may be straight or branched preferably having from 2-14 carbon atoms, more preferably 2-12 carbon atoms, more preferably 2-6 carbon atoms in the normal chain. Exemplary structures include, but are not limited to, ethynyl and propynyl.

"Cycloalkyl" refers to a saturated or partially saturated, monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane.

"Heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4-oxathiapane.

"Heteroalkyl" refers to a straight- or branched-chain alkyl group preferably having from 2 to 14 carbons, more preferably 2 to 10 atoms in the chain, one or more of which is a heteroatom selected from S, O, and N. Exemplary heteroalkyls include alkyl ethers, secondary and tertiary alkyl amines, alkyl sulfides, and the like.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a C$_{5-7}$ cycloalkyl or C$_{5-7}$ cycloalkenyl group are fused together to form a cyclic structure, such as tetrahydronaphthyl, indenyl or indanyl.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

Generally, the terms "treatment" and "prophylaxis" mean affecting a subject, tissue or cell to obtain a desired pharmacological and/or physiological effect and include: (a) preventing the condition from occurring in a subject that may be predisposed to the condition, but has not yet been diagnosed as having it; (b) inhibiting the condition, i.e., arresting its development; or (c) relieving or ameliorating the effects of the condition, i.e., cause regression of the effects of the condition.

The term "subject" as used herein refers to any animal having a disease or condition which requires treatment or prophylaxis with a biologically-active agent. The subject may be a mammal, typically a human, or may be a non-human primate or non-primates such as used in animal model testing. While it is particularly contemplated that the compounds are suitable for use in medical treatment of humans, it is also applicable to veterinary treatment, including treatment of companion animals such as dogs and cats, and domestic animals such as horses, ponies, donkeys, mules, llama, alpaca, pigs, cattle and sheep, or zoo animals such as primates, felids, canids, bovids and ungulates.

The Therapeutic Approach

The present invention is based on the observation that metal plays an important role in a wide number of biological processes and adequate metal levels are especially important in the efficient functioning of a wide range of biologically important enzymes and cellular signaling processes. Enzymes that involve metal activation include many of the enzymes related to oxidation at the cellular level. Accordingly it was felt that selective metal delivery to subjects with conditions relating to abnormal levels of metals could provide a useful therapeutic outcome for a number of biological applications. In particular it was felt that this could be useful in respect of conditions caused by or associated with oxidative stress as this is a condition where many of the protective mechanisms or enzymes that protect the body from oxidative stress involve metal catalysis and so the provision of bio-available metal may be a useful therapeutic in treating these conditions.

As such, investigations were based on identifying appropriate metal complexes that would be able to deliver metal to sites wherein metal is depleted in a subject. Investigations were particularly based on complexes that would be able to deliver metal to the cells of a subject. A number of important biological processes that are mediated by metal, such as metal mediated enzymes, occur in the cells rather than in the extra-cellular matrix. The present applicants therefore decided that it was preferable that the metal be delivered in the form of cell permeable metal complex in order to ensure that the metal acted on the cell rather than in the extra-cellular environment. In addition, it was found that in order to ensure that the metal was delivered to the cell it was preferable that the cell permeable metal complex be sufficiently stable such that upon administration to a subject the metal is not released in the extra-cellular environment. A further advantage of the use of metal complexes over the "naked" metal ion is that delivery of the metal can be targeted which reduces the chance that unwanted side effects will be observed (for example copper toxicity). A number of metal complexes meet these criteria.

One attractive group of metal complexes for use in the methods of the present invention are metal complexes of bis(thiosemicarbazone) (BTSC) ligands which have been investigated as metallodrugs and have proven to have a broad range of pharmacological activity. In particular, recent interest has focused on the use of BTSC ligands as vehicles for the selective delivery of radioactive copper isotopes to hypoxic tissue and leucocytes in the development of radiopharmaceuticals. Copper(II)-BTSC complexes are stable (log $K=10^{18}$) neutral, low molecular weight complexes capable of crossing cell membranes. In some cases, once inside cells the copper(II) is reduced by intracellular reductants to Cu(I) which subsequently dissociates from the ligand. Other Cu(II)-BTSC complexes are more resistant to reduction and disassociation, and are only trapped in hypoxic cells. This selectivity is remarkably sensitive to the number of alkyl groups attached to the diimine backbone of the ligand. For example, copper(II)diacetylbis(N(4)-methylthiosemicarbazone) [Cu(ATSM)] with two methyl substituents on the backbone, is selective for hypoxic cells whereas the copper of [Cu(GTSM)] is trapped in all cells. The hypoxic cell selectivity has been correlated with the Cu(II)/Cu(I) reduction potential, [Cu(ATSM)] is some 160 mV harder to reduce than [Cu(GTSM)], but differences in pKa and the stability of the reduced state may also be important.

[Zinc(BTSC)] complexes are also capable of transporting zinc into cells and a recent report used the intrinsic fluorescence of certain [Zn(BTSC)] complexes to probe the intracellular distribution of the complexes via fluorescence microscopy in several cancer-cell lines. Sub-cellular localization was a sensitive function of terminal nitrogen substituents on the complexes and cell type, varying from predominantly nucleolar to lysosomal. Zinc is central to a number of cell signal pathways including modulation of NMDA receptor activity expression of metallothienein and activation of mitogen activated protein kinase (MAPK)-mediated signal transduction pathways and therefore, Zn-BTSC uptake could have complex effects on downstream metal-mediated cell signalling.

It was therefore felt that BTSC metal complexes of this type were attractive as potential cell permeable metal complexes for use in the methods of the invention. BTSC-metal complexes have several properties that make them worthy of investigation as potential therapeutic agents for the treatment of conditions related to oxidative stress including neurodegenerative disorders such as Alzheimer's disease. Organ and tissue distribution of these types of materials are well characterized, several BTSC complexes are known to be capable of crossing the blood brain barrier and there is no inherent class toxicity with these complexes. Importantly, the ligands can be readily modified by varying the nature and number of alkyl substituents on the ligand and these modifications can allow subtle control of subcellular targeting and metal release/retention properties.

In addition, the complexes are attractive as different metal complexes have different modes of metal release in the cell, potentially opening the way for the selective use of different metal complexes for different applications. For example, the zinc and copper complexes increase the bio-available metal via different mechanisms.

Without wishing to be bound by theory it is felt that in the case of the zinc complexes the associations constants have been measured to be of the order of $10^{7-8}$. As such, these cell permeable complexes are stable enough to effectively enter the cell as they are sufficiently stable in the extracellular matrix. Once inside the cell it is thought that the zinc is released from the ligand due to an increased competition from intracellular ligands (and perhaps decreased [$Zn^{2+}$]). This therefore ultimately leads to bio-available metal in the cell.

In contrast, it is felt that copper complexes release their metal via a different mechanism. The stability constants of copper BSTC complexes have been measured to be of the order of $10^{18}$. Both [Cu(ATSM)] and [Cu(GTSM)] have similar stability constants for Cu(II). Where they differ is in their reduction potentials. For [Cu(ATSM)] $E_{1/2}=-0.59$ V whereas for [Cu(GTSM)] $E_{1/2}=0.43$V, this means it is easier to reduce Cu(II) to Cu(I) in [Cu(GTSM)]. This results from the modification of the backbone of the ligand ($R^3$ and $R^4$). The methyl groups of ATSM are electron donating and make it harder to reduce to Cu(I). Once [Cu(GTSM)] enters the cell it is reduced to Cu(I) via cell reducing agents. The Cu(I) complex is less stable than the Cu(II) complex and the metal disassociates from the ligand making the copper bio-available as either (Cu(I) or Cu(II)). In the case of [Cu(II)ATSM] the copper is not released due to its increased resistance to reduction and trans-metallation. In addition complexes of this type were attractive as not only do they have different mechanisms of metal release depending upon the metal ion chosen some of the complexes are such that they do not release the metal at all and so they may be used in circumstances where it is desirable not to deliver the metal in the form of a metal cation but rather it is desirable to deliver the metal in the form of a bound metal still in complex with the ligand.

A number of metal complexes of this type were therefore initially synthesised to examine their behavior.

The ligands and complexes selected for the initial study were as follows:

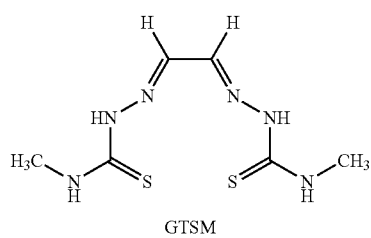

GTSM

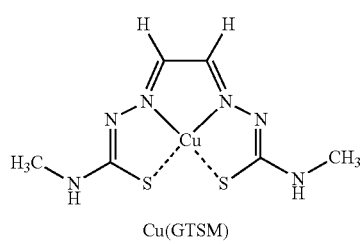

Cu(GTSM)

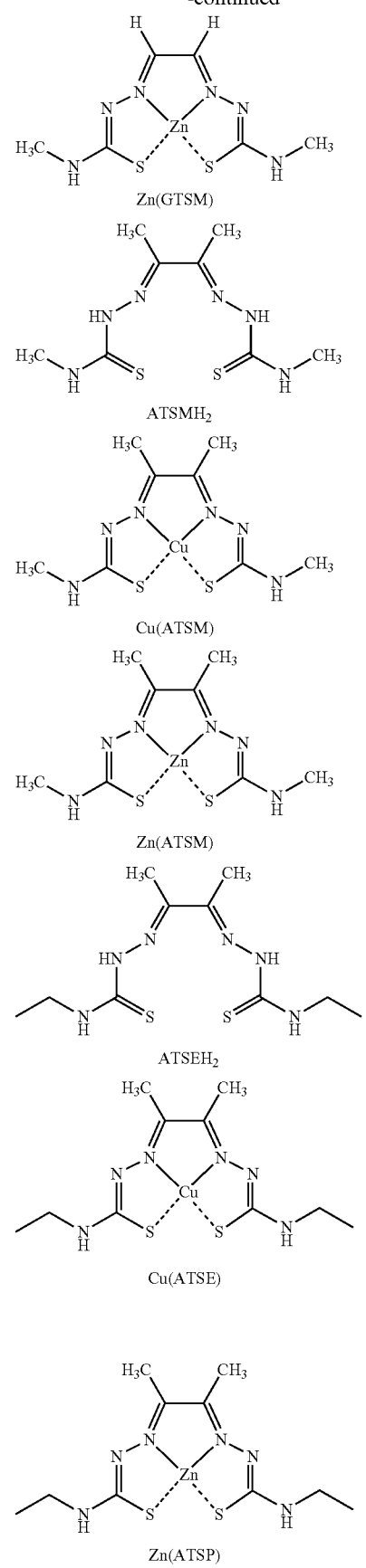

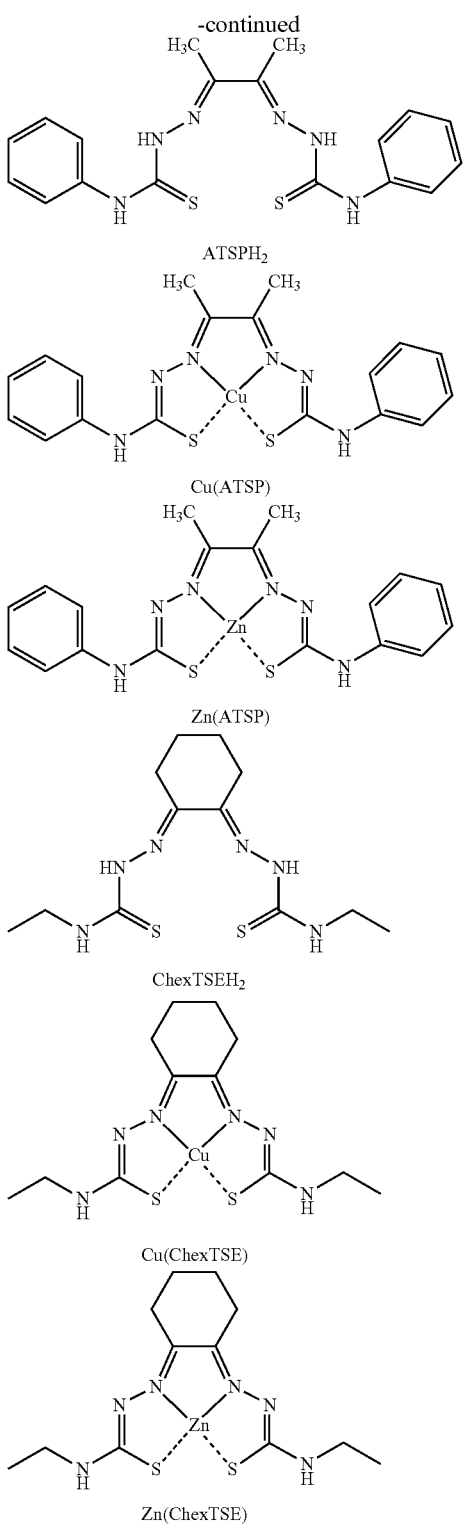

ATSPH₂

Cu(ATSP)

Zn(ATSP)

ChexTSEH₂

Cu(ChexTSE)

Zn(ChexTSE)

Biological Activity

Cellular Metal Uptake

It was found that treatment of APP-transfected Chinese Hamster Ovary (APP-CHO) cells with both Cu (BTSC) and Zn (BTSC) increased cellular metal levels demonstrating uptake of the BTSC-metal complexes. This supports the proposition that the complexes are sufficiently stable in the extracellular matrix to allow the metal to be delivered to the cell. As such, it was possible to demonstrate that complexes of this type were candidate complexes that could be used to deliver metal to the cell without the risk of releasing the metal from the complex in the extracellular matrix leading to the adverse affects noted by others who have taught that metals such as zinc should be reduced in the extracellular matrix.

Treatment of (APP-CHO) cells with a range of [Cu (BTSC] complexes with dialkyl backbones at 1-50 µM for 6 hr resulted in significant increases in intracellular copper levels when compared to treatment with free ligands or Copper alone and the results are shown in FIG. 1. This suggests that the complex is important in the transportation of the metal across the cell membrane. The highest levels of copper were induced by treatment with [Cu(ATSM)] which resulted in a 177±9 fold increase in cellular copper levels when compared to untreated control cells. This corresponded to a cellular Copper level of 4.5 ng/mg protein and 796 ng/mg protein for control and [Cu(ATSM)] treated cells respectively. The other three [Cu(BTSC)] complexes resulted in 90-115 fold increases in cellular copper levels.

Figure 2:
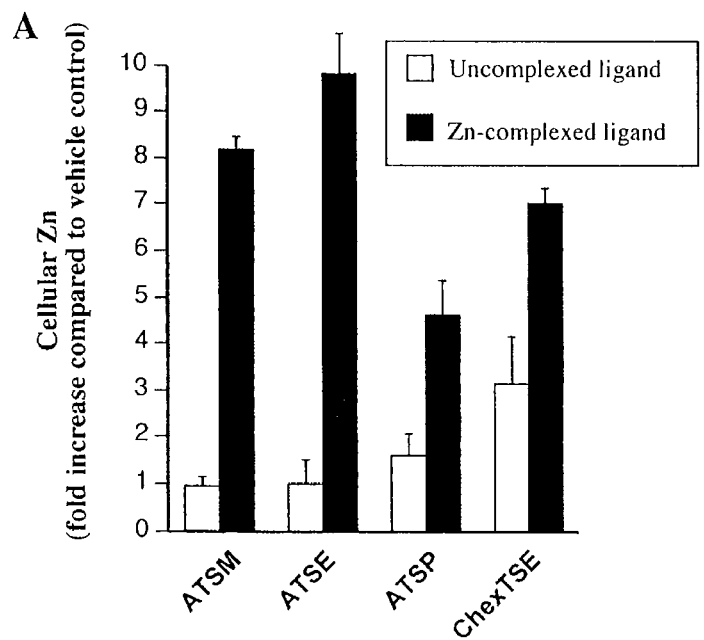
FIG. 2: illustrates cellular zinc levels when cells were treated with a variety of free ligand and zinc ligand complexes.
Figure 3:
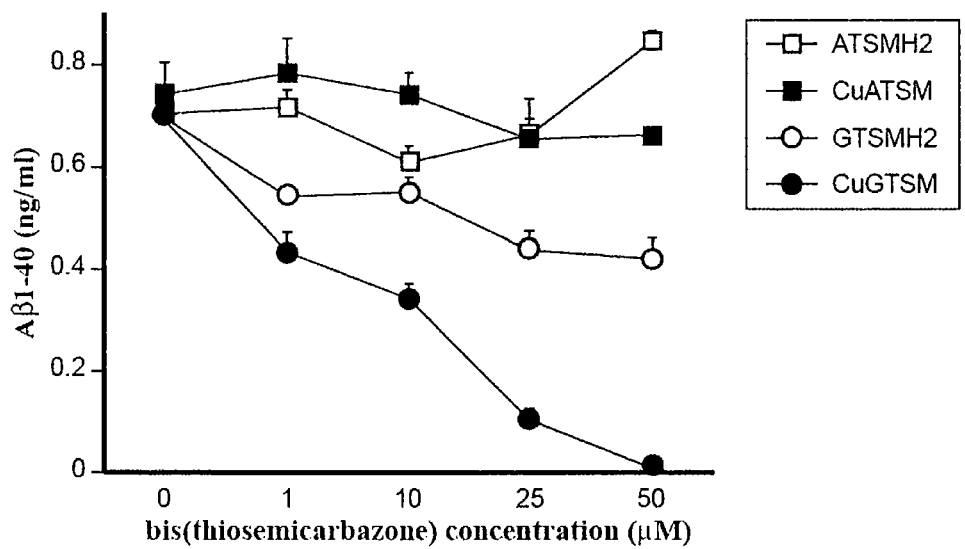
FIG. 3: illustrates the different effect of Cu-GTSM versus Cu-ATSM on extracellular amyloid βeta levels.

Zn-BTSC complexes are less stable than their copper complexes (related derivatives having association constants of the order of log K=7 but are still capable of effectively transporting Zinc into the cell. Treatment of cells with [Zn(BTSC)] complexes resulted in significant increases in the intracellular Zinc levels as measured by ICP-MS (FIG. 2.). [Zn(ATSM)] and [Zn(ATSE)] induced 8.2±0.25 and 9.8±0.9 fold increases in cellular Zinc levels respectively (FIG. 2). The data obtained suggested that the complexes were capable of delivering metals to cells and so attention was turned to probing a number of biological systems where it was envisaged that metal delivery could be useful Reduction in Extracellular Amyloid Beta Levels Treatment of APP-CHO cells with [Cu(GTSM)] resulted in an increase in the intracellular copper levels as expected of the cell permeable Cu-ligand. There also was a dose-dependent reduction in the extracellular levels of Aβ1-40 (amyloid βeta). The concentration of Aβ1-40 was 0.70 ng mL$^{-1}$ in untreated cells. Treatment with 1 µM [Cu(GTSM)] reduced this to 0.43 ng mL$^{-1}$ (FIG. 3). Aβ1-40 levels were further reduced to negligible levels following treatment with 50 µM [Cu(GTSM)]. The very small reduction in the levels of Aβ1-40 that were evident following administration of the ligand (GTSMH₂) to the cells was most likely due to the formation of either [Cu(GTSM)] or [Zn(ATSM)] from trace metals in the culture medium.

Figure 4:
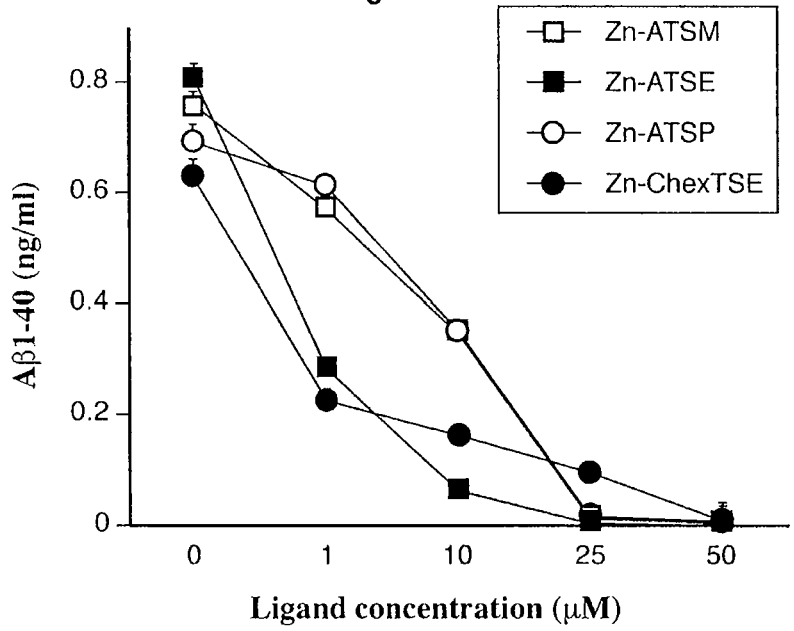
FIG. 4: illustrates the effect of various zinc complexes on extracellular amyloid βeta levels

The lower stability of the Zn-BTSC complexes means they are more susceptible to intracellular transchelation than their Copper analogues and therefore, could elevate levels of bio-available Zinc within the cells. The elevated Zinc levels in the cells treated with [Zn(BTSC)] complexes correlated with a reduction in the extracellular levels of Aβ1-40. The concentration of Aβ1-40 in the medium of untreated cells was 0.6-0.8 ng mL$^{-1}$ and was reduced to less than 0.2 ng mL$^{-1}$ following treatment with 25 µM [Zn(BTSC)]. The different [Zn(BTSC)] complexes exhibited some detectable differences in the dose dependent reduction of Aβ1-40. Treatment with [Zn(ATSE)] and [Zn(ChexTSE)] resulted in greater reductions at a lower dose (1 µM) when compared to the other two complexes, [Zn(ATSM)] and [Zn(ATSP)]) (FIG. 4). This could reflect different binding affinities or alternative subcellular localisation and subsequently initiate different metal-mediated cell signalling pathways. The results clearly demonstrated that the zinc complexes were highly effective in reducing the extra-cellular concentration of amyloid βeta.

Treatment of Cells with Zinc Complexes in the Presence of Copper

Figure 5:
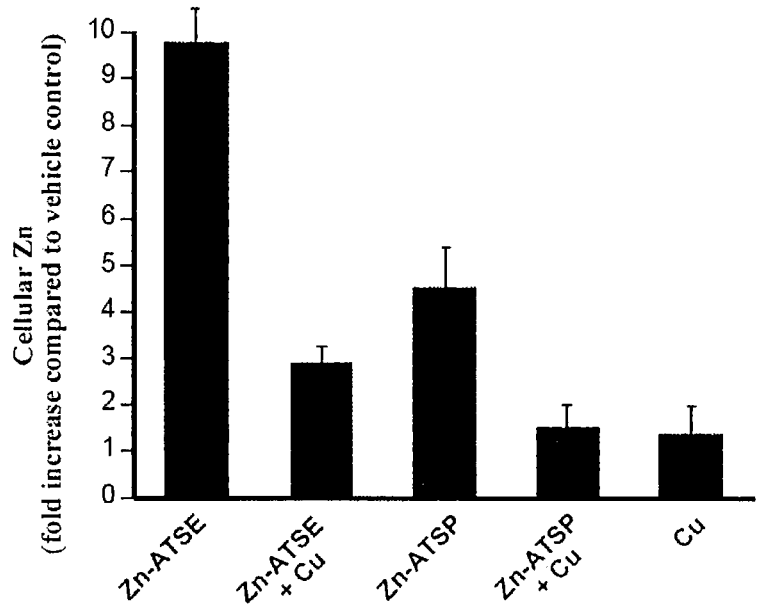
FIG. 5: illustrates how Copper inhibits uptake of Zinc in cells treated with Zn-BSTC and inhibits effect of Zn-BTSC on amyloid βeta.

It was known that copper can transmetallate [Zn(BTSC)] complexes. Therefore, if [Zn(BTSC)] complexes were administered to the culture medium in the presence of exogenous $Cu^{2+}$, we would expect [Cu(BTSC)] complexes to form. To examine this, cells were exposed to 10 μM [Zn(ATSE)] or [Zn(ATSP)] with or without 5-50 μM $Cu^{2+}$ for 6 hr. Treatment of cells with 10 μM [Zn(ATSE)] alone resulted in a 9.7±0.7 fold increase the cellular zinc levels compared to untreated cultures (FIG. 5). In comparison, treatment with 10 μM [Zn(ATSE)] in the presence of 10 μM $Cu^{2+}$ only resulted in a 2.9±0.3 fold increase in intracellular zinc (FIG. 5). Similar effects were seen for [Zn(ATSP)] in the presence of $Cu^{2+}$. These data strongly suggest that transmetallation of a proportion of the zinc complexes to give the analogous $Cu^{2+}$ complexes diminished the amount of zinc transported into the cell.

Effect of Temperature of Metal Uptake

Figure 6:
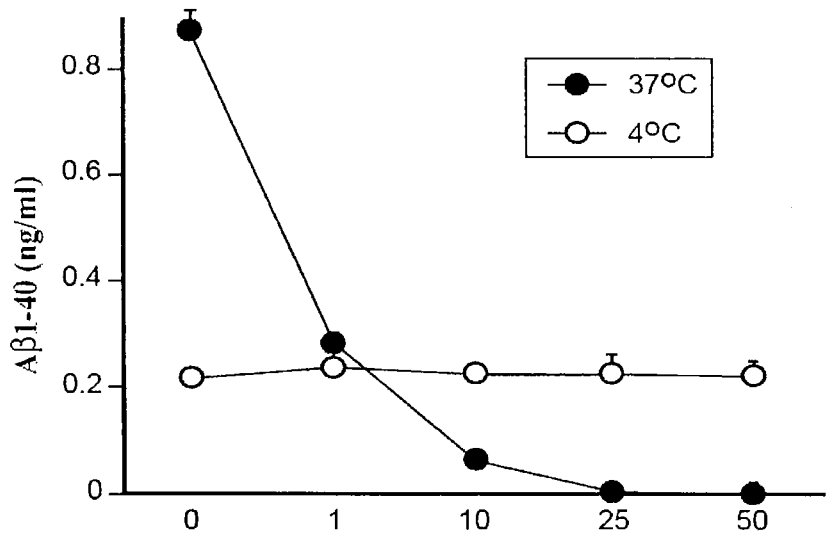
FIG. 6: illustrates the effect of temperature on metal uptake.
Figure 7:
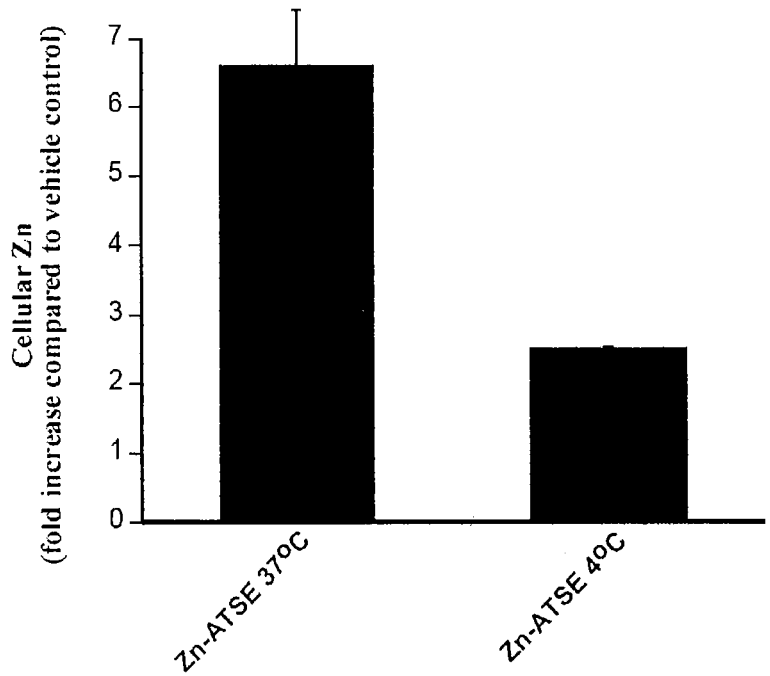
FIG. 7: illustrates the effect of temperature effect on BTSC—amyloid βeta and metal uptake.

A study was conducted in which cells were exposed to differing concentrations of one of the complexes of the invention at a number of various concentrations and at either 4 or 37° C. The results as shown in FIGS. 6 and 7 which clearly indicate that cellular uptake is dependent upon temperature and can have a significant effect upon the level of amyloid βeta. Treatment of cells at 37° C. results in a high level of metal uptake which results in loss of extracellular Amyloid βeta. Incubation of cells at 4° C. results in substantially lower metal uptake and therefore, reduced effects on extracellular Amyloid βeta. The results indicate that metal uptake is therefore likely to be an active, rather than passive process and could provide the opportunity to target specific metal-BTSC receptors to improve efficacy of the complexes.

As the initial complexes showed promise a number of additional complexes were synthesized in order to probe the activity of the family of complexes. These complexes were synthesized and then subjected to in vivo mouse assays to determine a number of biological properties of the complexes.

Investigation of Biological Pathways

Figure 8A:
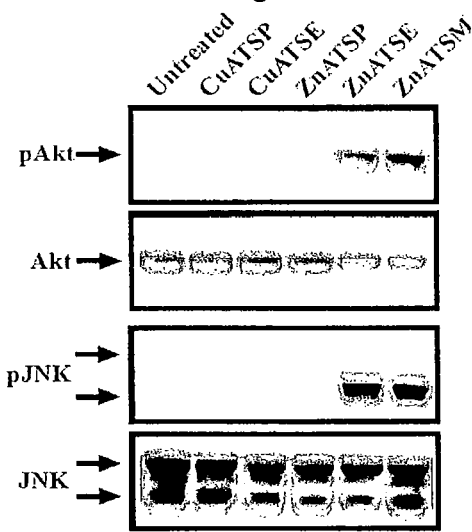
FIG. 8A: illustrates that ZnBTSC induces activation of phosphoinositol-3-kinase (phosphorylation of Akt, p-Akt) and activates JNK (resulting in JNK phosphorylation, p-JNK).

With the results clearly indicating that there was metal uptake in the cells an investigation was conducted to determine the relevant pathways leading to the observed result. APP-CHO cells were treated with 10 μM metal-BTSC complexes for 6 hr and cell lysates examined for activation of PI3K and MAPK signal pathways. CuATSP and CuATSE did not induce activation of PI3K (Akt phosphorylation) or JNK (FIG. 8A). In contrast, [Zn(ATSE)] and [Zn(ATSM)] both induced activated Akt and JNK (FIG. 8A). Activation of PI3K-Akt by [Zn(ATSE)] also induced down-stream phosphorylation (de-activation) of GSK3 as well as increased GSK3 expression (FIG. 8B).

Figure 8B:
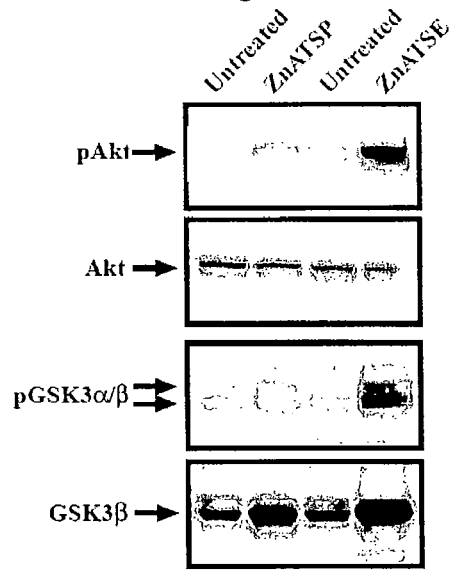
FIG. 8B: illustrates that ZnATSE inhibits activation of GSK3 by inducing its phosphorylation (p-GSK3).
Figure 8C:
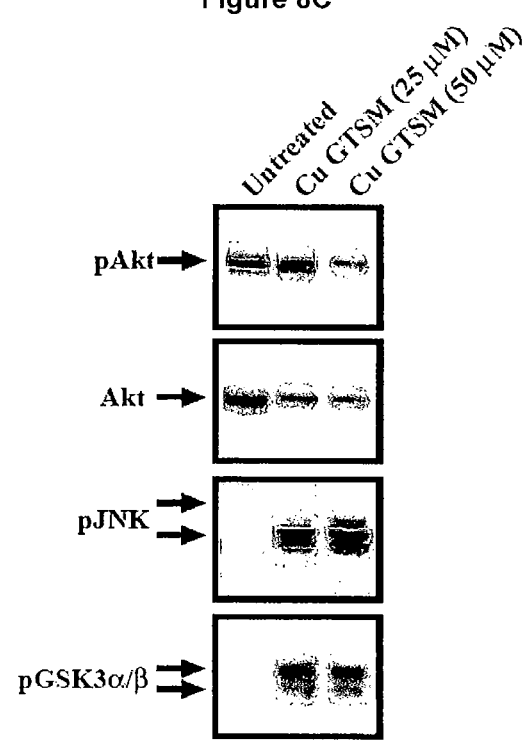
FIG. 8C: illustrates that Cu-GTSM induces activation of phosphoinositol-3-kinase (phosphorylation of Akt, p-Akt), activation of JNK (p-JNK) and inhibition of GSK3 (p-GSK3).

Interestingly, [Zn(ATSP)] did not induce activation of Akt or JNK (FIG. 8A), although a small increase in GSK3 expression was observed (FIG. 8B).

Methods of Treatment, Amelioration and/or Prophylaxis

The complexes of the invention have been shown to be effective as metal delivery agents, particularly agents for the delivery of metals to cells. According the complexes of the invention may be used in the treatment or prophylaxis of a number of conditions in which metal delivery can prevent, alleviate or ameliorate the condition.

There are a number of conditions of this type. An example of conditions of this type is conditions associated with or caused by oxidative stress. It is known that many of the protective biological anti-oxidant mechanisms involve metal catalysed enzymes and thus metal delivery can serve to stimulate or re-start the activity of the biological anti-oxidant mechanisms leading to an overall anti-oxidant effect being achieved. In one embodiment the condition associated with or caused by oxidative stress is selected from the group consisting of cardiovascular conditions, cancers, cataracts, neurological disorders such as Alzheimer's disease, prion diseases—including Creutzfeldt-Jakob Disease (CJD), and heart diseases, amyloidogenic amylotrophic lateral sclerosis (ALS), prion transmissible spongioform encephalopathies (TSE), cataracts, mitochondrial disorders, Menke's disease, Parkinson's disease and Huntington's disease.

In another embodiment the disorder is a neuromuscular disorder selected from the group consisting of amyotrophic lateral sclerosis (ALS), mitochondrial/metabolic disease and Friedreich's ataxia.

In one embodiment of the invention the condition is a neurological condition or a neurodegenerative disorder.

The term "neurological condition" is used herein in its broadest sense and refers to conditions in which various cell types of the nervous system are degenerated and/or have been damaged as a result of neurodegenerative disorders or injuries or exposures. In particular, complexes of formula (I) can be used for the treatment of resulting conditions, in which damage to cells of the nervous system has occurred due to surgical interventions, infections, exposure to toxic agents, tumours, nutritional deficits or metabolic disorders. In addition, the complex of formula (I) can be used for the treatment of the sequelae of neurodegenerative disorders, such as Alzheimer's disease, Parkinson's disease, multiple sclerosis, amylotrophic lateral sclerosis, epilepsy, drug abuse or drug addiction (alcohol, cocaine, heroin, amphetamine or the like), spinal cord disorders, dystrophy or degeneration of the neural retina (retinopathies) and peripheral neuropathies, such as diabetic neuropathy and/or the peripheral neuropathies induced by toxins.

The term "neurodegenerative disorder" as used herein refers to an abnormality in which neuronal integrity is threatened. Neuronal integrity can be threatened when neuronal cells display decreased survival or when the neurons can no longer propagate a signal.

Neurological conditions that can be treated with the complexes of the present invention include acute intermittent porphyria; adriamycin-induced cardiomyopathy; AIDS dementia and HIV-1 induced neurotoxicity; AD; ALS; atherosclerosis; cataract; cerebral ischaemia; cerebral palsy; cerebral tumour; chemotherapy-induced organ damage; cisplatin-induced nephrotoxicity; coronary artery bypass surgery; CJD and its new variant associated with "mad cow" disease; diabetic neuropathy; Down's syndrome; drowning; epilepsy and post-traumatic epilepsy; Friedrich's ataxia; frontotemporal dementia; glaucoma; glomerulopathy; haemochromatosis; haemodialysis; haemolysis; haemolytic uraemic syndrome (Weil's disease); Menke's disease; haemorrhagic stroke; Hallerboden-Spatz disease; heart attack and reperfusion injury; HD; Lewy body disease; intermittent claudication; ischaemic stroke; inflammatory bowel disease; macular degeneration; malaria; methanol-induced toxicity; meningitis (aseptic and tuberculous); motor neuron disease; multiple sclerosis; multiple system atrophy; myocardial ischaemia; neoplasia; Parkinson's disease; peri-natal asphyxia; Pick's disease; progressive supra-nuclear palsy; radiotherapy-induced organ damage; restenosis after angioplasty; retinopathy; senile dementia; schizophrenia; sepsis; septic shock; spongiform encephalopathies; subharrachnoid haemorrage/cerebral vasospasm; subdural haematoma; surgical trauma, including neurosurgery; thalassemia; transient ischaemic attack (TIA); transplantation; vascular dementia; viral meningitis; and viral encephalitis.

Additionally, the complexes of the present invention may also be used to potentiate the effects of other treatments, for example to potentiate the neuroprotective effects of brain derived nerve growth factor.

The complexes of the invention may also be used to treat Anemia, Neutropenia, Copper deficiency Myelopathy, Copper deficiency Syndrome and Hyperzincaemia.

The invention is particularly directed to conditions which induce oxidative damage of the central nervous system, including acute and chronic neurological disorders such as, cerebral ischaemia, stroke (ischaemic and haemorragic), subharrachnoid haemorrage/cerebral vasospasm, cerebral tumour, AD, CJD and its new variant associated with "mad cow" disease, HD, PD, Friedrich's ataxia, cataract, dementia with Lewy body formation, multiple system atrophy, Hallerboden-Spatz disease, diffuse Lewy body disease, amylotrophic lateral sclerosis, motor neuron disease, multiple sclerosis, fatal familial insomnia, Gertsmann Straussler Sheinker disease and hereditary cerebral haemorrhage with amyoidoisis-Dutch type.

More particularly, the invention is directed to the treatment of neurodegenerative amyloidosis. The neurodegenerative amyloidosis may be any condition in which neurological damage results from the deposition of amyloid. The amyloid may be formed from a variety of protein or polypeptide precursors, including but not limited to Aβ, synuclein, huntingtin, or prion protein.

Thus the condition in one embodiment is selected from the group consisting of sporadic or familial AD, ALS, motor neuron disease, cataract, PD, Creutzfeldt-Jacob disease and its new variant associated with "mad cow" disease, HD, dementia with Lewy body formation, multiple system atrophy, Hallerboden-Spatz disease, and diffuse Lewy body disease.

In one specific embodiment the neurodegenerative amyloidosis is an Aβ-related condition, such as AD or dementia associated with Down syndrome or one of several forms of autosomal dominant forms of familial AD (reviewed in St George-Hyslop, 2000). Most preferably the Aβ-related condition is AD.

In a specific aspect of the invention, prior to treatment the subject has moderately or severely impaired cognitive function, as assessed by the AD Assessment Scale (ADAS)-cog test, for example an ADAS-cog value of 25 or greater.

In addition to slowing or arresting the cognitive decline of a subject, the complex and methods of the invention may also be suitable for use in the treatment or prevention of neurodegenerative conditions, or may be suitable for use in alleviating the symptoms of neurodegenerative conditions. If administered to a subject who has been identified as having an increased risk of a predisposition to neurodegenerative conditions, or to a subject exhibiting pre-clinical manifestations of cognitive decline, such as Mild Cognitive Impairment or minimal progressive cognitive impairment, these methods and compounds may be able to prevent or delay the onset of clinical symptoms, in addition to the effect of slowing or reducing the rate of cognitive decline.

Currently AD and other dementias are usually not diagnosed until one or more warning symptoms have appeared. These symptoms constitute a syndrome known as Mild Cognitive Impairment (MCI), which was recently defined by the American Academy of Neurology, and refers to the clinical state of individuals who have memory impairment, but who are otherwise functioning well, and who do not meet clinical criteria for dementia (Petersen et al., 2001). Symptoms of MCI include:

(1) Memory loss which affects job skills
(2) Difficulty performing familiar tasks
(3) Problems with language
(4) Disorientation as to time and place (getting lost)
(5) Poor or decreased judgement
(6) Problems with abstract thinking
(7) Misplacing things
(8) Changes in mood or behaviour
(9) Changes in personality
(10) Loss of initiative.

MCI can be detected using conventional cognitive screening tests, such as the Mini Mental Status Exam, and the Memory Impairment Screen, and neuropsychological screening batteries.

Another condition that may be able to be treated by metal delivery is cancer. The term "cancer" describes any array of different diseases linked by cumulative multiple genetic mutations, which result in the activation of oncogenes and/or the inactivation of tumor suppressor genes and/or linked by uncontrolled cellular proliferation. The cause and source of these mutations differs between different cancers of human body organs.

The invention is particularly directed to brain cancer, which includes a brain tumor. A brain cancer or tumor may be a glioma or non-glioma brain tumor. The term "cancer" and "tumor" may be used interchangeably herein. "cancer" may include any one of the following states: glioma, adenoma, blastoma, carcinoma, sarcoma and inclusive of any one of Medulloblastoma, Ependymoma, Astrocytoma, Optical nerve glioma, Brain stem glioma, Oligodendroglioma, Gangliogliomas, Craniopharyngioma or Pineal Region Tumors. Reference to a "glioma" includes GMB, astrocytoma and anaplastic astrocytoma or related brain cancers.

The complexes of the present invention may also be able to be used to treat tau related disorders. Tau protein is an important protein as it is the protein expressed in the central nervous system and plays a critical role in the neuronal architecture by stabilizing intracellular microtubule network. Accordingly any impairment of the physiological role of the tau protein either by truncation, hyper-phosphorylation or by disturbing the balance between the six naturally occurring tau isoforms is detrimental to the subject and leads to the formation of neurofibrillary tangles (NFT), dystrophic neurites and neuropil threads. The major protein subunit of these structures is microtubule associated protein tau. The amount of NFT found in autopsies of AD patients correlates with clinical symptoms including intellectual decline. Accordingly tau protein plays a critical role in AD pathology. The recent discovery of cosegregation of specific mutations in the tau gene with the disease frontotemporal dementia with Parkinsonism linked to chromosome 17 (FTDP-17) has confirmed that certain abnormalities in the tau protein can be a primary cause of neurodegeneration and dementia in affected individuals.

Without wishing to be bound by theory it is felt that the activity of the complexes of the present invention to reduce levels of tau phosphorylation is as a result of their ability to deliver metal to cells and hence their anti-oxidant activity. It is felt that the ability of the complexes to act as anti-oxidants mean that they provide protection from OS which is desirable as OS can lead to hyper-phosphorylation of tau and cell dysfunction. As a consequence the ability of these complexes to deliver biologically important metals to cells allows them to function as anti-oxidants (especially where the oxidative stress is caused by metal deficiency) which in turn means the metal complexes may have the ability to prevent (or treat) tau-opathies.

There are a number of disorders or conditions that are recognized as being tau disorders or more colloquially Tauopathies. Disorders of this type include Richardson's syndrome, Progressive Supranuclear Palsy, Agryrophilic grain disease, corticobasal degeneration, Pick's disease, frontotemporar dementia linked with parkinsonism linked to chromosome 17 9FTDP-17), post-encephalitic parkinsonism (PEP), dementia pugilistica, Down's syndrome, Alzheimers disease, Familial British dementia, Familial Danish dementia, Parkinsons' disease, Parkinsons Disease complex of Guam (PDC), myotonic dystrophy, Hallevorden-Spatz disease, and Niemann-Pick type C.

The complexes may also be used in the treatment of an Abeta related disorder. A number of Abeta disorders are known including disorders selected from the group consisting of Parkinson's disease, Alzheimer's disease, Multiple sclerosis, Neuropathies, Huntington's disease, Prion disease, motor neurone disease, Amyotrophic lateral sclerosis (ALS), Menke's disease, and amyloidoses.

As the complexes of the invention have also been shown to be able to deliver metal to cells they have the ability to influence matrix metallo-proteinases (MMP's). Matrix metalloproteinases (MMPs) are a family of zinc- and calcium-dependent secreted or membrane anchored endopeptidases which play a number of important biological functions. MMPs are involved in many physiological processes but also take part in the pathophysiological mechanisms responsible for a wide range of diseases. Pathological expression and activation of MMPs are associated with cancer, atherosclerosis, stroke, arthritis, periodontal disease, multiple sclerosis and liver fibrosis. Accordingly the complexes of the invention have the potential to influence these conditions.

Administration of Complexes

Administration of complexes within Formula (I) to humans can be by any of the accepted modes of administration well known in the art. For example they may be administered by enteral administration such as oral or rectal, or by parenteral administration such as subcutaneous, intramuscular, intravenous and intradermal routes. Injection can be bolus or via constant or intermittent infusion. The active complex is typically included in a pharmaceutically acceptable carrier or diluent and in an amount sufficient to deliver to the subject a therapeutically effective dose.

In using the complexes of the invention they can be administered in any form or mode which makes the complex bio-available. One skilled in the art of preparing formulations can readily select the proper form and mode of administration depending upon the particular characteristics of the complex selected, the condition to be treated, the stage of the condition to be treated and other relevant circumstances. We refer the reader to Remingtons Pharmaceutical Sciences, 19$^{th}$ edition, Mach Publishing Co. (1995) for further information.

The complexes of the present invention can be administered alone or in the form of a pharmaceutical composition in combination with a pharmaceutically acceptable carrier, diluent or excipient.

The complexes are, however, typically used in the form of pharmaceutical compositions which are formulated depending on the desired mode of administration. As such, in a further embodiment the present invention provides a pharmaceutical composition including a complex of Formula (I) and a pharmaceutically acceptable carrier, diluent or excipient. The compositions are prepared in manners well known in the art.

The invention in other embodiments provides a pharmaceutical pack or kit including one or more containers filled with one or more of the ingredients of the pharmaceutical compositions of the invention. In such a pack or kit can be found a container having a unit dosage of the agent(s). The kits can include a composition including an effective agent either as concentrates (including lyophilized compositions), which can be diluted further prior to use or they can be provided at the concentration of use, where the vials may include one or more dosages. Conveniently, in the kits, single dosages can be provided in sterile vials so that the physician can employ the vials directly, where the vials will have the desired amount and concentration of agent(s). Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The complexes of the invention may be used or administered in combination with one or more additional drug(s) that are useful for the treatment of the disorder/diseases mentioned. The components can be administered in the same formulation or in separate formulations. If administered in separate formulations the complexes of the invention may be administered sequentially or simultaneously with the other drug(s).

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the complexes can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active complex is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

If desired, and for more effective distribution, the complexes can be incorporated into slow release or targeted delivery systems such as polymer matrices, liposomes, and microspheres.

The active complexes can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active complexes, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavouring, and perfuming agents.

Suspensions, in addition to the active complexes, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the complexes of this invention with suitable non-irritating excipients or carriers such as cocoa butter, polyethylene glycol or a suppository wax which are solid at room temperature but liquid at body temperature and therefore melt in the rectum or vaginal cavity and release the active complex.

Dosage forms for topical administration of a complex of this invention include powders, patches, sprays, ointments and inhalants. The active complex is mixed under sterile conditions with a pharmaceutically acceptable carrier and any needed preservatives, buffers, or propellants which may be required.

The amount of complex administered will preferably treat and reduce or alleviate the condition. A therapeutically effective amount can be readily determined by an attending diagnostician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the subject to treatment, the particular complex administered, the mode of administration, the bioavailability of the preparation administered, the dose regime selected, the use of other medications and other relevant circumstances.

A preferred dosage will be a range from about 0.01 to 300 mg per kilogram of body weight per day. A more preferred dosage will be in the range from 0.1 to 100 mg per kilogram of body weight per day, more preferably from 0.2 to 80 mg per kilogram of body weight per day, even more preferably 0.2 to 50 mg per kilogram of body weight per day. A suitable dose can be administered in multiple sub-doses per day.

Synthesis

The complexes of the various embodiments may be prepared using the reaction routes and synthesis schemes as described below, employing the techniques available in the art for each of the individual step/reactions and using starting materials that are readily available. The preparation of particular complexes of the embodiments is described in detail in the following examples, but the artisan will recognize that the chemical reactions described may be readily adapted to prepare a number of other agents of the various embodiments. For example, the synthesis of non-exemplified complexes may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, John Wiley & Sons, 1981. Alternatively, other reactions disclosed herein or known in the art will be recognized as having applicability for preparing other complexes of the various embodiments.

A suitable scheme for the production of some of the complexes of the invention is shown below in Scheme 1.

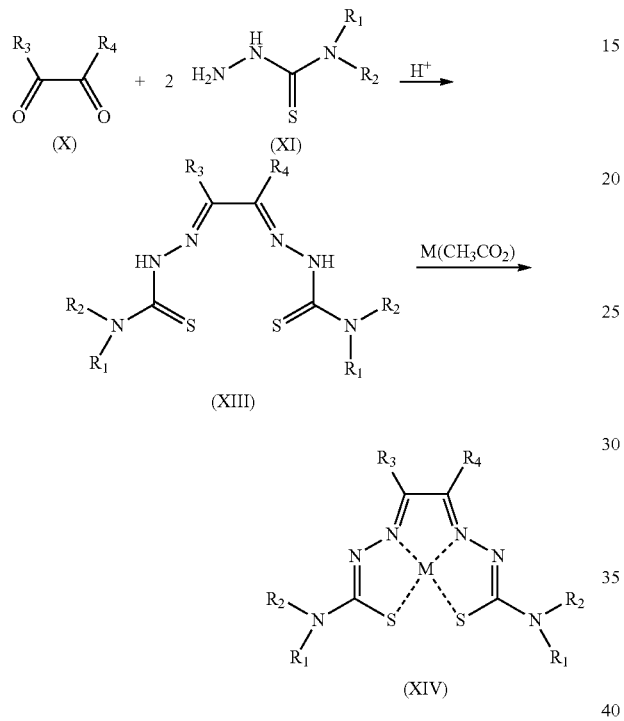

Thus condensation of dione (X) with two equivalents of a suitably functionalised thio semicarbazide (XI) under acidic conditions leads to the formation of the bis (thiosemicarbazone) (XIII). Using the reaction scheme outlined the resultant semi carbazide (XIII) will be symmetrical as the same thio semicarbazide will condense with both aldehyde moieties. The bis(thiosemicarbazone) can then be reacted with a suitable metal salt such as the metal acetate to produce the desired metal complex (XIV) and acetic acid. A wide variety of thiosemicarbazones may be produced by varying the substituents on either the aldehyde moiety or on the semicarbazide.

An alternative procedure which is particularly applicable to non-symmetrical (bis semicarbazones) is shown in Scheme 2.

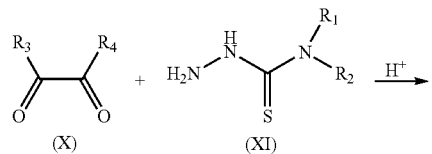

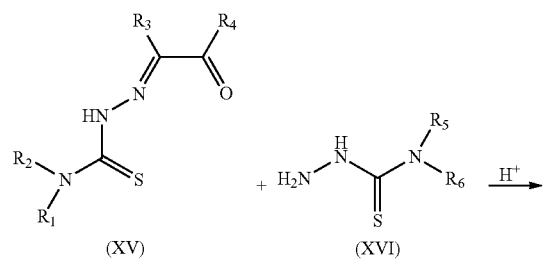

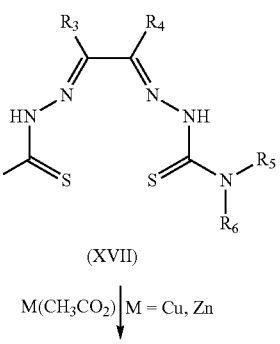

Thus as before reaction of a dione (X) with one equivalent of thio semi-carbazide (XI) under acidic conditions leads to formation of the mono thio semicarbazione derivative (XV). This can then be subjected to condensation with a second thiosemicarbazide moiety (XVI) to produce a bis(thiosemicarbazone) (XVII) which can again be reacted with a metal salt such as the metal acetate to produce the desired unsymmetrical complex (XVIII). Once again by judicious choice of starting materials (X), (XI) and (XVI) a wide variety of materials can be synthesised.

With certain bis thiosemicarbazones it is difficult to stop the formation reaction at the mono-addition step leading to the formation of the bis adduct as well as starting material. Whilst this is desired when the final product is a symmetrical adduct it is undesirable in circumstances where an asymmetrical adduct is desired. Whilst this was not an issue with all backbones it was certainly observed with a number of the products desired to be produced and so an alternative procedure was developed for adducts of this type. An alternative procedure that avoided the formation of this bis adduct in a single step was therefore developed and is shown in scheme 3.

Scheme 3 Alternative Formation of unsymmetricial bis(thiosemicarbazones).

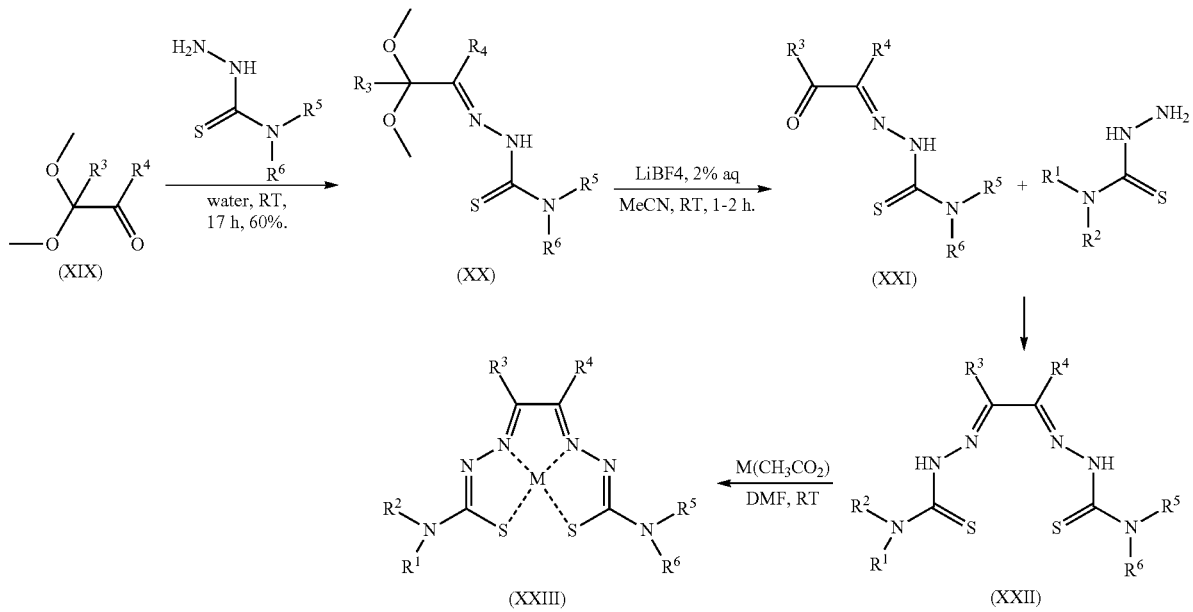

Thus molecule (XIX) was reacted with a thiosemicarbazides to afford the mono-adduct, acetal (XX). The acetal can be oxidatively cleaved to give the aldehyde (XXI) using lithium tetrafluoroboracete, a mild Lewis acid. Reaction of the aldehyde (XXI) with a different thiosemicarbazide, gave the desired asymmetric ligand (XXII) which could then be converted into the metal complex (XXIII) using the standard conditions.

EXAMPLES

Reagents useful for synthesizing compounds may be obtained or prepared according to techniques known in the art.

In the examples described below, unless otherwise indicated, all temperatures in the following description are in degrees Celsius and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated. Tetrahydrofuran (THF) and N,N-dimethylformamide (DMF) were purchased from Aldrich in SureSeal bottles and used as received. All solvents were purified by using standard methods in the art, unless otherwise indicated.

Nuclear magnetic resonance spectra (NMR) spectra were acquired with either a Varian 400 MHz spectrometer CH at 400 MHz) or a Varian Inova 500 NMR ($^1$H at 500 MHz). All chemical shifts were referenced to residual solvent peaks and are quoted in ppm relative to TMS. All spectra were recorded in $d_6$-DMSO. Mass spectra were recorded using the electrospray technique (positive ion) VG BioQ Triple Quadrupole Mass Spectrometer. All reagents and other solvents were obtained from standard commercial sources and were used as received. ATSMH$_2$, [Cu(ATSM)], [Zn(ATSM)], ATSPH$_2$, [Cu(ATSP), Zn(ATSP)]. ATSEH$_2$, [Cu(ATSE)], GTSMH$_2$ and [Cu(GTSM)] were prepared by variations of reported procedures, see: 1) P. J. Blower, T. C. Castle, A. R. Cowley, J. R. Dilworth, P. S. Donnelly, E. Labisbal, F. E. Sowrey, S. J. Teat and M. J. Went, *Dalton Trans.,* 2003, 4416-4425 and references therein; 2) J. L. J. Dearling, J. S. Lewis, G. D. Mullen, M. J. Welch, and P. J. Blower, *J. Biol. Inorg. Chem.,* 2002, 7, 249 and references therein; 3) P. McQuade, K. E. Martin, T. C. Castle, M. J. Went, P. J. Blower, M. J. Welch and J. S. Lewis, *Nucl. Med. Biol.,* 2005, 32, 147. All $^1$H NMR spectra and ES MS were as expected.

Example 1 Synthesis of [Zn(ATSEH$_2$)]

ATSEH$_2$ (0.134 g, 0.46 mmol) and Zn(CH$_3$CO$_2$)$_2$·2H$_2$O (0.102 g, 0.46 mmol) were added to ethanol (5 mL). The mixture was heated at reflux for 2 hours under an atmosphere of nitrogen and then allowed to cool to room temperature. The bright yellow solid that formed was collected by filtration and washed with ethanol, and diethyl ether to give [Zn(ATSE)] as a yellow powder (0.122 g, 0.35 mmol, 76%). $^1$H NMR (400 MHz): δ 1.08, 6H, t, $^3J_{HH}$=7 Hz, CH$_2$CH$_3$; 2.18 ppm, 6H, s, 2×CH$_3$; 3.30, 4H, m partially obscured by H-OD peak from solvent, CH$_2$CH$_3$. ES MS (+ve ion): m/z=351=[Zn(C$_{10}$H$_{18}$N$_6$S$_2$)+H$^+$]$^+$.

Example 2 Synthesis of ChexTSE 1,2-Cyclohexanedione (0.439 g, 3.92 mmol) was added to ethanol (25 mL) followed by N4-ethyl-3-thiosemicarbazide (0.933 g, 7.83 mmol) and a few drops of H$_2$SO$_4$ (conc). The mixture was heated at reflux under an atmosphere of nitrogen for 3 hours and then allowed to cool to room temperature. A yellow precipitate formed which was collected by filtration and washed with ethanol, and diethyl ether to ChexTSE as a yellow solid (0.945 g, 3.00 mmol, 76%). $^1$H NMR (400 MHz): δ 1.09, 3H, t, $^3J_{HH}$=7 Hz, CH$_2$CH$_3$; 1.13, 3H, t, $^3J_{HH}$=7 Hz, CH$_2$CH$_3$; 1.66, 4H, m, 2×CH$_2$ cyclohexyl; 2.56, 4H, m, 2×CH$_2$ cyclohexyl; 3.54, 4H, m, 2×NHCH$_2$CH$_3$; 8.18, 1H, br s, NH; 8.61, br s, NH; 10.44, 1H, br s, NH; 12.25, 1H, br s, NH. ES MS (+ve ion): m/z=315=[C$_{12}$H$_{22}$N$_6$S$_2$+H$^+$]$^+$.

Example 3 Synthesis of [Zn(Chextsc)]

ChexTSE (0.190 g, 0.60 mmol) was added to ethanol (10 mL) followed by Zn(CH$_3$CO$_2$).2H$_2$O (0.133 g, 0.60 mmol) and the mixture was heated at reflux under an atmosphere of nitrogen for 3 hours. The mixture was allowed to cool to room temperature and a yellow solid precipitated. The solid was collected by filtration and washed with ethanol, and diethyl ether to give [Zn(Chextsc)] as a yellow solid (0.157 g, 0.42 mmol, 70%). $^1$H NMR (400 MHz): δ 1.07, 6H, t, $^3J_{HH}$=7 Hz, 2×CH$_2$CH$_3$; 1.64, 4H, m, 2×CH$_2$ cyclohexyl; 2.58, 4H, m, 2×CH$_2$ cyclohexyl; 3.32, 4H, m, obscured by H-OD signal in solvent, 2×NHCH2CH3. ESMS (+ve ion): m/z=378=[Zn(C$_{12}$H$_{20}$N$_6$S$_2$+H$^+$]$^+$.

Example 4 Synthesis of [Cu(Chextsc)]

ChexTSC (0.202 g, 0.64 mmol) and Cu(CH$_3$CO$_2$)$_2$.H$_2$O 0.202 g, 0.64 mmol) were added to ethanol (10 mL). The mixture was heated at reflux under an atmosphere of nitrogen for 3 hours and then allowed to cool to room temperature. The red-brown solid that precipitated was collected by filtration an washed with ethanol and diethyl ether to give [Cu(ChexTSC)] as a red-brown powder (0.166 g, 0.44 mmol, 69%). ES MS (+ve ion): m/z=377=[Cu(C$_{12}$H$_{20}$N$_6$S$_2$+H$^+$]$^+$.

Example 5 Synthesis of symmetrical GTS Ligand (3): (4-Chlorophenyl)-Derivative 4-(4-Chlorophenyl)-3-thiosemicarbazide (0.60 g, 2.50 mmol) was stirred in water (2 mL) and acetic acid (2 mL). 1,4-Dioxane (2 mL) was added until the solution become clear. A 40% aqueous solution of glyoxal (136 μL, 1.19 mmol) was added drop wise to the solution which was stirred under and argon atmosphere for 2 h. In this time a white precipitate was evident in the reaction solution. The reaction was concentrated slightly, filtered, and the residue was washed sequentially with water (2 mL), hot ethanol (2 mL) and ether (2 mL) to give the ligand as a pale yellow solid (0.360 g, 0.85 mmol, 71%). $^1$H NMR (400 MHz): δ 7.39, 4H, d, $^3J_{HH}$=8.4 Hz, 4× Ar—H, 7.58, 4H, d, $^3J_{HH}$=8.4 Hz, 4× Ar—H; 7.88, 2H, s, 2×CH=N, 10.27, 2H, s, 2×NH—Ar; 12.23, 2H, s, 2×NH—N=N. ESMS (-ve ion): m/z=424=[(C$_{16}$H$_{14}$Cl$_2$N$_6$S$_2$—H$^+$]$^+$.

Example 6 Synthesis of Symmetrical GTS Copper Complex (A8): (4-Chlorophenyl)-Derivative Copper(II) acetate monohydrate (0.04 g, 0.18 mmol) was added to a stirred solution of the ligand (3) (0.08 g, 0.18 mmol) dissolved in minimal DMF (1 mL). A purple colour change occurred immediately. The reaction was stirred under an argon atmosphere at room temperature for 1 h, and then concentrated to a purple solid. The solid was sonicated in ethanol (2 mL), removed via filtration and washed with hot ethanol (2×1 mL), ether (2 ml) and air dried to afford the copper complex as a purple solid (0.07 g, 0.13 mmol, 71%). ES MS (-ve ion): m/z=485=[Cu(C$_{16}$H$_{12}$Cl$_2$N$_6$S$_2$—H$^+$]$^-$.

Example 7 Synthesis of Symmetrical GTS Zinc Complex (A7): (4-Chlorophenyl)-Derivative Zinc(II) acetate dehydrate (0.03 g, 0.14 mmol) was added to a stirred solution of the ligand (3) (0.06 g, 0.14 mmol) dissolved in minimal DMF (1 mL). An orange colour change occurred immediately. The reaction was stirred under an argon atmosphere at room temperature for 1 h, and then concentrated to an orange gum. The gum was sonicated in ethanol (2 mL) causing a bright orange solid to precipitate out of solution. The solid was removed and washed with hot ethanol (2×1 mL), ether (2 ml) and air dried to afford the zinc complex as a orange solid (0.04 g, 0.08 mmol, 62%). $^1$H NMR (400 MHz): δ 7.29, 4H, d, $^3J_{HH}$=8.8 Hz, 2× Ar—H, 7.78, 4H, d, $^3J_{HH}$=8.8 Hz, 2× Ar—H, 7.84, 2H, s, 2×CH=N, 9.84, 2H, bs, 2×NH—Ar. ES MS (+ve ion): m/z=489=[Zn(C$_{16}$H$_{12}$Cl$_2$N S+H$^+$]$^+$.

Example 8 Synthesis of Unsymmetrical GTS Ligand (10): Methyl/Phenyl-Semicarbazide Derivative Step 1: Acetal Protected Mono Substituted (Methylthiosemicarbazide) Ligand (XX).

A 40% aqueous solution of dimethoxyacetaldehyde (0.65 mL, 4.28 mmol) was added to a stirred suspension of 4-methyl-3-thiosemicarbazide (0.50 g, 4.75 mmol) in methanol (15 mL). The reaction was stirred under an argon atmosphere at room temperature for 17 h. The methanol was removed under reduced pressure and the aqueous solution was extracted with dichloromethane (2×20 mL). The combined organic layers were washed with water (2×10 mL) and dried (Na$_2$SO$_4$). Concentration gave a white solid (0.46 g, 2.40 mmol, 56%). $^1$H NMR (400 MHz): δ 2.93, 3H, d, $^3J_{HH}$=4.4 Hz, NH—CH$_3$; 3.29, 3H, s, CH$_3$; 3.32, 3H, s, CH$_3$; 4.69, 1H, d, $^3J_{HH}$=5.6 Hz, CH—(OCH$_3$)$_2$; 7.25, 1H, d, $^3J_{HH}$=5.6 Hz, CH=C, 8.27, 1H, broad d, $^3J_{HH}$=3.6 Hz, NH—CH$_3$; 11.31, 1H, s, NH—N=C.

Step 2: Formation of the Aldehyde (XXI).

A 1.0 M solution of lithium tetrafluoroborate in acetonitrile (1.44 mL, 1.05 mmol) was added directly to the methyl thiosemicarbazide derived acetal (XX) (0.10 g, 5.23 mmol) and stirred for a few minutes. The mixture was diluted with a 2% aqueous solution of acetonitrile (20 mL) and stirred under an argon atmosphere at room temperature for 17 h. The reaction was quenched with a saturated aqueous brine solution (10 mL), the organic layer was removed and the aqueous phase was extracted with ether (2×10 mL). The combined organic layers were dried (Na$_2$SO$_4$) and concentrated under reduced pressure to afford the desired aldehyde as an orange gummy solid (0.04 g, 0.03 mmol), 58%). The product was used directly in the next step. $^1$H NMR (400 MHz): δ 3.00, 3H, d, $^3J_{HH}$=4.8 Hz, NH—CH$_3$; 7.43, 1H, d, $^3J_{HH}$=8.0 Hz, CH=C, 9.01, 1H, bs, NH—CH$_3$; 9.45 1H, d, $^3J_{HH}$=8.0 Hz, CH=O; 12.47, 1H, s, NH—N=C.

Step 3: Reaction with Second Thiosemicarbazides-Unsymmetrical Ligand Formation (XXII)

To a solution of the aldehyde (0.04 g, 0.31 mmol) dissolved in DMF (3 mL) containing activated 4 Å molecular sieves, was added 4-phenyl-3-thiosemicarbazide (0.06 g, 0.34 mmol). The reaction was stirred for 5 h under an argon atmosphere at 60° C. The reaction was filtered, the sieves were washed with a little DMF and the solution was concentrated to give a yellow gum. The gum was sonicated in ethanol (2 mL) and the solid was removed via filtration. The residue was washed with hot ethanol (2×2 mL) then ether (2×2 mL) to give a cream solid (0.04 g, 0.12 mmol, 40%). $^1$H NMR (400 MHz): δ 2.96, 3H, d, $^3J_{HH}$=4.4 Hz, NH—CH$_3$; 7.17, 1H, m, 1× Ar—H, 7.33, 2H, m, 2× Ar—H, 7.52, 2H, m, 2× Ar—H, 7.79, 2H, ABq, $^3J_{HH}$=8.8, 11.6 Hz, 2×CH=N, 8.55, 1H, broad d, $^3J_{HH}$=4.0 Hz, NH—CH$_3$; 10.16, 1H, NH-Ph; 11.83, 1H, s, NH—N=C, 12.09, 1H, NH-Ph; 11.83, 1H, s, NH—N=C.

Step 4: Unsymmetrical GTS Copper Complex Formation (XXIII). A19

Copper(II) acetate monohydrate (0.06 g, 0.29 mmol) was added to a stirred solution of the ligand (all) (0.09 g, 0.29 mmol) dissolved in minimal DMF (1 mL). A purple colour change occurred immediately. The reaction was stirred under an argon atmosphere at room temperature for 1 h, and then concentrated to a purple solid. The solid was sonicated in ethanol (2 mL), removed and washed with hot ethanol (2×1 mL), ether (2 ml) and air dried to afford the copper complex as a purple solid (0.07 g, 0.20 mmol, 64%). ES MS (+ve ion): m/z=371=[Cu($C_{12}H_{14}N_6S_2$+H$^+$]$^+$.

Step 5: Unsymmetrical GTS Zinc Complex Formation (XXIII). A9

Zinc(II) acetate dihydrate (0.05 g, 0.24 mmol) was added to a stirred solution of the ligand (12) (0.07 g, 0.24 mmol) dissolved in minimal DMF (1 mL). An orange colour change occurred immediately. The reaction was stirred under an argon atmosphere at room temperature for 1 h, and then concentrated to an orange gum. The gum was sonicated in ethanol (1 mL) and the solid was removed and washed with ether (1 ml) and air dried to afford the zinc complex as an orange solid (0.04 g, 0.11 mmol, 47%). $^1$H NMR (400 MHz): δ 2.96, 3H, bs, NH—CH$_3$; 6.91, 1H, bs, Ar—H, 7.22, 2H, bs, Ar—H, 7.54, 1H, bs, NH—CH$_3$; 9.53, 1H, bs, NH—Ar.ES MS (+ve ion): m/z=359=[Zn($C_{11}H_{12}N_6S_2$+H$^+$]$^+$.

Using variations on the procedures outlined above and the reaction mechanisms outlined in schemes 1 to 3 the ligands shown in Table 1 were synthesized in addition to the initial ligands disclosed on pages 21 and 22.

TABLE 1

| Ligand Number | Structure |
|---|---|
| 1 | 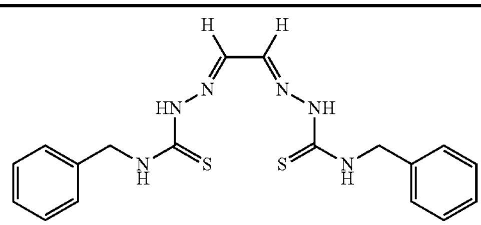 |
| 2 | 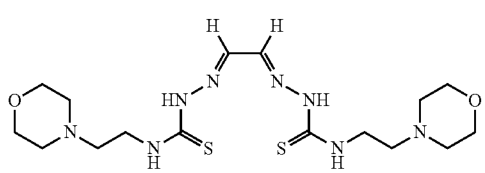 [SMILES: S=C(NCCN1CCOCC1)N/N=C/C=N/NC(=S)NCCN1CCOCC1] |
| 3 | 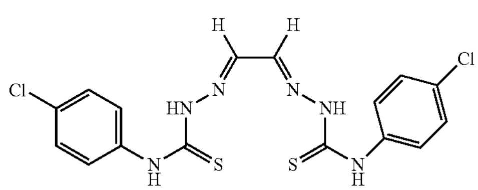 [SMILES: S=C(N/N=C/C=N/NC(=S)Nc1ccc(Cl)cc1)Nc1ccc(Cl)cc1] |
| 4 | 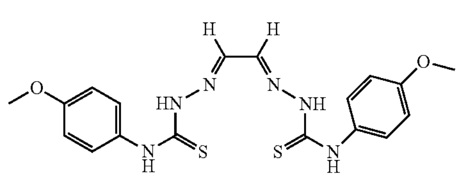 |

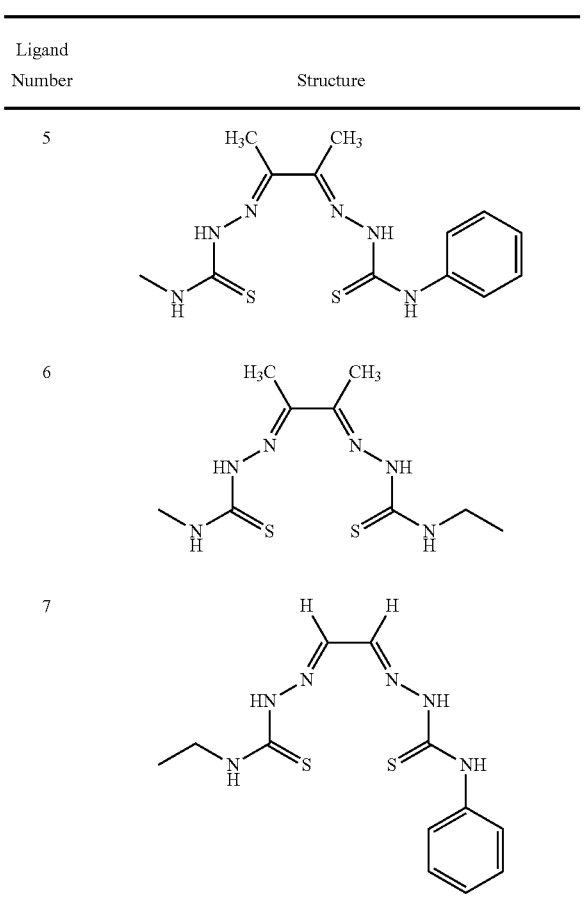

TABLE 1-continued

| Ligand Number | Structure |
|---|---|
| 5 | 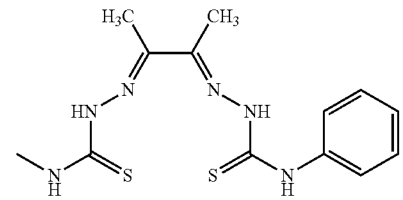 [SMILES: CNC(=S)N/N=C(C)/C(C)=N/NC(=S)Nc1ccccc1] |
| 6 | 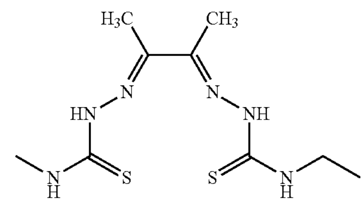 [SMILES: CCNC(=S)N/N=C(C)/C(C)=N/NC(=S)NC] |
| 7 | 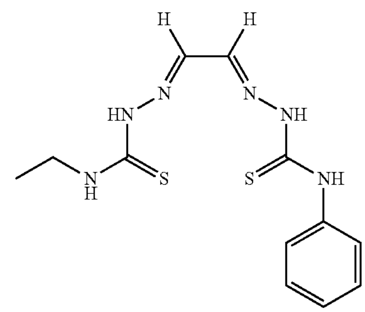 [SMILES: CCNC(=S)N/N=C/C=N/NC(=S)Nc1ccccc1] |
| 8 | 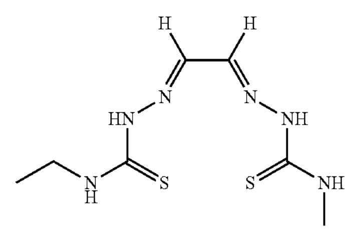 |
| 9 | 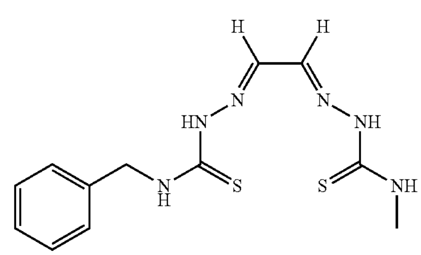 [SMILES: CNC(=S)N/N=C/C=N/NC(=S)NCc1ccccc1] |
| 10 | 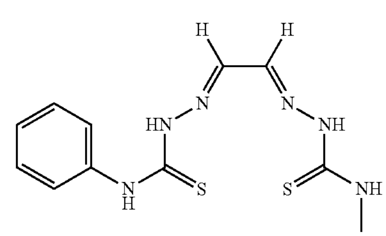 [SMILES: CNC(=S)N/N=C/C=N/NC(=S)Nc1ccccc1] |

TABLE 1-continued

| Ligand Number | Structure |
|---|---|
| 11 | (structure) |
| 12 | (structure) |

By utilising the ligands in Table 1 and the metal complex formation procedures discussed above a number of metal complexes as shown in Table 2 were made.

TABLE 2

| Complex No | Structure |
|---|---|
| A1 | (structure) |
| A2 | (structure) |
| A3 | (structure) |
| A4 | (structure) |
| A5 | (structure) |
| A6 | (structure) |
| A7 | (structure) |
| A8 | (structure) |
| A9 | (structure) |
| A10 | (structure) |
| A11 | (structure) |
| A12 | (structure) |

TABLE 2-continued

| Complex No | Structure |
|---|---|
| A13 | [Cu complex with ethyl-NH and phenyl-NH thiosemicarbazone substituents] |
| A14 | [Cu complex with ethyl-NH and methyl-NH thiosemicarbazone substituents] |
| A15 | [Zn complex with ethyl-NH and methyl-NH thiosemicarbazone substituents] |
| A16 | [Cu complex with benzyl-NH and methyl-NH thiosemicarbazone substituents] |
| A17 | [Zn complex with benzyl-NH and methyl-NH thiosemicarbazone substituents] |
| A18 | [Zn complex with ethyl-NH and phenyl-NH thiosemicarbazone substituents] |
| A19 | [Cu complex with phenyl-NH and methyl-NH thiosemicarbazone substituents] |
| A20 | [Zn complex with phenyl-NH and methyl-NH thiosemicarbazone substituents] |
| A21 | [Cu complex with morpholinoethyl-NH and methyl-NH thiosemicarbazone substituents] |
| A22 | [Zn complex with morpholinoethyl-NH and methyl-NH thiosemicarbazone substituents] |
| A23 | [Cu complex with 4-methoxyphenyl-NH and methyl-NH thiosemicarbazone substituents] |
| A24 | [Zn complex with 4-methoxyphenyl-NH and methyl-NH thiosemicarbazone substituents] |

Cellular Uptake of BTSC Complexes

Example 9 Cu-BTSC

APP-transfected Chinese Hamster Ovary (APP-CHO) cells were treated with a range of [Cu(BTSC)] complexes with dialkyl backbones at 1-50 μM for 6 hr in serum-free culture medium. Cells were washed twice with phosphate buffered saline (PBS) and cells scraped into fresh PBS and pelleted at 10,000 rpm in a microfuge for 5 min. Supernatant was discarded and cell pellets frozen at −70° C. until metal levels were determined by inductively-coupled plasma mass spectrometry (ICP-MS) at the Department of Pathology, University of Melbourne.

Example 10 Zn-BTSC

Zn-BTSC complexes are less stable than their copper complexes (related derivatives having association constants of the order of log K=7 but are still capable of effectively transporting Zn into the cell. Treatment of the cells with [Zn(BTSC)] complexes resulted in significant increases in the intracellular Zn levels as measured by ICP-MS. [Zn(ATSM)] and [Zn(ATSE)] induced 8.2±0.25 and 9.8±0.9 fold increases in cellular Zn levels respectively (FIG. 2). APP-transfected CHO cells were treated with [Zn(BTSC)] complexes at 1-50 µM for 6 hr in serum-free culture medium. Cells were washed twice with phosphate buffered saline (PBS) and cells scraped into fresh PBS and pelleted at 10,000 rpm in a microfuge for 5 min. Supernatant was discarded and cell pellets frozen at −70° C. until metal levels were determined by inductively-coupled plasma mass spectrometry (ICP-MS) at the Department of Pathology, University of Melbourne. Treatment of the cells with [Zn(btsc)] complexes resulted in significant increases in the intracellular Zn levels as measured by ICP-MS. [Zn(ATSM)] and [Zn(ATSE)] induced 8.2±0.25 and 9.8±0.9 fold increases in cellular Zn levels respectively when compared to untreated controls (FIG. 2).

Reduction in Extracellular Amyloid Beta Levels

Example 11 Cu(GTSM)

Treatment of APP-CHO cells with [Cu(GTSM)] resulted in an increase in the intracellular copper levels as expected of the cell permeable Cu-ligand. Five treatment regimes were used namely a control, 1 µM, 5 µM, 10 µM, 25 µM and 50 µM (FIG. 3). APP-transfected CHO cells were treated with each of the doses of [Cu(GTSM)] for 6 hr in serum-free medium and conditioned medium was then collected and assayed for Aβ1-40 peptide by routine Aβ ELISA. [Cu(GTSM)] significantly inhibited Aβ1-40 levels in the medium at all concentrations tested when compared to uncomplexed GTSM.

Example 12 Zn-BTSC Complexes

Treatment of APP-CHO cells with a number of zinc complexes resulted in an increase in the intracellular zinc levels as expected of the cell permeable Zn-ligand. Five treatment regimes were used namely a control, 1 µM, 5 µM, 10 µM, 25 µM and 50 µM (FIG. 4). APP-transfected CHO cells were treated with each of the doses of [Zn(BTSC)] for 6 hr in serum-free medium and conditioned medium was then collected and assayed for Aβ1-40 peptide by routine Aβ ELISA. All Zn-BTSC significantly inhibited Aβ1-40 levels in the medium at 10-50 µM. Zn-Chex TSE and Zn-ATSE also inhibited Aβ at 1 µM.

Example 13 Cu Inhibits Zn Uptake and Loss of Secreted Aβ Induced by [Zn(BTSC)]

To examine this, cells were exposed to 10 µM [Zn(ATSE)] or [Zn(ATSP)] with or without 5-50 µM Cu²⁺ for 6 hr. Co-treatment of cells with Cu and the Zn-BTSC complexes reduced the level of Zn uptake compared to Zn-BTSC alone (FIG. 5). This indicates that Cu is able to displace the weaker binding Zn to form Cu-BTSC complexes and reduce the uptake of Zn-BTSC and the results after analysis are shown in FIG. 5.

Example 14 Effect of Temperature on Metal Uptake

A study was conducted in which cells were exposed to differing concentrations of one of the complexes of the invention at a number of various concentrations and at either 4 or 37° C. Cells were treated with the complexes at either 37° C. or 4° C. for 6 hr and metal levels determined by ICP-MS and Aβ1-40 measured by ELISA. The results as shown in FIG. 6 clearly indicate that cellular uptake is dependent upon temperature. Treatment of cells at 37° C. results in a high level of metal uptake which results in loss of extracellular Aβ. Incubation of cells at 4° C. results in substantially lower metal uptake and therefore, reduced effects on extracellular Aβ. The results indicate that metal uptake is therefore likely to be an active, rather than passive process and could provide the opportunity to target specific metal-BTSC receptors to improve efficacy of the complexes.

Example 15 Reduction of Cellular Abeta

Generation of APP-Transfected Chinese Hamster Ovary (CHO)

APP-CHO cells were generated by expressing the 695 amino acid APP cDNA in the pIRESpuro2 expression vector (Clontech, Mountain View, Calif., USA). Cells were transfected using Lipofectamine 2000 and cultured in RPMI-1640 media supplemented with 1 mM glutamine and 10% fetal bovine serum (all from Invitrogen, Mount Waverley, Victoria, Australia). Transfected cells were selected and maintained using 7.5 µg/ml puromycin (Sigma-Aldrich).

Treatment of Cells with Complexes

APP-CHO cells were passaged at a ratio of 1:5 and grown in 6 well plates for 3 days before experiments. Compounds were prepared as a 10 mM stock solution in DMSO and added to serum-free RPMI medium supplemented with puromycin. Medium was briefly mixed by aspiration prior to addition to cells. Control cultures were treated with vehicle (DMSO) alone. Cultures were incubated for 6 hr and conditioned media taken for measurement of Aβ1-40 levels by ELISA.

Double Antibody Capture Enzyme-Linked Immunosorbent Assay (ELISA) for Aβ Detection Aβ levels were determined in culture medium using the 384 well Aβ1-40 ELISA protocol. 384 well plates were coated with monoclonal antibody (mAb) G2-10 in carbonate-bicarbonate coating buffer (pH 9.6) for $Aβ_{1-40}$ detection. The plates were left to incubate overnight at 4° C. with rocking. The plates were then washed three times with PBST at RT with rocking and the solution discarded after each wash. Then 100 µL of 0.5% (w/v) hydrolysed casein in PBS (pH 7.4) was added to each well and left to incubate for 2 hr at 37° C. to prevent non-specific binding. The plates were then washed three times with PBST at RT with rocking. 20 ng of biotinylated mAb WO2 (epitope at $Aβ_{5-8}$) was added to each well of the plates (10 µL/well at 2 ng/µL). 50 µL/well of $Aβ_{1-40}$ standard peptide samples (MHRI, Melbourne, Australia), cell culture medium samples and the blanks were added. The plates were left to incubate overnight at 4° C. with rocking. The plates were washed nine times with PBST at RT with rocking. 25 µL streptavidin-labelled europium was added at a dilution of 1:1000. Plates were then washed ten times with PBST where the 9$^{th}$ and 10$^{th}$ wash was left on for 5 min before discarding. To develop the plates 80 μL of enhancement solution was added to each well and plates were read in a WALLAC Victor² plate reader with excitation (Ex) at 340 nm and emission (Em) at 613 nm. $A\beta_{1-40}$ peptide standards and samples were assayed in triplicate. The values obtained from the triplicate wells were used to calculate the Aβ concentration (expressed as ng/mL) based on the standard curve generated on each plate and are given in Table 3.

TABLE 3

| Test Compound | Abeta as a percentage of Control |
|---|---|
| Control (DMSO) | 100 |
| A4 | 84 |
| A5 | 13 |
| A7 | 36 |
| A8 | 56 |
| A10 | 53 |
| A13 | 42 |
| A14 | 3 |
| A16 | 30 |
| A17 | 95 |
| A18 | 35 |
| A19 | 38 |
| A20 | 86 |
| A21 | 50 |
| A23 | 47 |
| A24 | 56 |

Example 16 Ionophore Assay

M17 human neuroblastoma cells were plated out on 6 well plates and left overnight. Enough cells were added to give approximately 70% confluent the following day of the experiment.

The test cells were incubated in 1 ml of media and compound mix for 5 hours at 37° C. At the end of the incubation the media was removed with a vacuum aspirator and 1 ml of PBS added to dislodge the cells. Cells are then put into Eppendorf tubes and pelleted. The PBS is removed and the remaining cell pellets are frozen at −20 C.

Cell pellets of similar levels are placed in 1.5 ml microfuge tubes. To each tube was added 50 μl of concentrated Nitric Acid (Aristar, BDH) to each cell pellet and allowed each cell pellet was allowed to digest over night. The samples were heated for 20 min at 90° C. to complete the digestion. The volume of each sample was reduced to ~45 μl after digestion. To each was added 1 ml of the 1% Nitric Acid diluent. Measurements were made using a Varian UltraMass ICPMS instrument under operating conditions suitable for routine multi-element analysis.

The instrument was calibrated using Blank, 10, 50 and 100 ppb of a certified multi-element ICPMS standard solution (ICP-MS-CAI2-1, Accustandard) for Fe, Cu and Zn in 1% nitric acid. Used an certified internal standard solution containing 100 ppb Yttrium (Y 89) as an internal control (ICP-MS-IS-MIX1-1, Accustandard).

The data were reported versus level of a known internal control (Clioquinol) and shown in Table 4. The data in Table 4 demonstrates that the complexes of the invention are effective in delivering the metal to the cell.

Example 17 Cytotoxicity Testing—M17 Neuroblastoma Cells

Day 1.
The test cells were cultured at 37° C./5% $CO_2$ till almost confluent in 75 cm² flask. The media was removed and the cells incubated with 5 ml PBS for about 5 mins to dislodge cells from the plastic surface. A pipette was used to resuspend cells and 5 mls of growth media added. The cell suspension was removed and added to 15 ml Falcon tube. The suspension was mixed well by inversion and about 100 μl transferred into an Eppendorf.

A typical assay assessing 15 compounds uses five 48 well plates. The inner 24 wells are the only ones used to reduce the amount of evaporation over 48 hrs. 200 μl of media was added to each of the inner 24 wells. Cell suspensions were mixed by inversion and the desired number of cells added to each well. Cell addition was continued across each plate and the cell suspension mixed in the falcon tube by inversion between each plate. The plates were given a minor shake and returned to a 37° C. incubator. Plates were left overnight for cells to settle in the wells.

Day 2.
Compounds to be tested were selected for the assay. Calculate from the mol wt. and mg of compound in the Eppendorf, the number of ml of DMSO to add to make a stock solution of 10 mM. In the case of CQ (Clioquinol) a 1 mM stock solution is required due to precipitation of a more concentrated solution when diluted in media.

DMSO was added to the Eppendorfs (typically 200-500 μl), vortexed until dissolved and incubated with the compounds at 37° C. for 60 mins to aid solubilisation. Compounds were removed and again vortexed and checked for any undissolved compound.

The 10 mM stock solutions should then be diluted 1:10 to make a final concentration of 1 mM. 180 μl of DMSO was added to the test tube and 20 μl of each of the compound solutions was added to each of the test tubes to create the test solutions which were then vortexed again to ensure complete homogenation of the test mixture. Each compound is then diluted to final concentrations of 10 μM and 1 μM.

The desired amount of the test solution and the control sample was added to the plates which were then returned to the incubator for a 48 hour period at 37° C. At the completion of the 48 hour period the plates were removed from the incubator and an aspirator used to remove the media from the first plate. Then 220 μl of MTT/media solution was added to each well. Plates were then returned to 37° C. and incubated for 1 hour. After 1 hour the plates were removed from the incubator and the media/MTT solution removed using the aspirator vacuum pump.

200 μl DMSO was added to each well and the plate gently agitates so that the DMSO dissolves the MTT crystals and the remaining cell debris. After about 10 mins the now purple DMSO in the wells should be clear. MTT is a tetrazolium salt which is converted from yellow to purple by active mitochondria. The more cells present and therefore more mitochondria results in a more intense purple colour. The plates can now be read on a plate reader at 570 nm. The results are provided in Table 4.

Example 18 Cytotoxicity Testing—Primary Neuronal Cultures

Primary neuronal cortical cultures were prepared under sterile conditions. Embryonic day 14 C57Bl/6 mouse cortices were removed, dissected free of meninges, and dissociated in 0.025% (w/v) trypsin (Sigma) in Krebs buffer. The dissociated cells were triturated using a filter-plugged fine pipette tip, pelleted, resuspended in plating medium (minimum Eagle's medium, 10% fetal calf serum, 5% horse serum), and counted. Cortical neuronal cells were plated into poly-D-lysine coated 48-well plates at a density of 150,000 cells/well in 250 μL plating medium. All cultures were maintained in an incubator set at 37° C. with 5% $CO_2$. After 2 h the plating medium was replaced with fresh neurobasal medium containing B27 supplements (containing antioxidants), geneticin, and glutamine (all tissue culture reagents were purchased from InVitrogen unless otherwise stated). This method resulted in cultures highly enriched for neurons (>95% purity) with minimal astrocyte and microglial contamination as determined by immunostaining of culture preparations using specific marker antibodies.

Cytotoxicity Assays

The neuronal cells were allowed to mature for 6 days in culture before commencing treatment using freshly prepared modified culture media (neurobasal medium plus B27 supplements (minus antioxidants), geneticin, and cytosine β-D-arabinofuranoside (Sigma)). For the treatment of neuronal cultures, freshly prepared test compound stock solutions were diluted to the final concentration (as outlined below) in 200 μL modified culture media. The mixtures were then added to neuronal cells for up to 4 days. The health of the cells was periodically monitored by phase contrast microscopy, and cell viability was quantitated using the MTS assay (Promega, Madison, Wis.). The experimental media was replaced with freshly prepared modified culture media containing 10% v/v MTS. The plates were returned to the 37° C. incubated with 5% $CO_2$ for 3 h. Then a 150-μL aliquot from each well was transferred to separate wells of a 96-well plate. The color change of each well was determined by measuring the absorbance at 490 nm and background readings of MTS incubated in cell-free medium were subtracted from each value before calculations. The data were normalized and calculated as a percentage of untreated vehicle control values. Data are shown as mean±S.E. All samples are tested in triplicate and untreated vehicle treated cells were present on every plate tested.

Preparation of Test compounds and "Drug Plate"

Test compounds were initially dissolved in 100% DMSO (Sigma) to a concentration of 5 mM. 5 mM stock solution was diluted to give working concentrations of 1 mM and 0.1 mM. Test compounds were not added directly to cells, instead they were added to a sterile 48 well 'Drug Plate', then diluted with modified culture media. After the addition of the modified culture media to the drug plate, the media was mixed gently and 200 μl aliquots (in triplicates) was added to plates containing neurons.

TABLE 4

| Complex No | Ionophore[1] | Cytotox[2] | | | |
|---|---|---|---|---|---|
| | | PN 1 μM | PN 10 μM | M17 1 μM | M17 10 μM |
| A1 | 701 | 11.2 | 10.8 | 2.5 | 0 |
| A2 | 157.1 | NT | NT | NT | NT |
| A3 | NT | NT | NT | NT | NT |
| A4 | 129 | 99 | 104.6 | 37.9 | 44.4 |
| A5 | 1163 | 30.5 | −20.6 | 1.8 | 0.6 |
| A6 | 699 | 2.7 | −2.8 | 9.2 | −0.5 |
| A7 | 126 | 185 | 164.5 | 76.1 | 43.6 |
| A8 | 95 | 96.5 | 73.8 | 73.0 | 48.2 |
| A9 | 217 | 114.4 | 1.3 | 47.2 | 57.3 |
| A10 | 133 | 99.1 | 69.0 | 43.2 | 52.9 |
| A11 | 142 | 132.8 | 140.5 | 49.1 | 52.5 |
| A12 | 166 | 116.8 | 5.3 | 86.8 | 53.9 |
| A13 | 645 | 0.2 | −1.5 | −0.8 | −0.5 |
| A14 | 287 | −5.0 | −6.2 | −2.6 | −3.4 |
| A15 | 100 | 103.6 | 106.4 | 43.2 | 19.1 |
| A16 | 394 | −4.5 | −5.7 | −2.8 | −3.3 |
| A17 | 124 | 100.6 | 106.5 | 53.1 | 42.0 |

TABLE 4-continued

| Complex No | Ionophore[1] | Cytotox[2] | | | |
|---|---|---|---|---|---|
| | | PN 1 μM | PN 10 μM | M17 1 μM | M17 10 μM |
| A18 | 159 | 79.9 | 64.3 | 96.5 | 86.5 |
| A19 | 536 | 19.4 | −5.4 | −2.7 | −2.9 |
| A20 | 114 | 44.9 | 84.4 | 56.8 | 51.9 |
| A21 | 395 | −31.3 | −31.7 | −2.8 | −3.5 |
| A22 | 125 | −7.5 | −11.6 | 41.4 | 20.1 |
| A23 | 559 | 1.8 | 1.9 | 24.9 | −2.2 |
| A24 | 130 | 101 | 96.6 | 97.3 | 93.7 |

[1](% uptake of metal at 10 μm)
[2](% viable)
NT = Not tested
A1 = CuGTSM
A2 = CuATSM
A3 = ZnATSM Example 19 Anti-Oxidant Activity Complex A8

In order to determine the ability of the complexes of the invention to act as anti-oxidants a representative complex (A8) was subjected to an Oxyblot™ assay. This assay detects carbonyl groups (aldehydes and ketones) on proteins produced by metal-catalysed oxidation. Proteins are sourced from brain slices of Tg mice that have been subject to the test compounds. Carbonyl groups are thought to be a hallmark of the oxidation status of the proteins. Carbonyl groups on protein side-chains are derivatised to 2,4-dinitrophenylhydrazone (DNP-hydrazone) by reaction with 2,4-dinitrophenylhydrazine (DNPH). The samples can then undergo gel electrophoresis or directly put on a dot-blot. Primary antibody detects the DNP exposed moiety of proteins, using a provided standard to read off particular concentrations of DNP found in the proteins.

Procedure

Buffers

All buffers were fresh before the assay, except the derivitisation DNPH solution. DNPH stock solution and Derivatisation-Negative Control solution were obtained commercially and required 1:10 dilution in dH20, Neuralisation Solution was taken and applied directly from the assay kit.

| 1 X PBS-T | (1 L) |
|---|---|
| 10 X PBS | 100 ml |
| Tween 20 | 0.5 ml |
| dH2O | 899.5 ml |

Blocking Dilution/Buffer (1 L)

| 1 X PBS-T | 1000 ml |
|---|---|
| BSA | 10 g |
| Adjust pH to | ~7.4 |

The assay was performed as follows:

5 μl of the sample (two aliquots per sample, as duplicate required, one for derivitisation reaction, the other for the negative control) from previously-diluted 20 μl aliquots of (A8) and control samples set aside for carbonyl assay (diluted to produce a 4 μg/μl protein concentration for both SN and pellet).

Standard concentrations were prepared according to the bovine serum albumin (BSA) band dinitrophenyl (DNP) concentration given (2.5 μl of standard solution from kit=100 fM of DNP of BSA band). Made up following standards based on above information: 200, 150, 100, 50, 25, 12.5 fM DNP, PBS (0fM)
200 fM standard=50 standard stock solution provided in kit
150 fM standard=3.75 standard stock solution+1.25 µl PBS (pH 7.4)
100 fM standard=2.5 µl standard stock solution+2.5 µl PBS All other standards were made by serial 1:1 dilution of a 100 fM solution (5 µl) with PBS. Standards were prepared identically to the derivatised samples (no negative control for the standards was employed).
Added the following solutions to sample/control, in the following order:
   5 µl of 12% SDS (diluted in dH2O)
   Either: 10 µl of DNPH (dinitrophenylhydrazine; reaction mixture) OR 10 µl of Derivitisation-Control solution (negative control)
   7.5 µl Neutralisation solution
Total=27.5 µl mixture per sample.

12% SDS was added to samples on ice, after which samples were all treated at room temp. DNPH was added, samples were incubated for 15 min then Neuralisation solution was added. Samples containing DNPH turned an orange colour upon addition of Neutralisation solution, whereas Derivatisation-control samples remained clear.

A further 5 µl of PBS was added to each sample to decrease viscosity.

The dot-blotting device had a 96-well plate installed to collect the sample on the bottom, and a pre-soaked (PBS) nitrocellulose membrane (14 cm×9 cm) fitted and sealed between the soft plastic thin layer and the topmost hard plastic layer. The standards and samples were all loaded onto the dot-blot plate before switching on the suction pump at maximum force (~19.3).

The membrane was placed in blocking buffer (40 ml) for 1 hr, rinsed twice briefly with PBS-T. Blot was then incubated with primary antibody from the kit (rabbit anti-DNP; 1:150 dilution in PBS-T, 134 µl antibody in ~20 µl PBS-T) for one hour, then washed twice immediately, followed by 2×15 min and 2×5 min washes with PBS-T. Further incubated with secondary antibody 1:300, 67 µl in 20 µl (goat anti-rabbit IgG-HRP) then rinsed again as described for post-primary antibody step. Blot was developed by incubating in chemiluminescence detection reagent (GE) 4 ml reagent 1:4 ml reagent 2 for 2 min.

Figure 9:
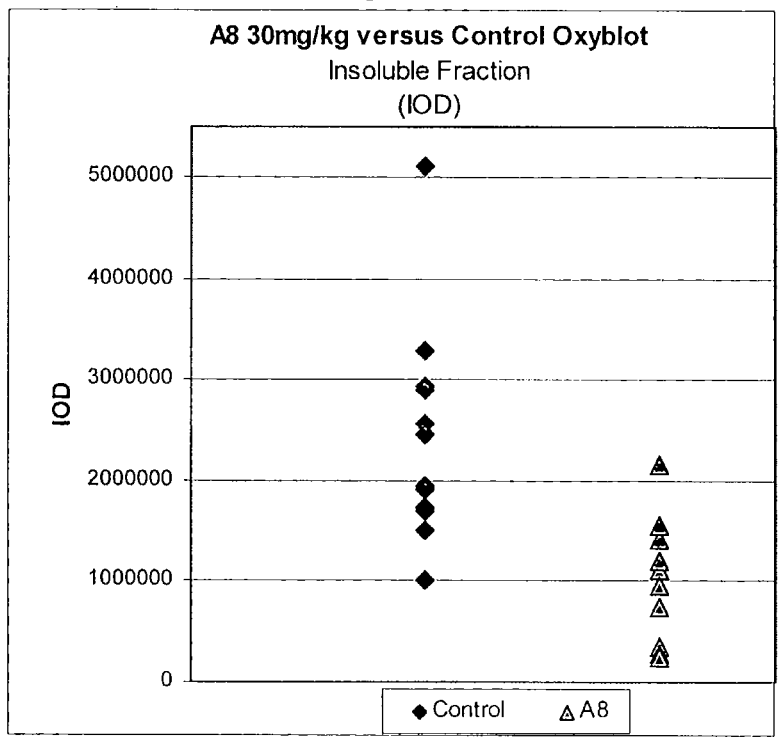
FIG. 9: illustrates the results of the Oxyblot™ assay for the insoluble mouse brain fraction versus control for complex A8.
Figure 10:
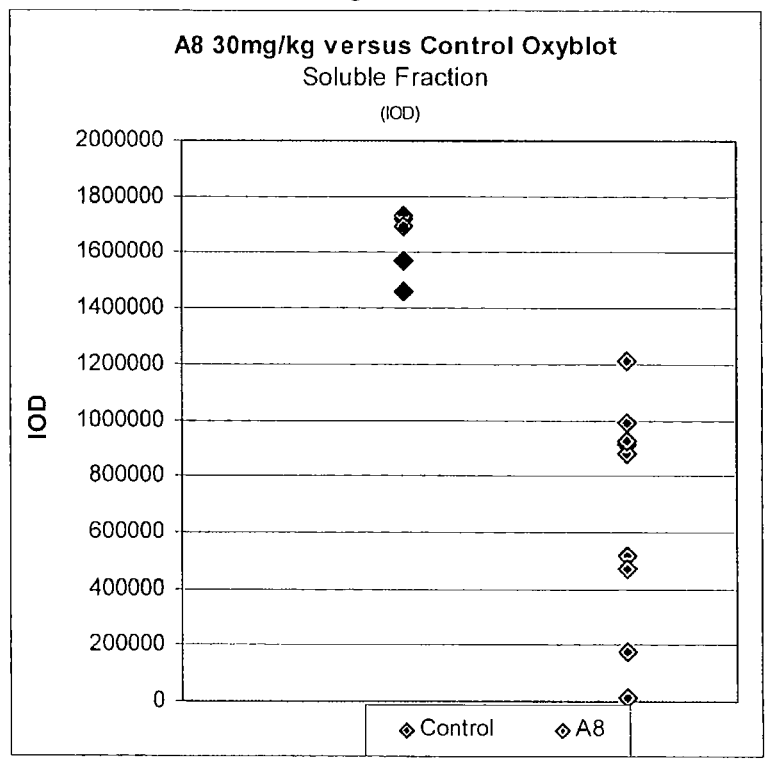
FIG. 10: illustrates the results of the Oxyblot™ assay for the soluble mouse brain fraction versus control for complex A8.

Membrane were captured using the "LAS-3000" (Fujifilm) image capturing system at 4 min capture time at the high setting (auto exposure). Using the Multi Gauge V2.3 software program, 100 (optical density) of the dot blot was calculated. Used the derivatised DNP PBS sample as background. Performed statistics comparing sham versus treatment group using "t-Test: Two-Sample Assuming Unequal Variances" for IOD values. The results of the oxidation assay as discussed above are shown in FIGS. 4 and 5 and Table 4 There was a significant decrease in DNP (carbonyls) in both insoluble and soluble brain fractions of A8-treated mice compared to control group (p=0.001 and p<0.001 respectively). The results are given in Table 5 and FIGS. 9 and 10.

TABLE 5

| Exp No. | Start Age yy mm dd | End Age yy mm dd | Identification | Insoluble Fraction IOD 4 min | Soluble Fraction IOD 4 min |
|---|---|---|---|---|---|
| 1 | 01-01-21 | 01-03-23 | Control | 2928819.1 | 3658003 |
| 2 | 01-01-21 | 01-03-23 | Control | 2565788.1 | 1718086 |
| 3 | 01-01-21 | 01-03-23 | Control | 1504266.1 | 1732442 |
| 4 | 01-01-15 | 01-03-18 | Control | 1007009.1 | 1694023 |
| 5 | 01-01-15 | 01-03-17 | Control | 1730518.1 | 3193021 |
| 6 | 01-01-22 | 01-03-17 | Control | 5105383.1 | 4081782 |
| 7 | 01-01-22 | 01-03-22 | Control | 1690190.1 | 1569152 |
| 8 | 01-01-22 | 01-03-22 | Control | 1942335.1 | 2043031 |
| 9 | 01-01-22 | 01-03-22 | Control | 2905421.1 | 1457786 |
| 10 | 01-01-19 | 01-03-22 | Control | 3282780.1 | 2118132 |
| 11 | 01-01-03 | 01-03-03 | Control | 1912386.1 | 2438337 |
| 12 | 01-01-16 | 01-03-03 | Control | 2463515.1 | 3470839 |
| 13 | 01-01-21 | 01-03-23 | A8 | 1419393.1 | 909877.1 |
| 14 | 01-01-21 | 01-03-23 | A8 | 357259.11 | 924649.1 |
| 15 | 01-01-21 | 01-03-23 | A8 | 1555864.1 | 513723.1 |
| 16 | 01-01-21 | 01-03-23 | A8 | 1115150.1 | 1214351 |
| 17 | 01-01-15 | 01-03-17 | A8 | 1203704.1 | 469925.1 |
| 18 | 01-01-06 | 01-03-08 | A8 | 737727.11 | 989478.1 |
| 19 | 01-01-06 | 01-03-08 | A8 | 960960.11 | 177146.1 |
| 20 | 01-01-14 | 01-03-16 | A8 | 2152486.1 | 13833.11 |
| 21 | 01-01-06 | 01-03-08 | A8 | 278327.11 | 878736.1 |
| 22 | 01-01-21 | 01-03-23 | A8 | 241186.11 | 928334.1 |

Statistical analysis of the raw data provided in Table 5 is given in Table 6.

TABLE 6

| | Insoluble Fraction | | Soluble Fraction | | |
|---|---|---|---|---|---|
| Parameter | Control | A8 (30 mg/kg) | Parameter | Control | A8 (30 mg/kg) |
| Mean | 1537800.07 | 972585.67 | Mean | 1609229.32 | 310756.97 |
| Variance | 3.4959E+11 | 3.6544E+11 | Variance | 7.72868E+11 | 1.799E+10 |
| Observations | 10 | 10 | Observations | 12 | 10 |
| Hypothesized Mean Difference | 0 | | Hypothesized Mean Difference | 0 | |
| df | 18 | | df | 12 | |
| t Stat | 2.11372856 | | t Stat | 5.046473186 | |
| P(T <= t) one-tail | 0.02437979 | | P(T <= t) one-tail | 0.000143098 | |
| t Critical one-tail | 1.73406359 | | t Critical one-tail | 1.782287548 | |

TABLE 6-continued

| | Insoluble Fraction | | | Soluble Fraction | |
|---|---|---|---|---|---|
| Parameter | Control | A8 (30 mg/kg) | Parameter | Control | A8 (30 mg/kg) |
| P(T <= t) two-tail | 0.04875957 | | P(T <= t) two-tail | 0.000286197 | |
| t Critical two-tail | 2.10092204 | | t Critical two-tail | 2.178812827 | |

Example 20 Anti-Oxidant Activity of Cu GTSM

Figure 11:
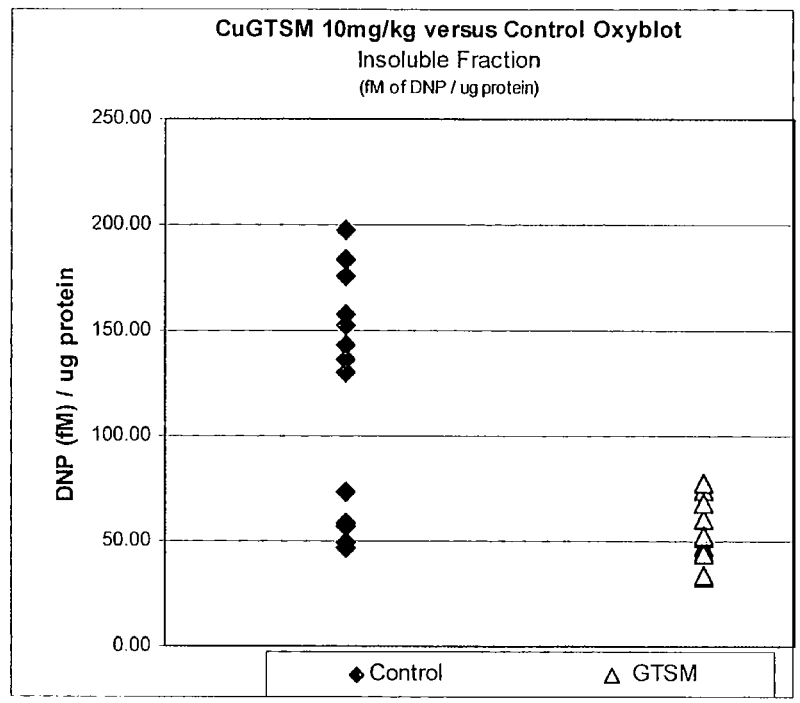
FIG. 11: illustrates the results of the Oxyblot™ assay for the insoluble mouse brain fraction versus control for complex CuGTSM.
Figure 12:
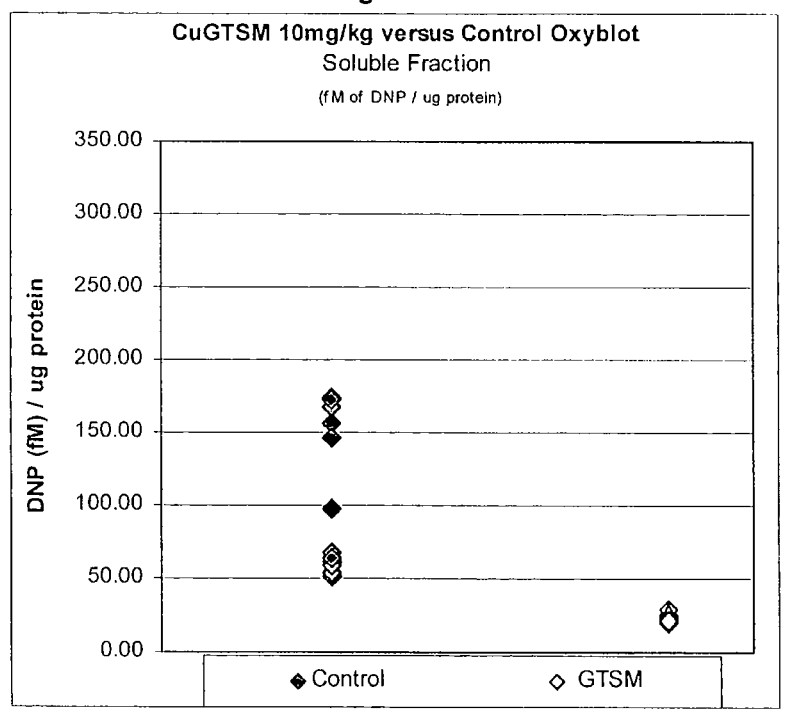
FIG. 12: illustrates the results of the Oxyblot™ assay for the soluble mouse brain fraction versus control for complex CuGTSM.

The procedure of example 18 was followed with Cu GTSM being used as the test compound. In all other respects the test procedure was the same. The results are provided in Table 7 and FIGS. 11 and 12.

TABLE 7

| Mouse No. | Start Age yy mm dd | End Age yy mm dd | Code | Insoluble relative fM DNP/ug protein | Soluble relative fM DNP/ ug protein |
|---|---|---|---|---|---|
| 1 | 00-03-02 | 00-05-01 | Control | 175.69 | 173.72 |
| 2 | 00-04-25 | 00-06-24 | Control | 143.35 | 155.74 |
| 3 | 00-03-29 | 00-05-28 | Control | 183.76 | 97.63 |
| 4 | 00-03-28 | 00-05-27 | Control | 197.60 | 58.68 |
| 5 | 00-03-10 | 00-05-09 | Control | 152.17 | 146.56 |
| 6 | 00-03-03 | 00-05-02 | Control | 130.44 | 167.19 |
| 7 | 00-03-01 | 00-04-30 | Control | 157.60 | 172.96 |
| 8 | 00-04-30 | 00-06-13 | Control | 136.15 | 61.15 |
| 9 | 00-04-30 | 00-06-13 | Control | 58.45 | 50.82 |
| 10 | 00-04-30 | 00-06-13 | Control | 57.01 | 54.07 |
| 11 | 00-04-30 | 00-06-13 | Control | 46.83 | 58.9 |
| 12 | 00-04-30 | 00-06-13 | Control | | |
| 13 | 00-05-03 | 00-06-16 | Control | 49.55 | 67.00 |
| 14 | 00-04-30 | 00-06-13 | Control | 72.96 | 64.12 |
| 15 | 00-05-03 | 00-06-16 | Control | | |
| 16 | 00-05-03 | 00-06-16 | Control | | |
| 17 | 00-04-08 | 00-06-26 | Cu-GTSM | 74.21 | 24.86 |
| 18 | 00-04-08 | 00-06-26 | Cu-GTSM | 32.85 | 21.33 |
| 19 | 00-04-08 | 00-06-26 | Cu-GTSM | 60.29 | 22.48 |
| 20 | 00-03-29 | 00-06-16 | Cu-GTSM | | |
| 21 | 00-03-29 | 00-06-16 | Cu-GTSM | 51.64 | 19.83 |
| 22 | 00-03-29 | 00-06-16 | Cu-GTSM | 33.49 | 21.43 |
| 23 | 00-03-12 | 00-05-30 | Cu-GTSM | 47.76 | 22.72 |
| 24 | 00-03-12 | 00-05-30 | Cu-GTSM | | |
| 25 | 00-04-06 | 00-06-24 | Cu-GTSM | 44.95 | 20.49 |
| 26 | 00-04-06 | 00-06-24 | Cu-GTSM | 67.91 | 28.42 |
| 27 | 00-04-06 | 00-06-24 | Cu-GTSM | 43.57 | 24.15 |
| 28 | 00-04-06 | 00-06-24 | Cu-GTSM | 52.85 | 26.42 |
| 29 | 00-03-29 | 00-06-16 | Cu-GTSM | 77.9 | 20.8 |

The statistical analysis of the data provided in Table 7 is provided in Table 8.

TABLE 8

| | Insoluble Fraction | | | Soluble Fraction | |
|---|---|---|---|---|---|
| Parameter | Control | Cu-GTSM (10 mg/kg) | Parameter | Control | Cu-GTSM (10 mg/kg) |
| Mean | 120.12 | 53.4018182 | Mean | 102.1953846 | 22.993636 |
| Variance | 3069.82913 | 231.326996 | Variance | 2691.710377 | 7.2646055 |
| Observations | 13 | 11 | Observations | 13 | 11 |
| Hypothesized Mean Difference | 0 | | Hypothesized Mean Difference | 0 | |
| df | 14 | | df | 12 | |
| t Stat | 4.16038659 | | t Stat | 5.495418509 | |
| P(T <= t) one-tail | 0.00048095 | | P(T <= t) one-tail | 6.86308E-05 | |
| t Critical one-tail | 1.76131012 | | t Critical one-tail | 1.782287548 | |
| P(T <= t) two-tail | 0.0009619 | | P(T <= t) two-tail | 0.000137262 | |
| t Critical two-tail | 2.14478668 | | t Critical two-tail | 2.178812827 | |

Example 21 Effect of Compounds on Tau Phosphorylation

To compare the levels of Soluble (SN) and insoluble (pellet) phospho-Tau (p-396) from Cu-GTSM (10 mg/kg) treatment group compared to the Control group as shown in Table 9. These are double transgenic APP/PS1 mice, male and female.

Summary of SN and Pellet Preparation:

TABLE 9

| Treatment group | AT No | No of mice in trial | No of mice completed trial | No of mice died | % survival rate | Average End Age yy mm dd |
|---|---|---|---|---|---|---|
| Control | n/a | 9 | 9 | 0 | 100% | 00 06 14 |
| Cu(GTSM) | n/a | 14 | 13 | 1 | 93% | 00 06 18 |

At the completion of the trial the RHS of the brain including the cerebellum was collected, recorded the wet weight and placed in a Beckman labelled ultracentrifuge tube. This brain sample is used to test the levels of Abeta and metal in the Supernatant (SN) and Pellet homogenate.

Preparation of Brain SN and Pellet Homogenate for CuGTSM & Control

Briefly, 1 ml of PBS pHed to 7.4 (without Ca and Mg, Sigma D-8537, containing one Complete® EDTA-free protease inhibitor Tablet per 50 ml PBS) and 10 ul of butylated hydroxytoluene 0.5M stock solution in acetonitrile was added to each sample, sonicated at 40% intensity for 2×10s bursts, or until homogenised. Samples were on ice at all times. 1 ml of the homogenate was transferred to new tube and ultracentrifuged at ~100,000 g, hence 47K rpm in the optimax using the TLA55 rotor for 30 min at 4° C. Collected supernatant (SN) (only clear ART tips were used at all times), resuspended pellet in further 1 ml PBS and 10 ul BHT (0.5M), sonicated until homogeneous mixture was obtained. Remainder of homogenate (<50 ul) was frozen at −20° C.

Aliquoted for Pellet:
350 μl—ICPMS; 20 μl—BCA assay; 20 μl—Western Blot assay; 2×20 μl aliquots for carbonyl Oxyblot assay.

Aliquoted for SN:
500 μl—ICPMS; 20 μl—BCA assay; 20 μl—Western Blot assay; 2×20 μl aliquots for carbonyl Oxyblot assay.

Determination of Protein Levels for all Samples:
Used the BCA assay kit (Pierce) to determine the protein concentration of the pellet and SN samples.

A 20 ul aliquot of Pellet and SN were diluted 1:10, i.e. added 180 μl of PBS. Determined protein concentration as per BCA assay method. The Absorbance levels were around the 0.3-0.9 Abs. Using the excel program determined the volume of PBS required to make a stock solution of: 3 μg/μl of protein of SN and a 0.2 μg/μl of protein of Pellet using the 20 μl aliquots.

Preparation of Samples for Westerns Blotting:
In summary, compared the treatment group CuGTSM to the control for both the soluble (SN) and Insoluble (pellet) samples. In total 2 Biorad Criterion 4-12% Bis-Tris 26-well gels were prepared.

Once the Protein content of each sample was determined by the BCA assay a 3 μg of protein/μl sample of SN and the 0.2 μg of protein/μl sample of pellet was prepared. A 15 μl aliquot of the 3-μg/ul stock solution of the SN and the 0.2 μg/ul stock solution of the pellet was taken to make up a 45 and 3 μg protein/lane sample, respectively. Added 5 μl of SB×4 containing 10% mercaptoethanol to each 15 μl sample. (For pellet, n=24 ssamples, for SN n=22 samples).

Heated the samples for 5 min at 90° C. Pulse spun the samples for ~10 sec. Loaded samples on 4-12% Bis-tris gels, 26 well gels (Criterion Gel, BioRad). Ran gels @ 110V for 75 min, then @ 130V for 50 min, rm temp. Transferred gels at @ 40V for 60 min, at 4° C. Heated membrane for 5 mins in 1×PBS (preheated) in microwave. Blocked membrane for 1 hour in 5% skim milk in TBST at room temp.

Probed with primary antibody overnight: rabbit anti-phospho-Tau (BioSource; 1:1000, 30 ul/30 ml, 15 ml per blot) in TBST at 4° C. Following day, washed blots ~6×10 min with TBST. Probed with secondary antibody for 1 hour at room temp: anti rabbit HRP (DAKO) 1:5000 diluted in TBST (8 ul/40 ml, 20 ml per blot).

Washed blots for 6×10 min with TBST. Used ECL reagent (Amersham) to develop blots (8 ml per blot, 1:1 ratio reagent A and B). Incubated the blots in ECL for 2 min.

All the membranes were captured using the "LAS-3000" (Fujifilm) image capturing system at 2 min capture time at the high setting for blot 1 (pellet) and 8 s gel 2 (SN; also once manually exposed for 3 min, high setting). The trimeric bands (combined), appearing between ~49 and 62 kDa, were quantitated using the Multi Gauge V2.3 software program. The images have been stored on file for future reference and a print out has been prepared in power point File "Western Phspho-Tau Images 14-11-06). e IOD (optical density) was used to compare treated and control groups for relative levels of phospho-Tau present.

Performed statistics comparing sham versus treatment group using "t-Test: Two-Sample Assuming Unequal Variances" for IOD for both pellet and SN samples.

Figure 13:
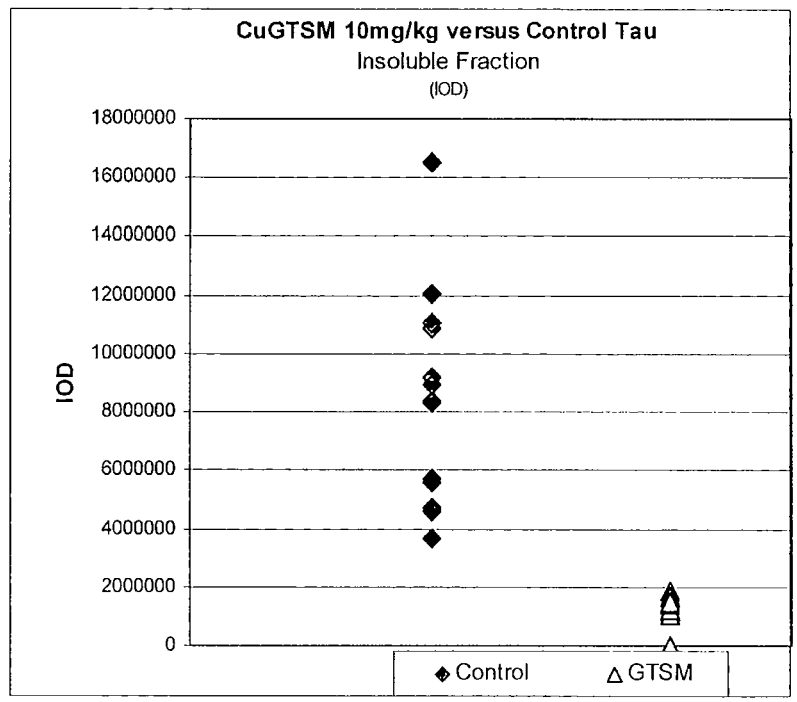
FIG. 13: illustrates the results of a tau phosphorylation assay for the insoluble mouse brain fraction versus control for complex CuGTSM.
Figure 14:
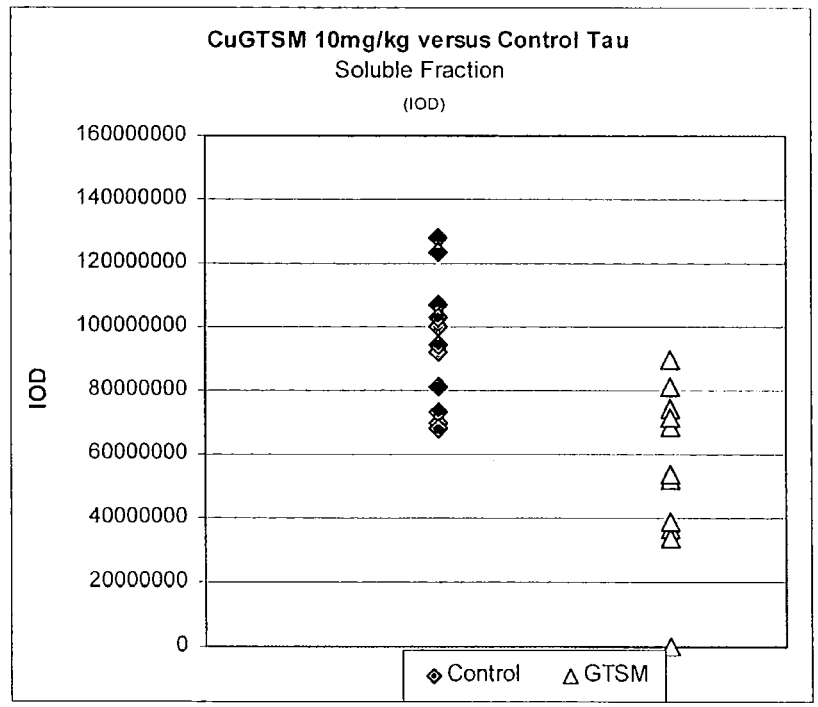
FIG. 14: illustrates the results of a tau phosphorylation assay for the soluble mouse brain fraction versus control for complex CuGTSM.

The results were shown in Table 10 and FIGS. 13 and 14

TABLE 10

| Mouse No | Start Age yy mm dd | End Age yy mm dd | Code | Insoluble Fraction Phospho-Tau p-396 IOD | Phospho-Tau p-396 IOD |
|---|---|---|---|---|---|
| 1 | 00-03-02 | 00-05-01 | Control | 10831328.61 | 69853169.82 |
| 2 | 00-04-25 | 00-06-24 | Control | 8353024.09 | 100136407.8 |
| 3 | 00-03-29 | 00-05-28 | Control | 11024896.87 | 92012735.29 |
| 4 | 00-03-28 | 00-05-27 | Control | 9164050.65 | 94323290.82 |
| 5 | 00-03-10 | 00-05-09 | Control | 16508335.65 | 80946528.20 |
| 6 | 00-03-03 | 00-05-02 | Control | 8289077.87 | 73140488.21 |
| 7 | 00-03-01 | 00-04-30 | Control | 12013744.43 | 68189827.36 |
| 8 | 00-04-30 | 00-06-13 | Control | 8912742.37 | 128130770.3 |
| 9 | 00-04-30 | 00-06-13 | Control | 4701385.34 | 107130713.2 |
| 10 | 00-04-30 | 00-06-13 | Control | 4562458.65 | |
| 11 | 00-04-30 | 00-06-13 | Control | 5697896.21 | |
| 12 | 00-05-03 | 00-06-16 | Control | 5599566.21 | 102959537.7 |
| 13 | 00-04-30 | 00-06-13 | Control | 3643456.95 | 123262249.3 |
| 14 | 00-04-08 | 00-06-26 | Cu-GTSM | 1477928.37 | 74533337.44 |
| 15 | 00-04-08 | 00-06-26 | Cu-GTSM | 1065622.78 | 68679994.36 |
| 16 | 00-04-08 | 00-06-26 | Cu-GTSM | 1856749.43 | 36374522.21 |
| 17 | 00-03-29 | 00-06-16 | Cu-GTSM | Non Tg | Non Tg |
| 18 | 00-03-29 | 00-06-16 | Cu-GTSM | 1202317.09 | 36602406.27 |
| 19 | 00-03-29 | 00-06-16 | Cu-GTSM | 1891529.65 | 33773474.29 |
| 20 | 00-03-12 | 00-05-30 | Cu-GTSM | 1082151.43 | 51807875.36 |
| 21 | 00-03-12 | 00-05-30 | Cu-GTSM | Non Tg | Non Tg |

TABLE 10-continued

| Mouse No | Start Age yy mm dd | End Age yy mm dd | Code | Insoluble Fraction Phospho-Tau p-396 IOD | Phospho-Tau p-396 IOD |
|---|---|---|---|---|---|
| 22 | 00-04-06 | 00-06-24 | Cu-GTSM | 1687976.43 | 81127942.21 |
| 23 | 00-04-06 | 00-06-24 | Cu-GTSM | 1433094.43 | 53916728.13 |
| 24 | 00-04-06 | 00-06-24 | Cu-GTSM | 1237435.43 | 38578309.13 |
| 25 | 00-04-06 | 00-06-24 | Cu-GTSM | 1453283.71 | 71563860.21 |
| 26 | 00-03-29 | 00-06-16 | Cu-GTSM | 1470088.65 | 89976911.06 |

A statistical analysis of the data given in Table 10 is provided in Table 11.

TABLE 11

| | Insoluble Fraction | | | Soluble Fraction | |
|---|---|---|---|---|---|
| Parameter | Control | Cu-GTSM (10 mg/kg) | Parameter | Control | Cu-GTSM (10 mg/kg) |
| Mean | 6879494.38 | 3085357.57 | Mean | 94553247 | 57903214.61 |
| Variance | 1.4055E+13 | 2.0847E+13 | Variance | 4.17E+14 | 4.07337E+14 |
| Observations | 13 | 11 | Observations | 11 | 11 |
| Hypothesized Mean Difference | 0 | | Hypothesized Mean Difference | 0 | |
| df | 19 | | df | 20 | |
| t Stat | 2.19923513 | | t Stat | 4.234461 | |
| P(T <= t) one-tail | 0.02022171 | | P(T <= t) one-tail | 0.000203 | |
| t Critical one-tail | 1.72913279 | | t Critical one-tail | 1.724718 | |
| P(T <= t) two-tail | 0.04044342 | | P(T <= t) two-tail | 0.000407 | |
| t Critical two-tail | 2.09302405 | | t Critical two-tail | 2.085963 | |

Example 22 Bioavailability Data

Non transgenic (non-Tg) (BL/6xSJL) Tg APP2576 (−) female mice aged ~12-14 months were selected fro the bioavailability trial. For each drug, four mice were orally administered either 5 or 30 mg/kg. On the last day (day 7 for Cu compounds) mice received the regular drug dose spiked with the radiolabelled Cu-64 or Zn-65 analogue. Radiolabeled compounds were prepared by standard protocols (P. S. Donnelly, O. Golovko, J. M. Heslop, P. Burke, J. C. Clark, J. R. Dilworth, F. I. Aigbirhio, *J. Label. Compd. Radiopharm.*, 2005, 48, S163).

Bioavailability of the drug was given by measuring radioactivity of tissue samples. Duration: Compounds were orally administered by gavage for 7 or 8 consecutive days
Vehicle: SSV pH6.3

Drug preparation: Dosage volume set at 100 μl for a 25 g mouse or 4 times the mouse weight.
Drug dosage is 5 mg/kg. The results of the bioavailability study are provided in Table 12 with a results summary being given in Table 13.

TABLE 12

| Mouse | Cmpd | Blood (CPM) | Liver (CPM) | (Brain CPM) | Blood (Vol) | Liver (g) | Brain (g) |
|---|---|---|---|---|---|---|---|
| 1 | A8 | 7925 | 38985 | 516 | 1.0 | 0.27 | 0.45 |
| 2 | A8 | 6932 | 46158 | 486 | 1.0 | 0.37 | 0.30 |
| 3 | A8 | 34644 | 170710 | 1998 | 1.0 | 0.43 | 0.22 |
| 4 | A8 | 11363 | 78729 | 952 | 1.0 | 0.29 | 0.40 |
| 5 | A16 | 4626 | 122655 | 966 | 1.0 | 0.38 | 0.49 |
| 6 | A16 | 356 | 2892 | 162 | 1.0 | 0.21 | 0.37 |
| 7 | A16 | 5908 | 81209 | 627 | 1.0 | 0.24 | 0.37 |
| 8 | A16 | 5664 | 84918 | 773 | 1.0 | 0.20 | 0.42 |
| 9 | A23 | 5643 | 99907 | 1084 | 1.0 | 0.21 | 0.37 |
| 10 | A23 | 5242 | 56261 | 7667 | 1.0 | 0.30 | 0.42 |
| 11 | A23 | 5298 | 30958 | 427 | 1.0 | 0.19 | 0.41 |
| 12 | A23 | 115 | 1341 | 36 | 1.0 | 0.20 | 0.36 |

Standards
A8 = 2397203 cpm
A16 = 2794850 cpm
A23 = 1901062 cpm

TABLE 13

| | Blood (% ID) | Liver (% ID) | Brain (% ID) |
|---|---|---|---|
| Mouse 1 | 0.33 | 6.14 | 0.05 |
| Mouse 2 | 0.29 | 5.20 | 0.07 |
| Mouse 3 | 1.45 | 16.72 | 0.38 |
| Mouse 4 | 0.47 | 11.36 | 0.10 |
| Mean for A8 | 0.63 | 9.86 | 0.15 |
| Mouse 5 | 0.17 | 11.61 | 0.07 |
| Mouse 6 | 0.01 | 0.50 | 0.02 |
| Mouse 7 | 0.21 | 11.96 | 0.06 |
| Mouse 8 | 0.20 | 14.97 | 0.07 |
| Mean for A16 | 0.19 | 12.84 | 0.07 |
| Mouse 9 | 0.30 | 24.79 | 0.15 |
| Mouse 10 | 0.28 | 9.74 | 0.96 |
| Mouse 11 | 0.28 | 8.80 | 0.05 |
| Mouse 12 | 0.01 | 0.35 | 0.01 |
| Mean for A23 | 0.28 | 14.44 | 0.39 |

Example 23 BTSC-Metal Complexes Activate PI3K and JNK-Dependent Pathways Resulting in Increased Degradation of Secreted Aβ1-40

APP-CHO cells were treated with 10 μM metal-BTSC complexes for 6 hr. Cells were extracted into Phosphosafe (Novagen) lysis buffer and proteins separated by gel-electrophoresis on 12% tris-glycine gels. Proteins were transferred to PVDF membranes and blocked with milk powder for 1 hr. Blots were then probed for total and phosphorylated forms of Akt, JNK and GSK3 using antibodies from Cell Signaling Technologies. After detection with secondary antisera (HRP-labelled), blots were analysed for signals using chemiluminescence analysis on a GeneGnome image scanner. Activation of PI3K is shown by increased levels of phosphorylated Akt (p-Akt). Activated JNk is shown by increased p-JNK. Increased levels of deactivated GSK3 is shown by increased p-GSK3.

APP-CHO cells were treated with 10 µM [Zn(ATSE)] with or without specific inhibitors of PI3K (LY294002), JNK (SP600125) or p38 (SB203580) (25 µM of each) for 6 hr and conditioned medium analysed for levels of Aβ1-40 by routine ELISA. Inhibition of JNK by SP600125 prevented the loss of Aβ by [Zn(ATSE)]. Inhibition of PI3k by LY294002 prevented the loss of Aβ by [Zn(ATSE)].

Example 24 Y-Maze Behavioural Data

In order to test the efficacy of the metal complexes a Y-maze behaviour trial was conducted on double transgenic APP/PS1 mice. The procedure used was as follows:
Set-Up
A Y maze was set up with the arms labelled. The floor of the maze was covered with sawdust evenly in all 3 arms (used saw-dust for black mice and fibre-cycle for agouti mice. Each mouse to be used in the trail was then randomly allocated a starting and blocked arm.
Testing
At the start of each experiment labels were placed next to the maze denoting the mouse ID number and the date. The closed arm of the maze was then blocked using the designated wall insert and the recording started on the video. The mouse was placed in its' starting arm facing the wall making sure the required arm is blocked and allowed to explore the maze for 10 minutes. The mouse was then removed from the maze for a period of for 60 minutes during which time the wall insert was removed to unblock the blocked arm of the maze. At the completion of the 60 minute waiting period the mouse was again placed in the maze facing the wall, back in the same starting arm, however, this time with no arms blocked. The mouse was allowed to explore for 5 minutes then removed. Between each mouse insertion the sawdust was mixed within the maze.
Analyzing
The video data was then analysed computationally to determine the period that each mouse spent in each arm of the maze in the first incursion and in the second incursion.

24 mice double transgenic APP/PS1 mice were split randomly into two groups of 12. Mice in each group. The first group was subjected to a control or sham dosage whereas the second group was treated with CuGTSM at a dosage of 10 mg/kg. The results are shown in table 14.

TABLE 14

Y-Maze Data

| Treatment | % Visit to Novel arm | % Visit to Start Arm | % Visit to Other Arm |
|---|---|---|---|
| Control | 33.2 | 30.7 | 36.1 |
| CuGTSM/10 mg/kg. | 47.9 | 29.7 | 22.4 |

In normal mice the normal response is that upon being re-trialled (i.e with the novel arm un-blocked) mice will spend a significantly greater proportion of time in the novel arm in comparison with the start arm and the other arm. Thus typically the mice will spend their time 50%, 25%, 25%. In contrast if the percentage of time or number of visits is around equal the results are interpreted that the mice had no memory of the initial experience and hence did not recognize the novel arm as such. The above results therefore clearly indicate that the mice treated with CuGTSM had significant memory improvement in comparison with the control mouse.

Example 25 CuGTSM Inhibition of GSK3β

Figure 15:
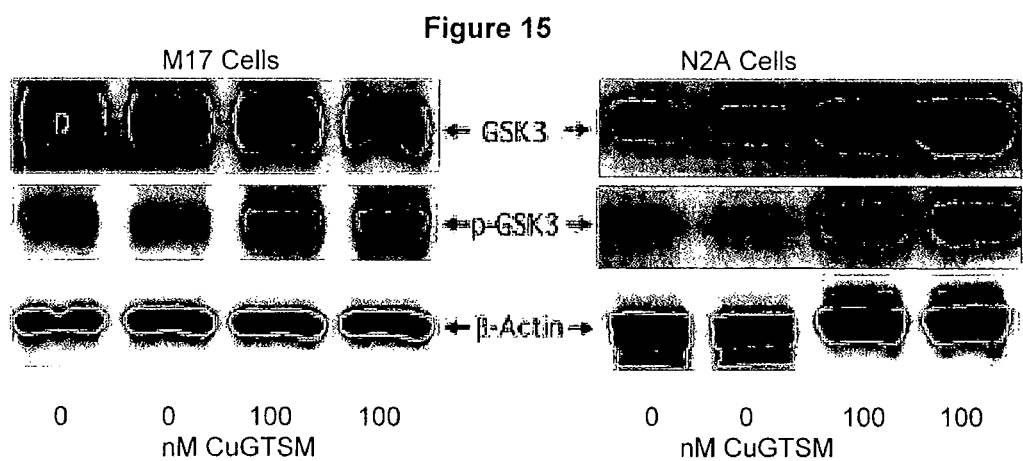
FIG. 15: Shows GSK3β and phosphorylated GSK3β (p-GSK3β) levels in M17 and N2a cells treated with CuGTSM or vehicle control for 24 hours. GSK3β in inhibited when phosphorylated, therefore treatment with CuGTSM is shown to inhibit GSK3β activity in M17 and N2a cells. B-actin is shown as a control.

In order to clearly show that the metal complexes described inhibit GSK3β two sets of cell samples M17 (human) or N2a (murine) neuroblastoma cells were plated at a passaging ratio of 1:4 from a 90% confluent flask of cells and grown until 80-90% confluent. Medium was replaced with fresh serum-free OptiMem and cells were exposed to 1 or 100 nM CuGTSM (from 10 mM stock in DMSO) for 18 hr (overnight). Medium was removed and cells extracted into Phosphosafe (Invitrogen) extraction buffer and frozen at −80° C. Western blots were performed on cell lysates for total GSK3β and phospho-GSK3α/β (Cell Signaling Technology). The blots revealed that GSK3α/β was robustly phosphorylated by treatment with CuGTSM compared to control cells treated with vehicle (DMSO) alone. The phosphorylation of GSK3α/β induces inhibition of GSK3 activity. As GSK3 is known to induce phosphorylation of tau (an important pathological marker in AD), the inhibition of GSK3 activity by CuGTSM would be expected to inhibit tau phosphorylation. The results are shown in FIG. 15.

Example 26 Effect of Metal Complexes Such as CuGTSM as Antioxidants in a Parkinsons's Disease Model A series of trials were conducted in which the effect of CuGTSM on inhibiting Dopamine induced cell death were conducted on WT cells and A30P cells. The protocol used was as follows.
Cell Culture
The cell line was maintained in OPTI-MEM (Gibco) supplemented with 10% foetal calf serum (FCS), Non-essential amino acids, sodium pyruvate and Penn/Strep. Cells were incubated at 37° C. in a humidified atmosphere of 95% air and 5% $CO_2$. Cell assays were plated out into 48 well culture plates at 4×10 4 cells per well. Cells were left to settle overnight then incubated with drugs for 24 h prior to being subjected to MTT assays for cell viability.
MTT Assay for Determination of M17 Cell Viability
The viability of cells was assessed using an MTT assay. Active mitochondria convert the yellow MTT tetrazolium salt to purple formazan which can be measured by a spectrophotometer as described in methods previously (Mossman 1983). The mixture of media and reagents e.g. Dopamine was aspirated off and media containing 5 mg/ml MTT is added and the plate incubated for 1 h at 37° C. The remaining media/MTT solution is aspirated off and the cells were then solubilised with DMSO. The 48 well plate is then read at 595 nm on a plate reader.

In essence a series of WT cells and A30P cells were treated with a control, Dopamine, CuGTSM, Cu ATSM, and combinations of Dopamine and CuGTSM, and dopamine and CuATSM at various concentrations to determine the ability of the compound to act as an anti-oxidant and mediate cell death. The results are shown in table 15 (WT cells) and Table 16 (A30P cells)

TABLE 15

| WT Cells | |
|---|---|
| Treatment | % recovery |
| Dopamine 500 μm + CuGTSM 0.1 μM | −34.57 |
| Dopamine 500 μm + CuGTSM 0.01 μM | 36.03 |
| Dopamine 500 μm + CuATSM 0.1 μM | 103.13 |
| Dopamine 500 μm + CuATSM 0.01 μM | 64.28 |

TABLE 16

| A30P cells | |
|---|---|
| Treatment | % recovery |
| Dopamine 500 μm + CuGTSM 0.1 μM | 54.19 |
| Dopamine 500 μm + CuGTSM 0.01 μM | 97.85 |
| Dopamine 500 μm + CuATSM 0.1 μM | 97.77 |
| Dopamine 500 μm + CuATSM 0.01 μM | 105.90 |

Figure 16:
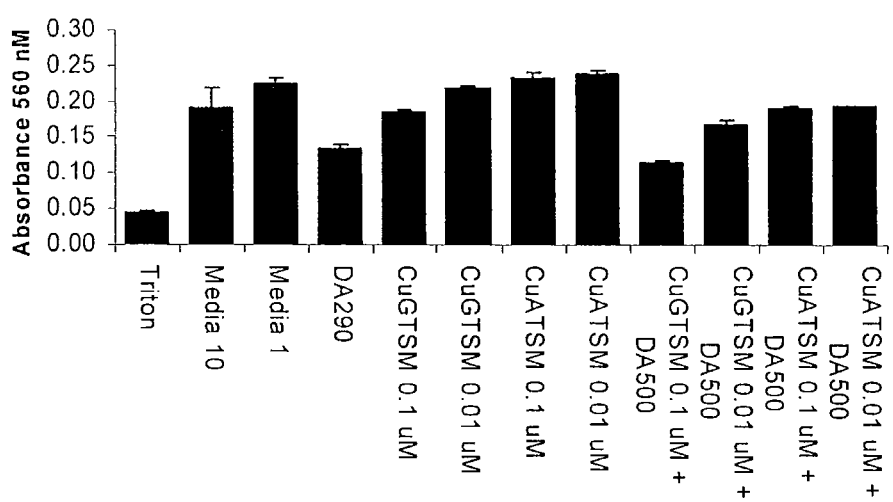
FIG. 16: Shows the effect of various BSTC's on Dopamine induced WT cell death.
Figure 17:
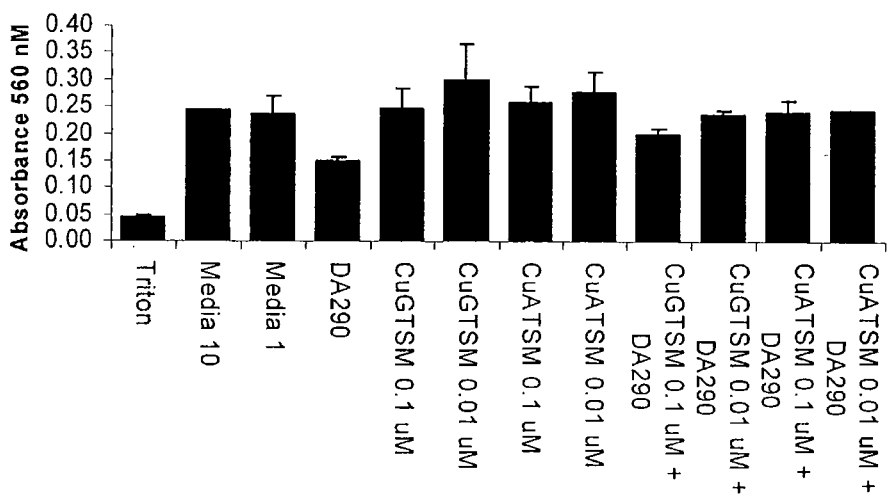
FIG. 17: Shows the effect of various BSTC's on Dopamine induced A30P cell death.

The results clearly show the ability of the complexes to act as anti-oxidants and to lead to cell recovery. The results are shown graphically in FIG. 16 and FIG. 17.

Example 27 Ability of Complexes to Treat Mice with Induced Parkinsons Disease

6-OHDA Toxin Lesioning

A partial lesion of the SNpc was produced in the mice by injecting the neurotoxin 6-OHDA into the right SNpc. The mouse was injected with atropine (0.5 mg/kg) to reduce respiratory tract secretions together with xylazine (10 mg/kg) to produce sedation (intramuscular injection with a 27 gauge needle, 60 microliters). Mice were anesthetized with 4% chloral hydrate in PBS (10 ml/kg, i.p.), and heads were secured in a stereotaxic head frame with the bite bar 3 mm above horizontal. A 1.65 mg/ml solution of 6-OHDA was prepared with ascorbic acid (0.2 mg/ml) and kept on ice until the time of injection. A 10 ml Hamilton syringe (with a 26 gauge needle) mounted in a syringe pump (Cole-Parmer, Vernon Hills, Ill.) was inserted into the right SNpc through a small hole drilled through the top of the skull. A single injection (2.5 mg) of 6-OHDA (Sigma) was made into the right SNpc (anteroposterior, 3.0 mm; lateral, 1.05 mm; dorsoventral, 4.7 mm, with respect to lambda) (Franklin and Paxinos, 1997). On completion of the injection, the needle was left in place for 5 min then slowly withdrawn at a rate of 1 mm/min. After surgery, the skin was sutured, antiseptic (1% w/w iodine, Betadine; Faulding and Company, Salisbury, South Australia) was applied to the wound, and the mice were left in a warmed cage to recover. Paracetamol (100 mg/kg) was administered in drinking water as an analgesic after surgery.

Drug Feeding

Test drugs were suspended in standard suspension vehicle (SSV; NaCl 0.9% w/v, Na-CMC 0.05% w/v, Benzyl alcohol 0.05% v/v, Tween 80 0.04% v/v) and were delivered by oral gavage at a daily dosage of 10 or 30 mg/kg for 7 days pre lesion and then a period of 14 consecutive days post lesion (Chemy et al., 2001); controls received SSV alone.

Behaviour-Amphetamine-Induced Rotation

Rotation-this assay is only applicable to mice and rats that receive a unilateral injection of 6-OHDA to produce a partial lesion of nigral neurons. The lesioned rodent is placed in a bowl and videotaped for one hour, then injected with 5 mg/kg amphetamine Fourteen days after lesioning the mouse was connected to the automated Rotacount system (Columbus Instruments, Columbus, Ohio, USA). This records contralateral and ipsilateral rotations. The mouse is attached so that any movement clockwise or anti-clockwise is registered by a sensor that is then monitored and counted by a computer (SOFTWARE). Once connected baseline movement levels are established by leaving the rodent for 30 mins. The mice are then injected via an intraperitoneal injection of 5 mg/kg amphetamine (Sigma) and then the movement recorded for a further hour. Data from the sensors is then plotted and analysed.

Histology and TH Staining

Animals were killed by an overdose of sodium pentobarbitone (Lethobarb; 0.35 mg/gm) and perfused with 30 ml of warmed (37° C.) 0.1 M PBS, pH 7.4, with heparin (1 μml), followed by 30 ml of chilled 4% paraformaldehyde (Sigma, St. Louis, Mo.) and 0.2% picric acid in 0.1 M phosphate buffer (4° C.), pH 7.4. The brains were then removed and left at 4° C. overnight in 30% sucrose in PBS.

Sections were fixed in 100% ethanol for 15 min at 4 C. The sections were then air dried and rinsed with 0.1 M PBS before being incubated in blocking solution (3% NGS, 0.3% (v/v) Triton, 0.1 M PBS) for 15 min at RT. After 3 5 min washes with 0.1 M PBS the sections were incubated overnight at RT with rabbit anti-TH antibody (1:800 chemicon) in 1% NGS/0.3% Triton/0.1 M PBS. This was followed by a further washing step and by incubation of goat anti-rabbit IgG (1:300 SOURCE) in 1% NGS/0.3% Triton/0.1M PBS for 2 h at RT. The reaction was visualized with 3,3-diaminobenzidine tetrahydrochloride (DAB) for 15 min and then DAB with hydrogen peroxide for 5 min. Section are washed three times in 0.1M PBS for 10 min and then counterstained with Neutral Red (50 s).

Estimate of Lesion Size.

Stereological Estimates Cell Numbers

The total number of DA neurons in the SN were estimated using a fractionator sampling design [refs Finkelstein et al 2000, Stanic et al 2004 and West and Gendersen 1990]. Mice: brains are sectioned in a 1:3 series at 40 μm and immunohistochemistry performed for Nissl stained sections. Counts are made at regular predetermined intervals (×140 um, y 140 um). Systematic samples of the area occupied by the nuclei are made from a random starting point. An unbiased counting frame of known area (45 um×35 um) is superimposed on the image of the tissue sections.

Figure 18:
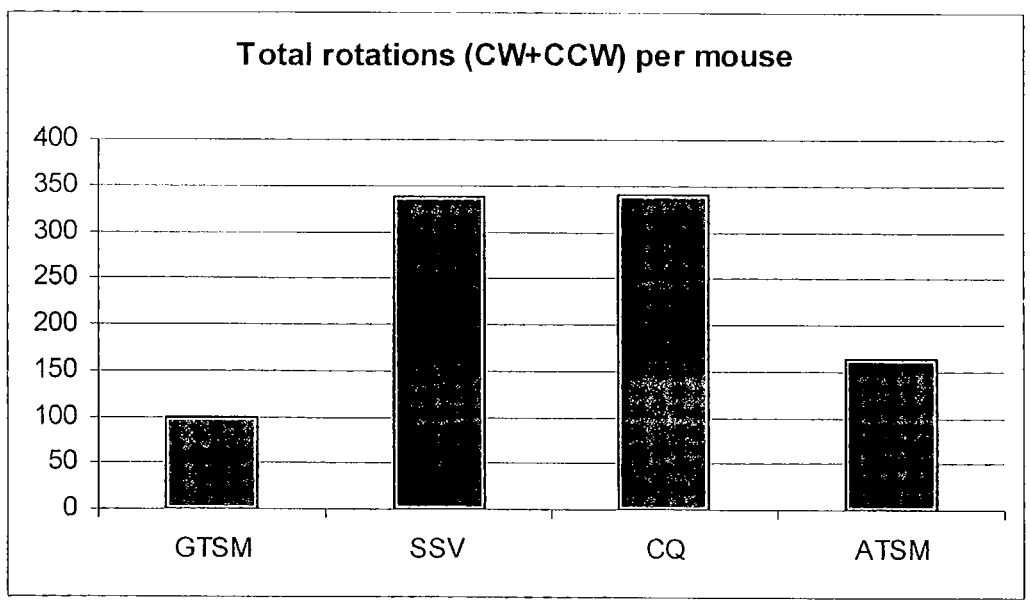
FIG. 18: Graphically illustrates the total rotations of control mice and mice treated with metal complexes in Parkinsons disease model.
Figure 19:
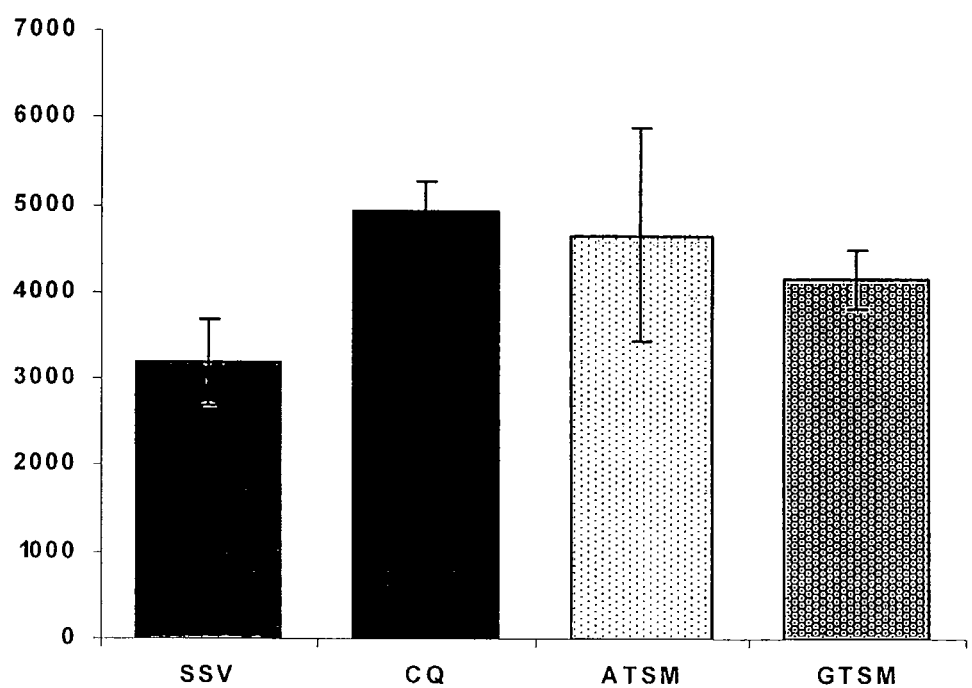
FIG. 19: Shows cell counts on post-mortem examination of the brains in the mice used in example 27

The results are clearly shown in FIG. 18 and show that compared to the control the treated mice were significantly less disoriented. The behavioural data therefore shows that the mice treated with either Cu(ATSM) or Cu(GTSM) performed better (ie less movement in a circular fashion) than did the control group. The circular motion in response to an amphetamine challenge is the result of death of the cells of the substantia nigra as a consequence of the lesion by 6-hydroxy dopamine. That the treated animals performed better is consistent with the drugs having a protective effect on the cells of the lesioned substantia nigra. This was confirmed by cell counts on post-mortem examination of the animals the results of which are shown in FIG. 19.

Example 28 Chemical Depletion of PrPc Using Metal Complexes

An experiment was carried out in which GT1-7 cells and HeLa cells were treated with a metal complex to determine the effect of the complex on the depletion of PrPc. This is significant as prion infectivity and toxicity is thought to be mediated by an interaction between the infectious PrPsc form and the endogenous normal cellular for PrPc. If PrPc is knocked down then the toxic/infectious PrPsc has nothing to interact with and therefore can do not induce a toxic response or pass on the infection. The protocol used was as follows:

GT1-7 Cells

The cells were plated onto 6 well plate and grown to ~70% confluency (maximum) before treatment. The OptiMEM media was then removed from cells and replaced with various concentrations of Cu (GTSM), 1 mL to each well. The cells are treated for 6 hours at 37° C. and following the 6 hour treatment, the cells were harvested for western blot analysis using a cell lysis protocol.

HeLa Cells

The cells were plated onto 6 well plate and grown to ~90% confluency before treatment. The DMEM media was removed from cells and replaced with various concentrations of Cu (GTSM), 1 mL to each well. The cells are treated for 6 hours at 37° C. Following the 6 hour treatment, the cells were harvested and protein lysates were prepared using a cell lysis protocol.

Figure 20:
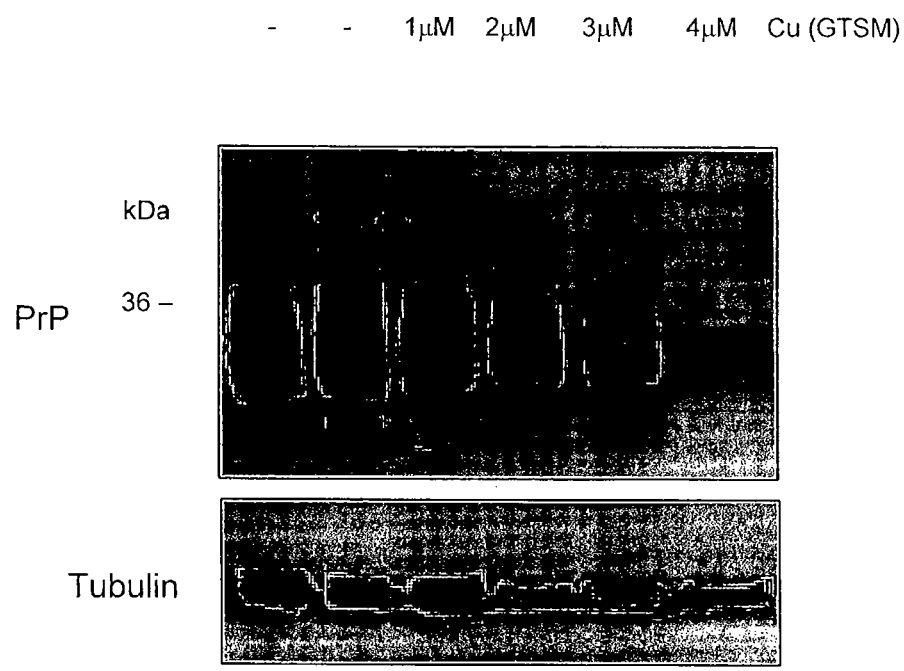
FIG. 20: Graphically illustrates chemical depletion of PrPC in GT1-7 cells following 6 hour treatment with increasing concentrations of Cu (GTSM).
Figure 21:
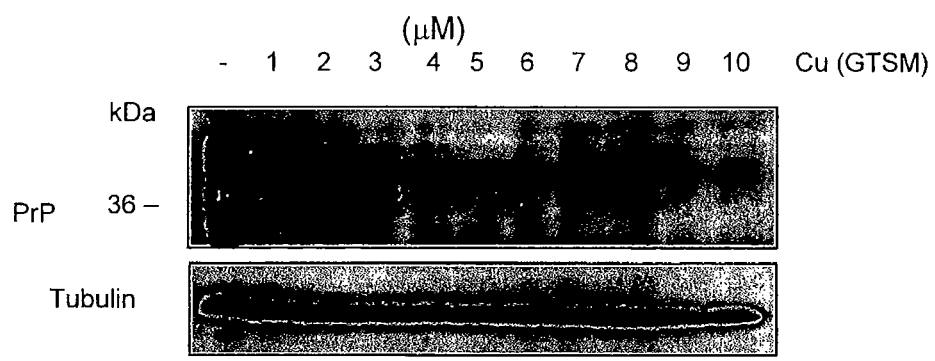
FIG. 21: Graphically illustrates chemical depletion of PrPC in Hela cells following 6 hour treatment with increasing concentrations of Cu (GTSM).

The results are shown in FIGS. 20 and 21. As can be seen there was a significant reduction in PrPc in cells treated with a metal complex.

Example 29 Effect of Metal Complexes on G93A SOD1 ALS Mice

An experiment was carried out in which the effect of the metal complex on G93A-SOD1 mice was determined. Mice of this genetic make up are a useful model for ALS and are used as a mouse model for determining the efficacy of treatment for this condition. A solution of metal complex (CuGTSM) was made up as follows:

Components of Standard Suspension Vehicle (SSV)
Na-carboxymethylcellulose (Na-CMC; medium viscosity; Sigma #C-4888)
Benzyl alcohol
Tween 80® (polyoxyethylenesorbitan monooleate; Sigma #P-8074)
Sodium Chloride (NaCl)
The relative components of the composition were as follows:

TABLE 17

| Composition | Conc. | 1 L | 500 ml |
|---|---|---|---|
| NaCl | 0.9% (w/v) | 9.0 g | 4.5 g |
| Na-CMC | 0.5% (w/v) | 5.0 g | 2.5 g |
| Benzyl alcohol | 0.5% (v/v) | 5.0 ml | 2.5 ml |
| Tween 80 | 0.4% (v/v) | 4.0 ml | 2.0 ml |

Figure 22:
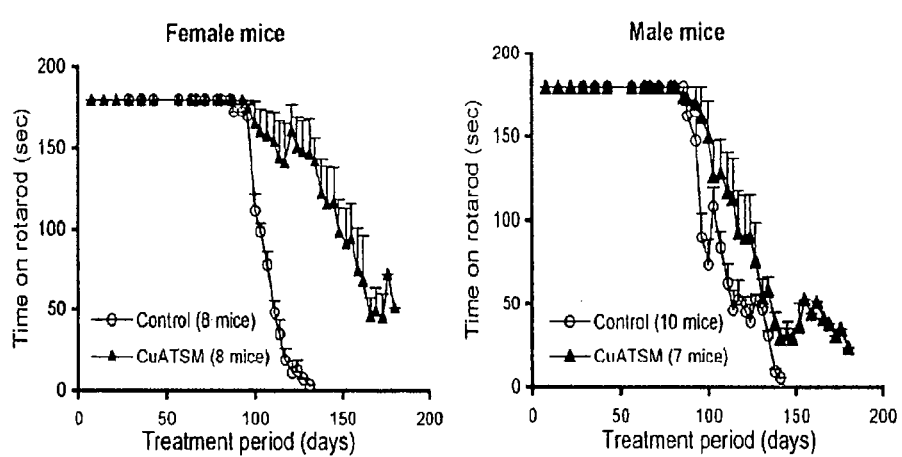
FIG. 22: Shows rotarod data indicating the effectiveness of CuATSM in treating ALS mice.
Figure 23:
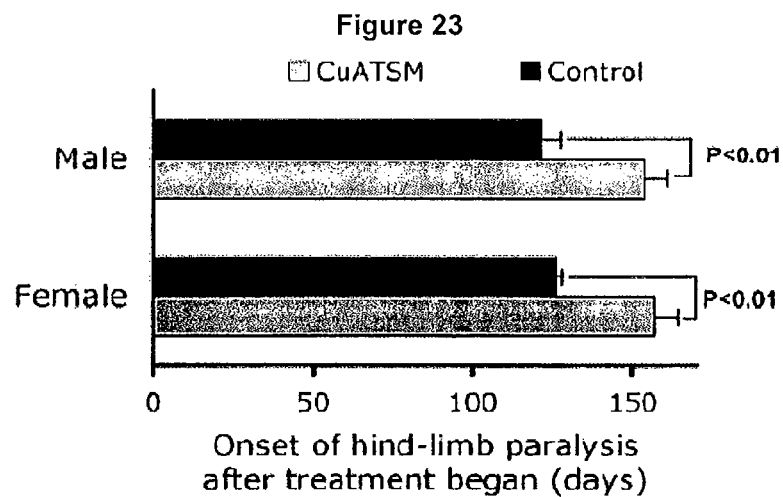
FIG. 23: Shows the onset of hind limb paralysis in ALS mice treated with CuATSM

Cu-ATSM
CuATSM in dosage given to mice was 30 mg/kg through gavaging. It is stored at −20° C. and thawed on the day of administration.
Sonicated the Mixture with Probe, 2×15 sec Bursts.
Dosage given to mice=4× mouse weight. (eg. 25 g mouse received 100 µl of suspension).
Briefly mixed drug by shaking/perturbing before each administration (some slight settling occurs despite sonication).
Cu-ATSM was administered once daily (5 days/week) in TgSOD1G93A mice until they reach end stage (lost of 15-20% body weight, one hindlimb paralysis, and loss of partial motor function). The animal is culled at this point and the survival time plotted. The results are shown in FIG. 22. During the study analysis of the onset of hind leg paralysis was also studied. The results which are shown in FIG. 23 clearly show that CuATSM significantly delays the onset of paralysis in ALS mice.

In addition a survey of the present results in comparison to the literature clearly shows that metal complexes such as Cu ATSM provide the greatest lifespan for G93A-SOD1 mice in comparison to other reported pharmacological treatments. The reported treatments are shown in the table 18 below.

TABLE 18

| Pharmacological treatment | Increased Life Span |
|---|---|
| CuATSM | 31-33 days |
| zVAD-fmk | 27 day |
| Creatine | 20 days |
| AEOL 10150 | 20 days |
| Ro 28-2653 | 13 days |
| Minocycline | 11-21 days |
| Riluzole | 10-15 days |
| Ceftriaxone | 10 days |
| β-lactam antibiotic Ginseng SOD1 | 7 days |
| Gabapentin | No effect |
| Vitamin E | No effect |
| Lysine Acetyl salicylate | No effect |

Example 30 Effect of Metal Complexes on EGFR

Figure 24A:
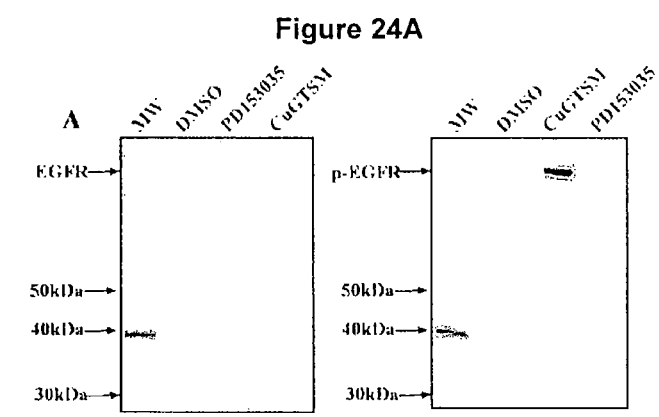
FIG. 24A: Shows Western blotting of cell lysates. CuGTSM (25 µM) activated EGFR (tyr1068) in U87MG-EGFR cells compared to vehicle control. The addition of PD153035 to CuGTSM-treated cells inhibited activation of EGFR (A).
Figure 24B:
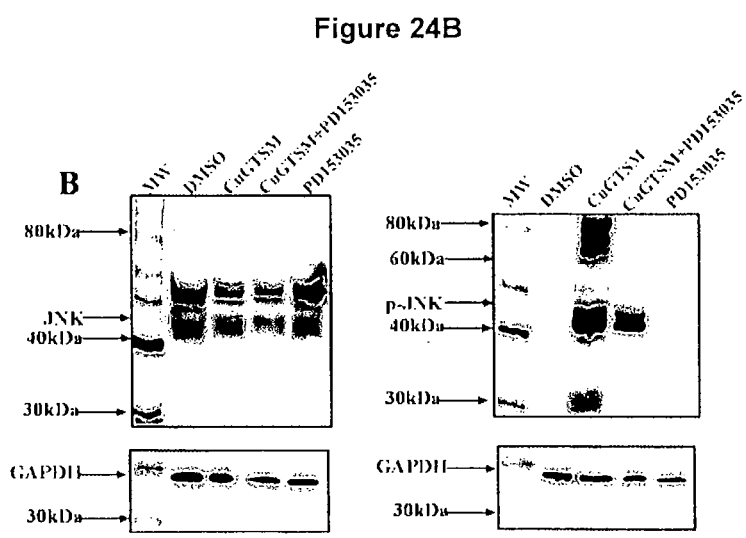
FIGS. 24 B to 24D: Show similar experiments as for FIG. 24A but for JNK (B), GSK3 (C) and ERK (D) respectively.
Figure 24C:
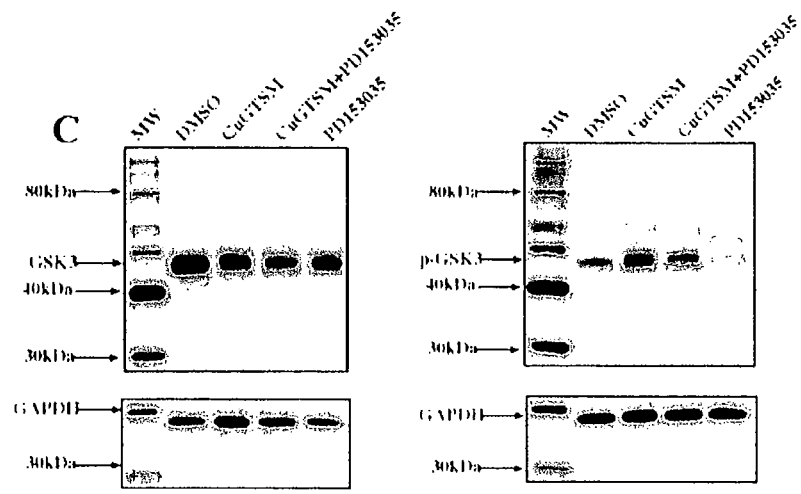
Figure 24D:
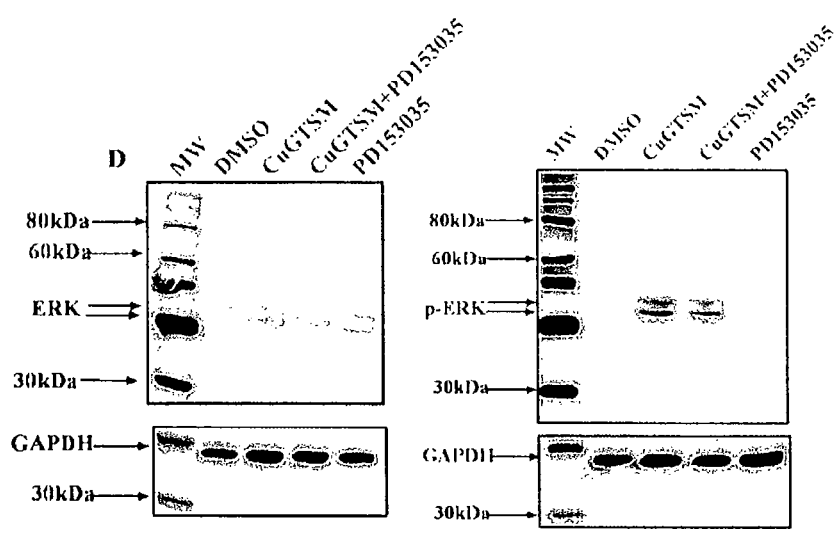

Transfected U87MG-EGFR cells were treated with 25 µM CuGTSM or DMSO as vehicle control for 5 hr and EGFR phosphorylation (tyr1068) determined by Western blot. Antisera to EGFRtyr1068 was routinely used as this is one of the critical tyrosine residues involved in EGFR activation and downstream signalling. It is also routinely reported in the literature on EGFR activation. FIG. 24A shows that EGFR phosphorylation and therefore activation occurred on treatment with CuGTSM compared to vehicle control.

Example 31 Effect of EGFR Activation by CuGTSM on Downstream Phosphorylation of ERK, GSK3 and JNK A study was carried out to determine if kinase pathways modulated by CuGTSM were mediated by activation of EGFR. This was done by treating U87MG-EGFR cells with 25 µM DMSO, CuGTSM, CuGTSM plus 10 µM PD153035 (EGFR inhibitor), or 10 µM PD153035 alone. The activation of ERK, GSK3 and JNK was then determined by Western blot. FIG. 23 shows that there was a decrease in CuGTSM-induced phosphorylation of JNK, GSK3 and ERK in the presence of PD153035, although the activation of these kinases was not completely ablated by the EGFR inhibitor. This suggested that whilst the activation of EGFR did regulate the activation of these downstream kinases to an extent, their regulation is also potentially being controlled by other receptor pathways not examined in this study. The western blots are shown in FIGS. 24A to 24 D.

The claims defining the invention are as follows:
1. A method comprising
providing a subject suffering from a disease selected from the group consisting of Parkinson's disease and amyotrophic lateral sclerosis; and
administering to the subject a therapeutically effective amount of a complex of Formula (I):

Formula (I)

where:
the complex is symmetrical;
M is Cu or Zn;
$R^1$ and $R^5$ are each hydrogen;
$R^2$ and $R^6$ are each methyl, ethyl, or phenyl; and
$R^3$ and $R^4$ are each methyl.

2. The method of claim 1 where the disease is Parkinson's disease.

3. The method of claim 1 where the disease is amyotrophic lateral sclerosis.

4. The method of claim 1 where M is Cu.

5. The method of claim 1 where M is Zn.

6. The method of claim 1 where R2 and R6 are each methyl.

7. The method of claim 1 where R2 and R6 are each ethyl.

8. The method of claim 1 where R2 and R6 are each phenyl.

9. The method of claim 2 where M is Cu and R2 and R6 are each methyl.

10. The method of claim 2 where M is Cu and R2 and R6 are each ethyl.

11. The method of claim 2 where M is Cu and R2 and R6 are each phenyl.

12. The method of claim 2 where M is Zn and R2 and R6 are each methyl.

13. The method of claim 2 where M is Zn and R2 and R6 are each ethyl.

14. The method of claim 2 where M is Zn and R2 and R6 are each phenyl.

15. The method of claim 3 where M is Cu and R2 and R6 are each methyl.

16. The method of claim 3 where M is Cu and R2 and R6 are each ethyl.

17. The method of claim 3 where M is Cu and R2 and R6 are each phenyl.

18. The method of claim 3 where M is Zn and R2 and R6 are each methyl.

19. The method of claim 3 where M is Zn and R2 and R6 are each ethyl.

20. The method of claim 3 where M is Zn and R2 and R6 are each phenyl.

* * * * *